(12) United States Patent
Zhang et al.

(10) Patent No.: US 10,882,850 B2
(45) Date of Patent: Jan. 5, 2021

(54) ORGANIC COMPOUND WITH TRIAZINE AND BENZIMIDAZOLE AS CORE AND APPLICATION THEREOF IN ORGANIC ELECTROLUMINESCENT DEVICE

(71) Applicant: Jiangsu Sunera Technology Co., Ltd, Wuxi (CN)

(72) Inventors: Zhaochao Zhang, Wuxi (CN); Chong Li, Wuxi (CN)

(73) Assignee: JIANGSU SUNERA TECHNOLOGY CO., LTD, Wuxi (CN)

( * ) Notice: Subject to any disclaimer, the term of this patent is extended or adjusted under 35 U.S.C. 154(b) by 292 days.

(21) Appl. No.: 16/081,432

(22) PCT Filed: Nov. 30, 2017

(86) PCT No.: PCT/CN2017/113767
§ 371 (c)(1),
(2) Date: Aug. 31, 2018

(87) PCT Pub. No.: WO2018/192227
PCT Pub. Date: Oct. 25, 2018

(65) Prior Publication Data
US 2019/0071430 A1  Mar. 7, 2019

(30) Foreign Application Priority Data
Apr. 20, 2017 (CN) .......................... 2017 1 0261803

(51) Int. Cl.
*H01L 51/50* (2006.01)
*C07D 403/14* (2006.01)
(Continued)

(52) U.S. Cl.
CPC ......... *C07D 403/14* (2013.01); *C07D 401/14* (2013.01); *C07D 405/14* (2013.01);
(Continued)

(58) Field of Classification Search
None
See application file for complete search history.

(56) References Cited

U.S. PATENT DOCUMENTS

2006/0194076 A1* 8/2006 Nariyuki ............. H01L 51/5016
428/690

FOREIGN PATENT DOCUMENTS

WO  2013172255 A1  11/2013
WO  2016107446 A1  7/2016

OTHER PUBLICATIONS

Wade White et al. "Linear and star-shaped benzimidazolyl derivatives: syntheses, photophysical properties and use as highly efficient electron transport materials in OLEDs", Dalton Trans., 2010, 39, 892-899.

* cited by examiner

*Primary Examiner* — Gregory D Clark
(74) *Attorney, Agent, or Firm* — Bayramoglu Law Offices LLC

(57) ABSTRACT

An organic compound has a structure represented by formula (1):

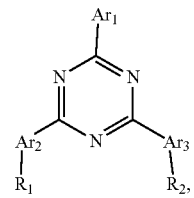

and $Ar_1$ represents phenyl, naphthyl, biphenyl, terphenyl, anthryl, dibenzofuranyl, dibenzothiophenyl, 9,9-dimethyl-
(Continued)

fluorenyl or 9-phenylcarbazolyl, substituted or unsubstituted by halogen atoms, protium atoms, deuterium atoms, tritium atoms, and linear or branched alkyl with 1 to 10 carbons; $Ar_2$ and $Ar_3$ each independently represents a single bond or one selected from the group consisting of phenyl, naphthyl, biphenyl, terphenyl, anthryl or pyridyl, substituted or unsubstituted by halogen atoms, protium atoms, deuterium atoms, tritium atoms, and linear or branched alkyl with 1 to 10 carbons; $R_1$, $R_2$ each independently represents a structure represented by the following formulas:

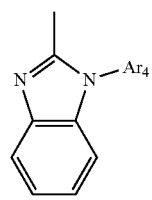

formula (2)

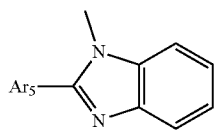

formula (3)

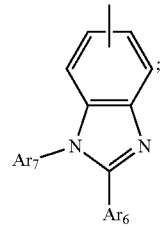

formula (4)

and $Ar_4$, $Ar_5$, $Ar_6$, $Ar_7$ each independently represents one selected from the group consisting of phenyl, naphthyl, biphenyl, terphenyl or pyridyl, substituted or unsubstituted by halogen atoms, linear or branched alkyl with 1 to 10 carbons.

11 Claims, 2 Drawing Sheets

(51) Int. Cl.
    *C07D 401/14* (2006.01)
    *C07D 405/14* (2006.01)
    *C07D 409/14* (2006.01)
    *H01L 51/00* (2006.01)

(52) U.S. Cl.
    CPC ........ *C07D 409/14* (2013.01); *H01L 51/0058* (2013.01); *H01L 51/0067* (2013.01); *H01L 51/0072* (2013.01); *H01L 51/0073* (2013.01); *H01L 51/0074* (2013.01); *H01L 51/5096* (2013.01); *H01L 51/5072* (2013.01)

| Name of material | Compound 32 | CBP |
|---|---|---|
| After film-forming of the material |  |  |
| 72h after the experiment |  |  |
| 600h after the experiment |  | ---------- |

ORGANIC COMPOUND WITH TRIAZINE AND BENZIMIDAZOLE AS CORE AND APPLICATION THEREOF IN ORGANIC ELECTROLUMINESCENT DEVICE

CROSS REFERENCE TO RELATED APPLICATIONS

This application is the national phase entry of International Application No. PCT/CN2017/113767, filed on Nov. 30, 2017, which is based upon and claims priority to Chinese Patent Application No. CN201710261803.6, filed on Apr. 20, 2017, the entire contents of which are incorporated herein by reference.

TECHNICAL FIELD

The present invention relates to the field of semiconductor technology, and in particular, to an organic compound with triazine and benzimidazole as the core and an application thereof in an organic electroluminescent device.

BACKGROUND

Organic electroluminescent (OLED, Organic Light Emission Diodes) device technology can be used to fabricate not only a novel display product but also a novel lighting product. It is expected to replace the existing liquid crystal display and fluorescent lamp lighting, and has a promising application prospect. The OLED light-emitting device is of a sandwich structure, and includes an electrode material film layer and organic functional materials sandwiched between different electrode film layers, and various functional materials are overlapped with one another according to purposes so as to together form an OLED light-emitting device. Positive and negative charges in the organic functional material film layer are acted by the electric field then combined in the light-emitting layer when the OLED light-emitting device serves as a current device and a voltage is applied to electrodes at two ends of the OLED light-emitting device, that is, the OLED electroluminescence is generated.

Currently, the OLED display technology has been applied in the fields of smart phones, tablet computers and the like, and will be further applied in the fields of large size devices such as TVs. However, the huge gap between the external quantum efficiency and the internal quantum efficiency of an OLED has greatly restricted the development of OLED. Therefore, how to improve the light extraction efficiency of an OLED device has become a heat-point in research. Total reflection may occur at the interface between the ITO film and the glass substrate and the interface between the glass substrate and the air, and the light emitted to the forward outer space of the OLED device accounts for about 20% of the total amount of the light emitted from organic material film, and the remaining about 80% of the light is mainly limited in the organic material film, the ITO film and the glass substrate in a guided wave form. The relatively low light extraction efficiency of conventional OLED devices (about 20%) severely restricts the development and application of OLED devices. How to reduce the total reflection effect in the OLED device and improve the ratio of the light coupling to the forward outer space of the device (light extraction efficiency) attract considerable attention.

At present, an important method for improving the external quantum efficiency of the OLED is to form structures, such as wrinkles, photonic crystals, micro lens arrays (MLA) or surface capping layers on the light-emitting surface of the substrate. The first two structures will affect the radiation spectrum angle distribution of the OLED and the third structure is complex in fabrication process, the use of the surface capping layer is simple in process, and has a luminous efficiency improved by more than 30%, and thus has gained great attention. According to the optical principle, when light is transmitted through a substance having a refractive index of $n_1$ to a substance having a refractive index of $n_2$ ($n_1 > n_2$), the light can be incident to the substance having a refractive index of $n_2$ only when the incident angle is less than $\arcsin(n_2/n_1)$, and the absorptivity B can be calculated by the following formula:

$$B = \frac{1 - \sqrt{1 - \left(\frac{n_2}{n_1}\right)^2}}{2}.$$

Let $n_1 = n_{general\ OLED\ organic\ matrial} = 1.70$, $n_2 = n_{glass} = 1.46$, then $2B = 0.49$. Assuming that light propagating outwards is totally reflected by the metal electrodes, only 51% of the light can be waveguided by high-refractive-index organic film and ITO layer, and the transmittance of light emitted from the glass substrate to the air also can be calculated. Therefore, when light emitted from the organic layer is emitted to outside of the device, only about 17% of the light is visible. Accordingly, aiming at the current situation that the light extraction efficiency of the existing OLED device is low, it is necessary to add a CPL layer, that is, light extraction materials, to the device structure, and the refractive index of the surface capping layer material should be as high as possible, according to the optical absorption and refraction principles.

Current researches on improving the performance of the OLED light-emitting device include: reducing the driving voltage of the device, improving the light-emitting efficiency of the device, prolonging service life of the device and etc. In order to continuously improve the performance of the OLED device, not only the innovation from the structure and manufacturing process of OLED devices, but also the continuous research and innovation of OLED optoelectronic functional materials are needed to create OLED functional materials with higher performances.

SUMMARY

In view of the problems existing in the prior art, the applicant provides an organic compound with triazine and benzimidazole as the core and an application thereof in an organic electroluminescent device. The compound of the present invention contains a structure of triazine and benzimidazole, has a relatively high glass transition temperature and molecular thermal stability, is low in absorption and high in refractive index in the field of visible light, and is capable of effectively improving the light extraction efficiency of an OLED device when applied to a CPL layer of the OLED device; with a deep HOMO energy level and a wide forbidden band (Eg) energy level, the triazine and benzimidazole can be used as the hole blocking layer or the electron transport layer material, for blocking holes from transmitting from the light-emitting layer to the electron layer, so that the recombination degree of the hole and the electron in the light-emitting layer can be improved, thus the light-emitting efficiency of the OLED device can be enhanced and the service life of the OLED device can be prolonged.

Technical solutions of the present invention are as follows: the applicant provides an organic compound with triazine and benzimidazole as the core, and the structure of the organic compound is represented by the following formula (1):

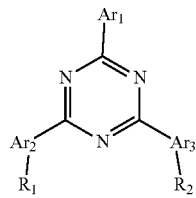

formula (1)

wherein, $Ar_1$ represents phenyl, naphthyl, biphenyl, terphenyl, anthryl, dibenzofuranyl, dibenzothiophenyl, 9,9-dimethylfluorenyl or 9-phenylcarbazolyl, substituted or unsubstituted by halogen atoms, protium atoms, deuterium atoms, tritium atoms, linear or branched alkyl with 1 to 10 carbon atoms; $Ar_2$ and $Ar_3$ each independently represents one of phenyl, naphthyl, biphenyl, terphenyl, anthryl or pyridyl, substituted or unsubstituted by halogen atoms, protium atoms, deuterium atoms, tritium atoms, linear or branched alkyl with 1 to 10 carbon atoms; $Ar_2$ and $Ar_3$ further independently represents a single bond; $Ar_1, Ar_2, Ar_3$ are identical or different; $R_1, R_2$ each independently represents a structure represented by the following formula (2), formula (3) or formula (4):

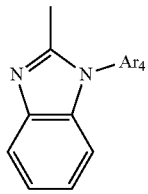

formula (2)

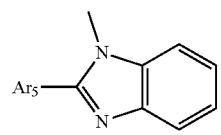

formula (3)

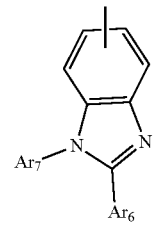

formula (4)

wherein, $Ar_4, Ar_5, Ar_6, Ar_7$ each independently represents one of phenyl, naphthyl, biphenyl, terphenyl or pyridyl, substituted or unsubstituted by halogen atoms, linear or branched alkyl with 1 to 10 carbon atoms; $R_1, R_2$ are identical or different.

Preferably, the particular structural formula of the organic compound is any one of:

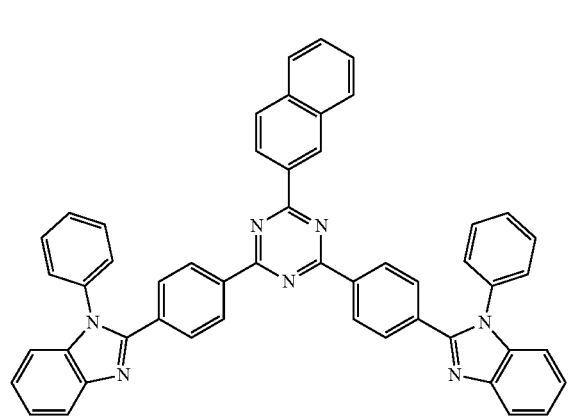

(1)

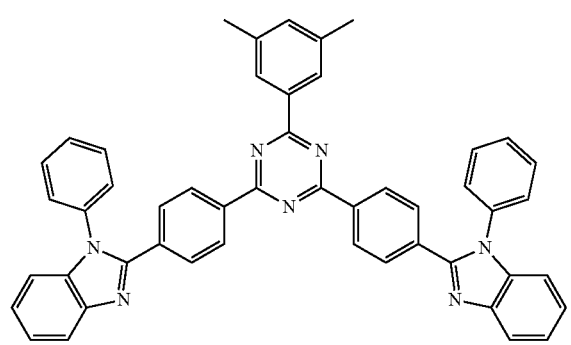

(2)

-continued
(3)
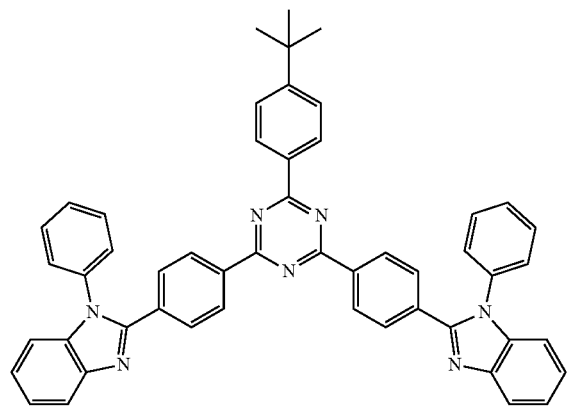
(4)
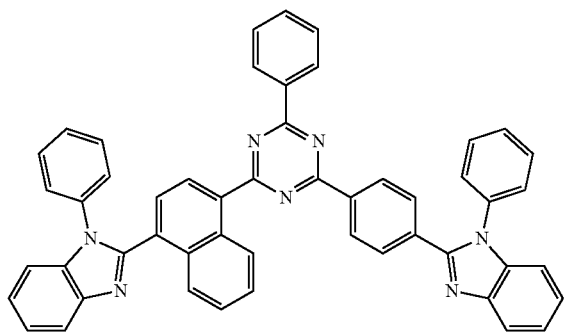
(5)
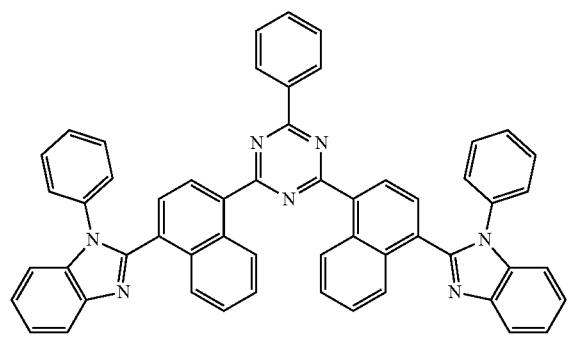
(6)
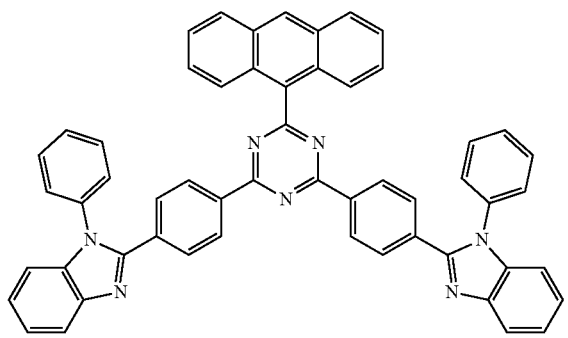
(7)
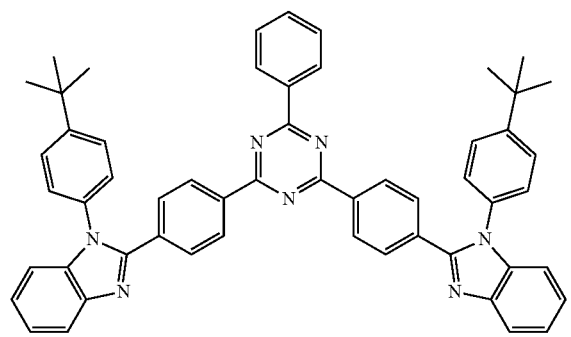
(8)
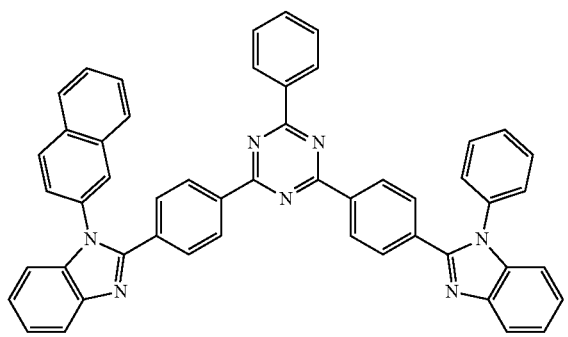
(9)
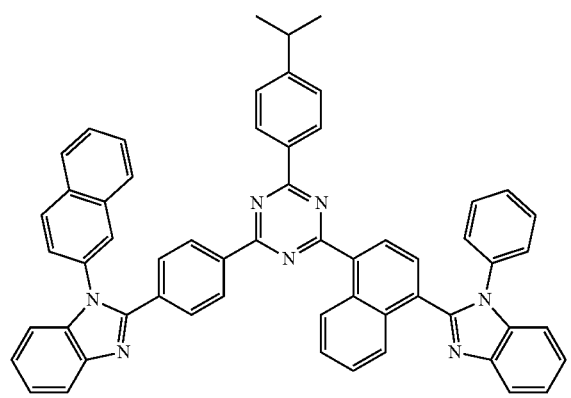
(10)
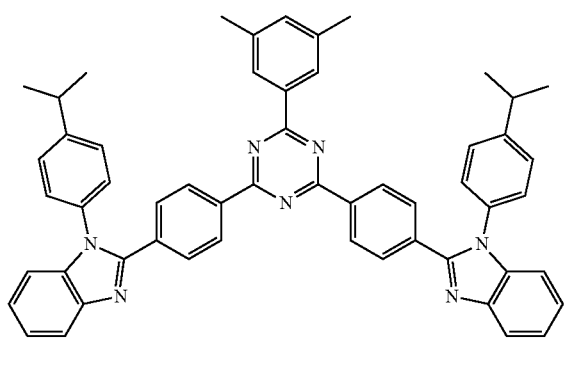

-continued
(11)
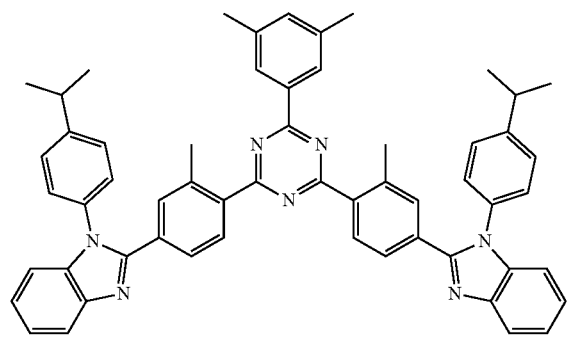
(12)
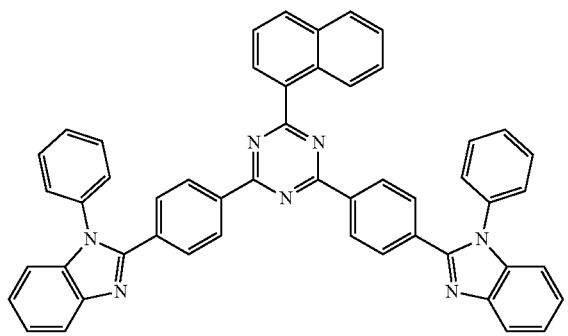
(13)
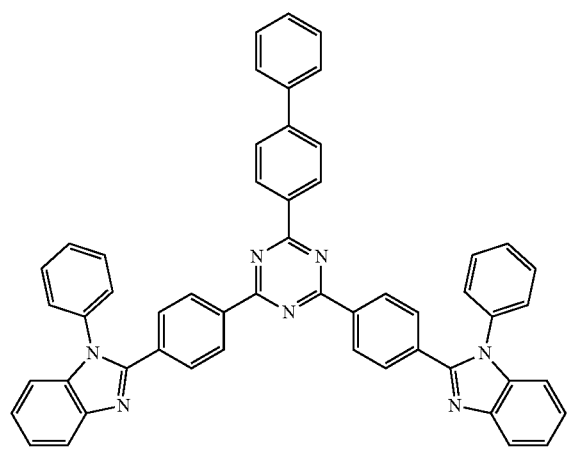
(14)
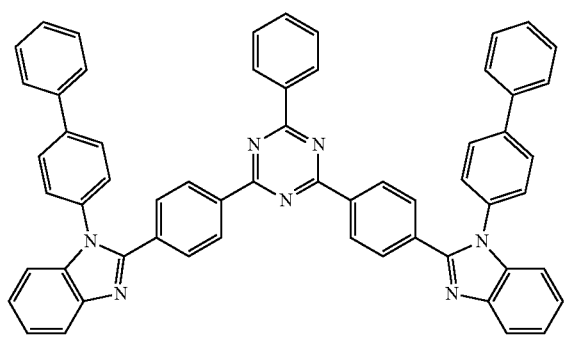
(15)
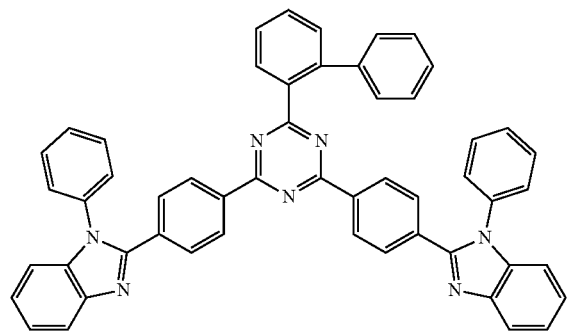
(16)
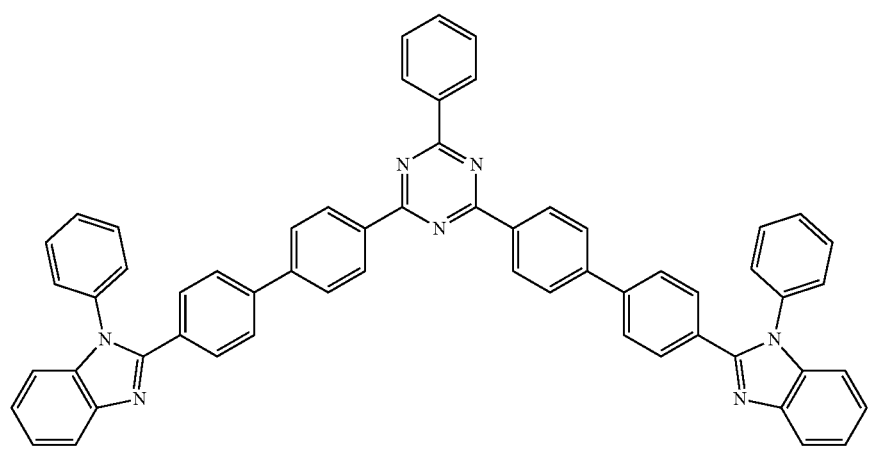

-continued
(17)
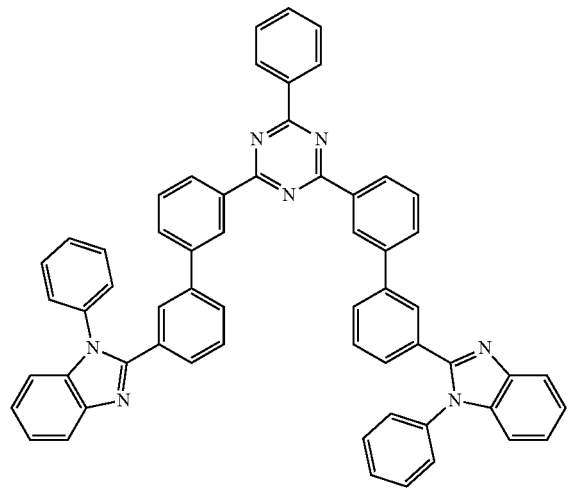
(18)
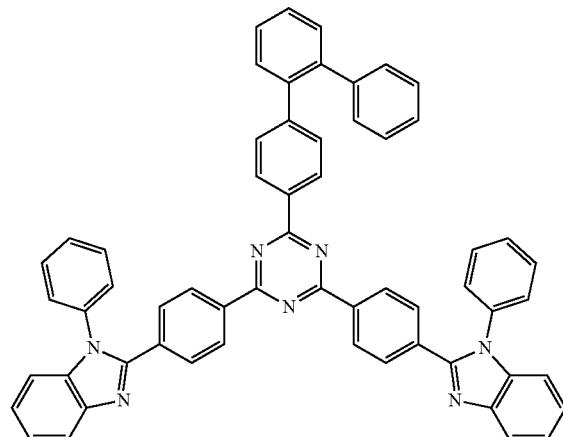
(19)
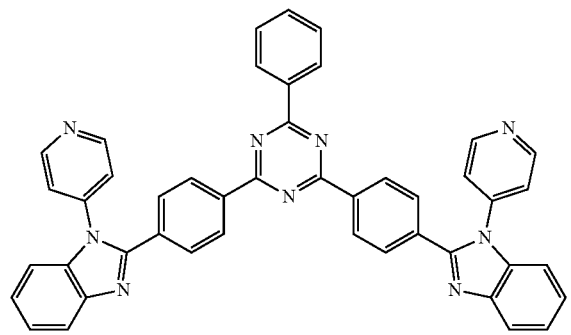
(20)
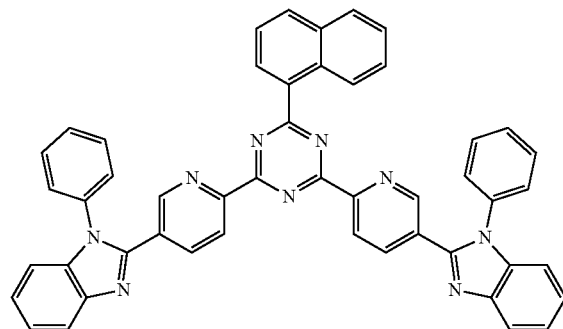
(21)
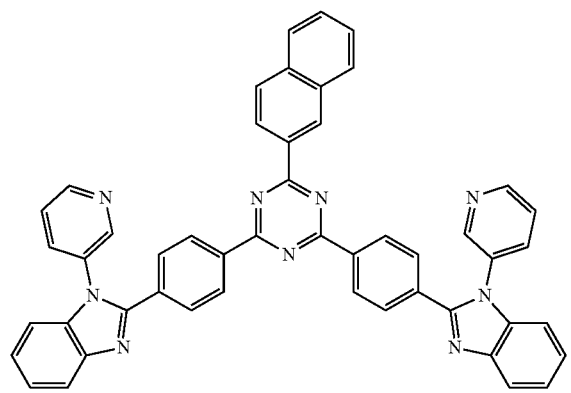
(22)
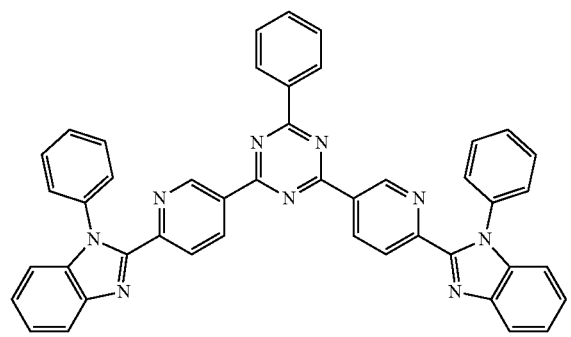

-continued
(23)
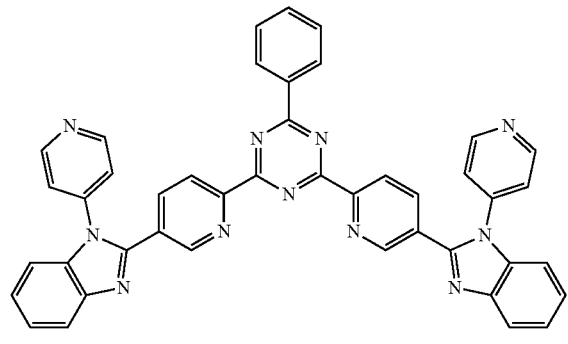
(24)
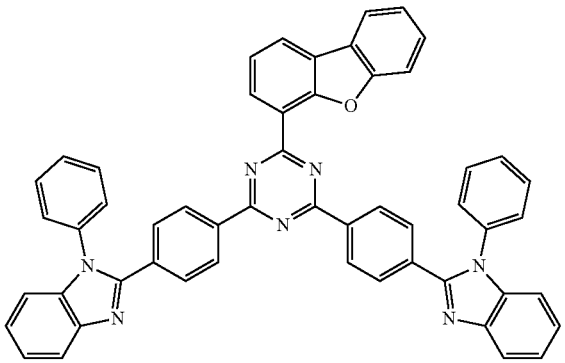
(25)
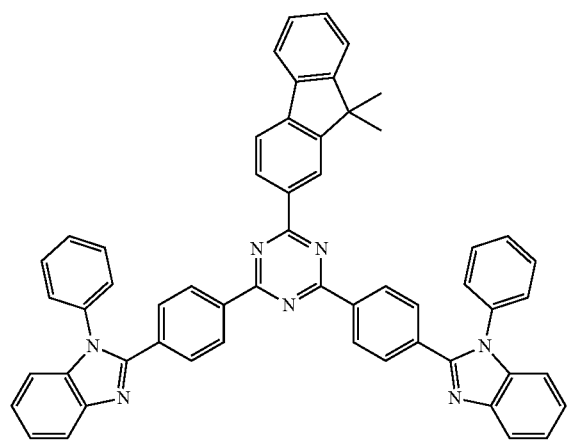
(26)
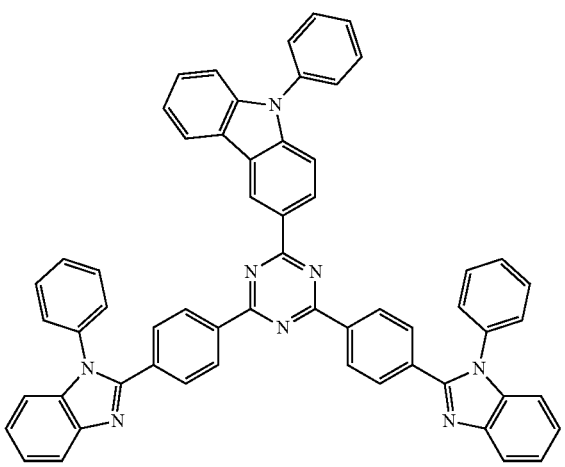
(27)
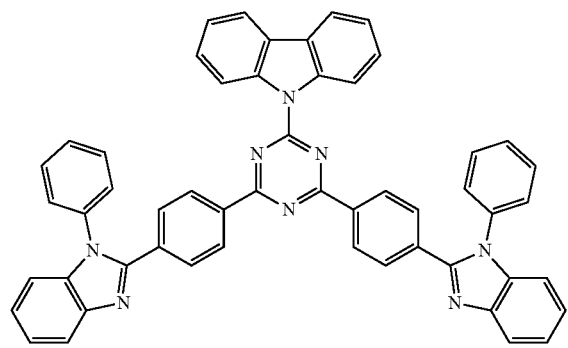
(28)
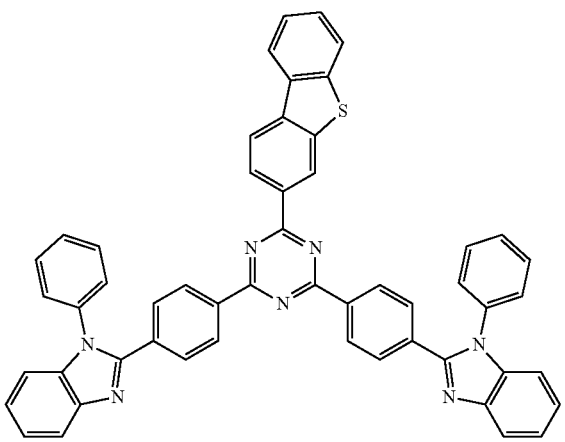

-continued
(29)
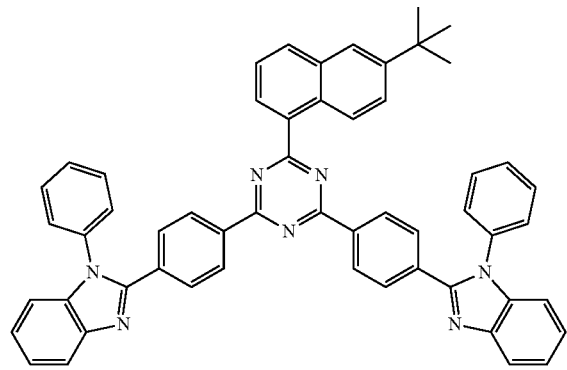
(30)
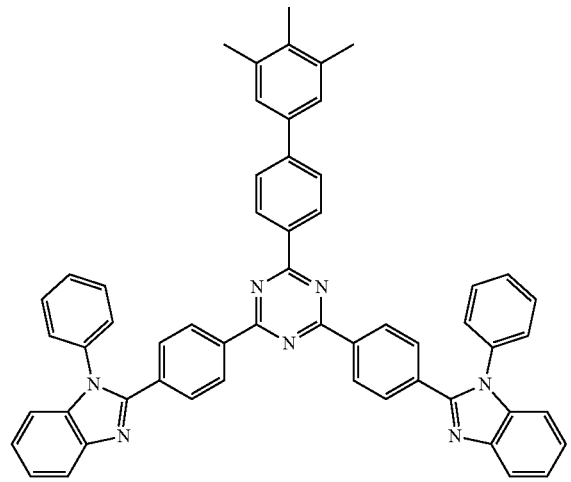
(31)
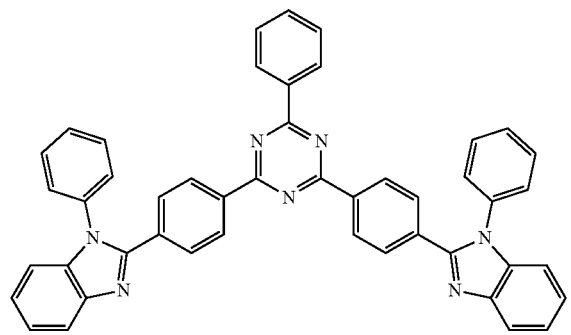
(32)
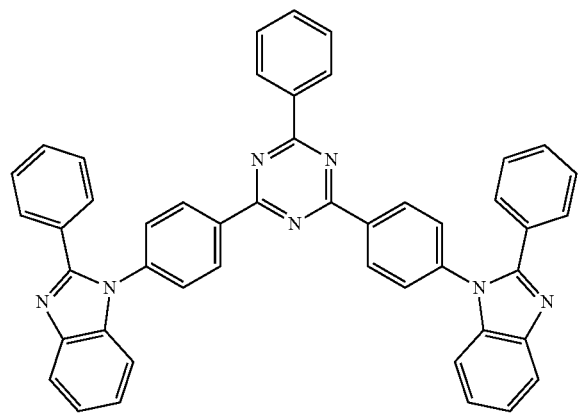
(33)
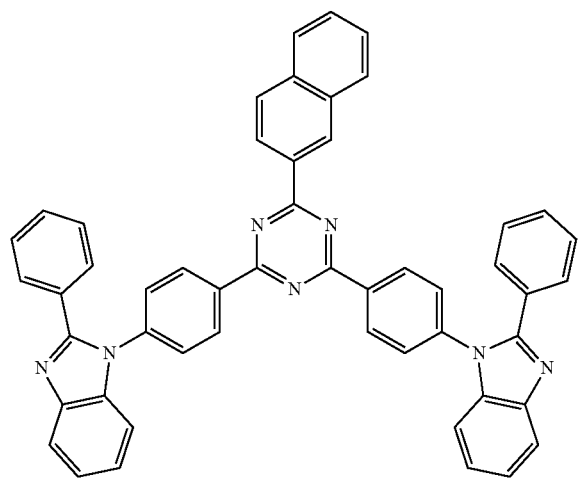
(34)
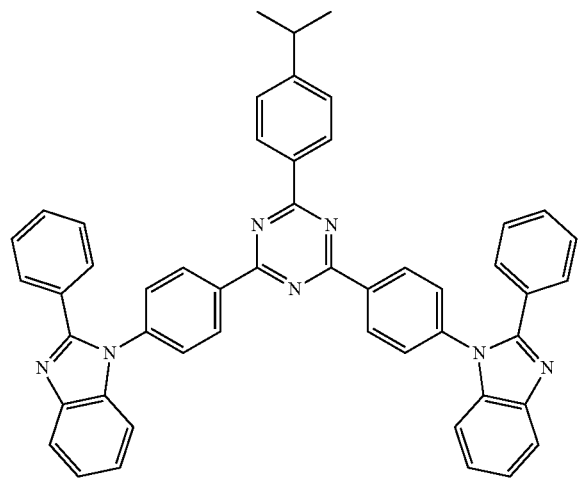

-continued
(35)
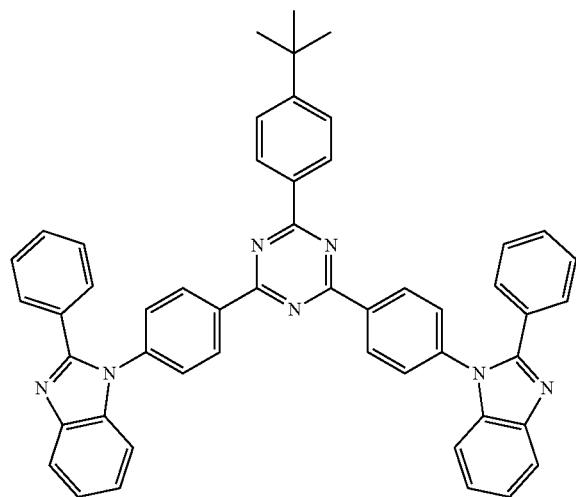
(36)
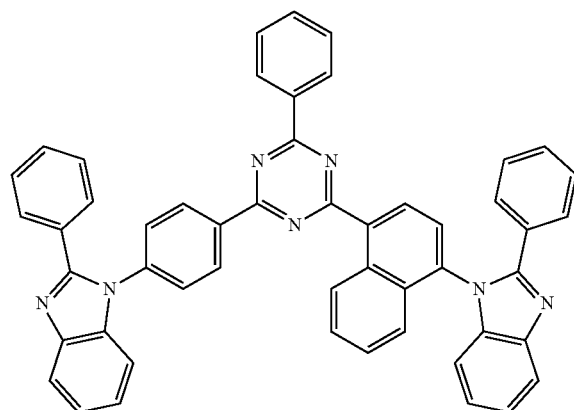
(37)
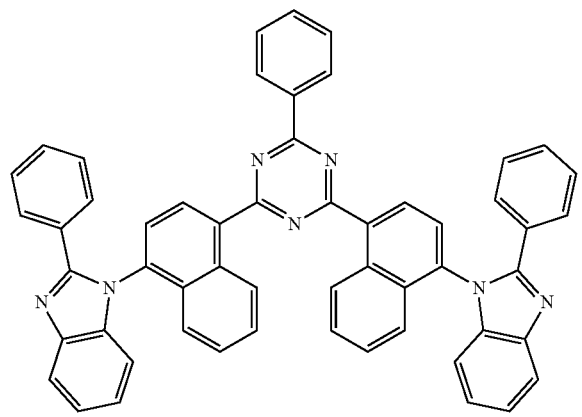
(38)
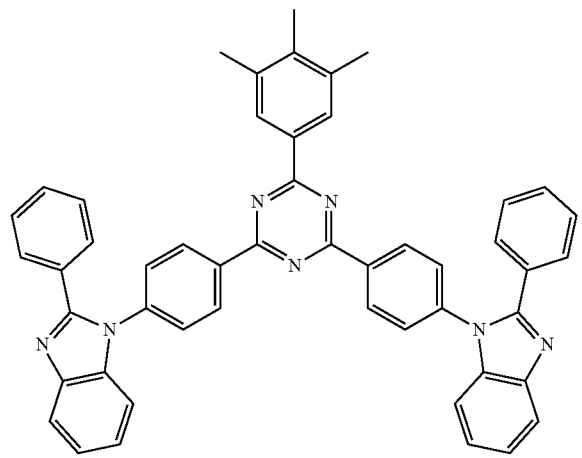
(39)
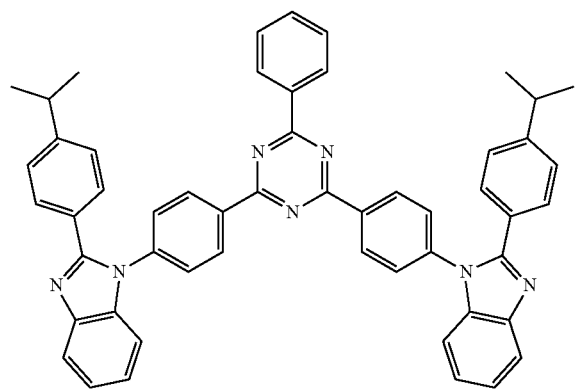
(40)
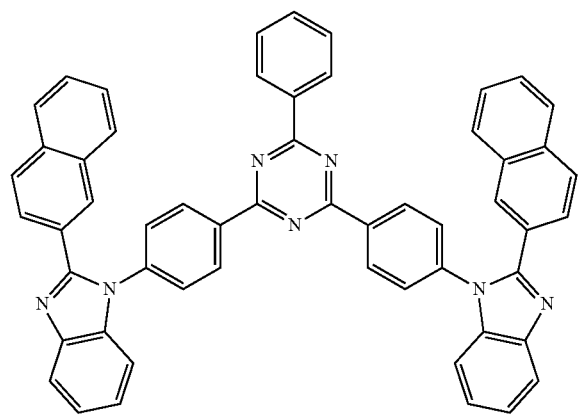

-continued
(41)
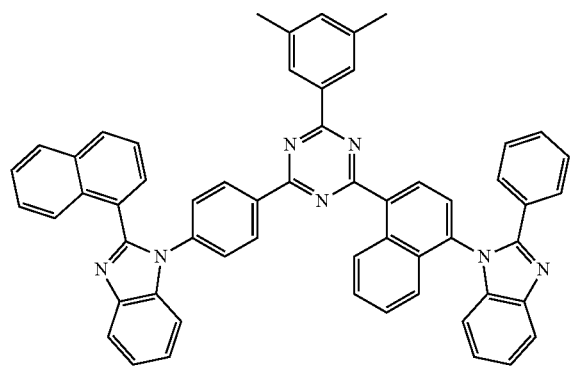
(42)
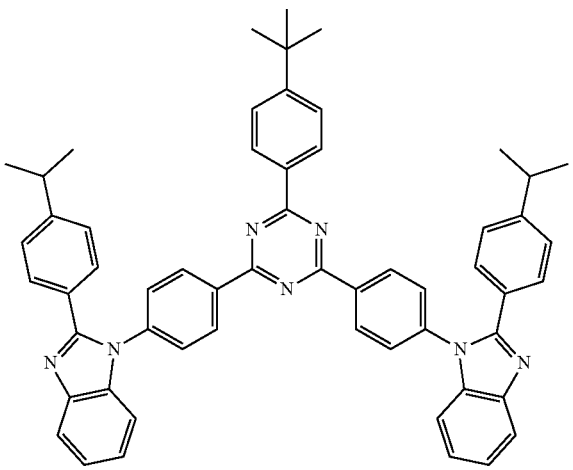
(43)
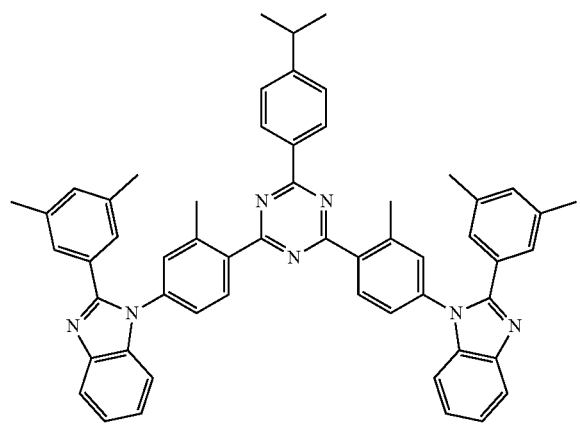
(44)
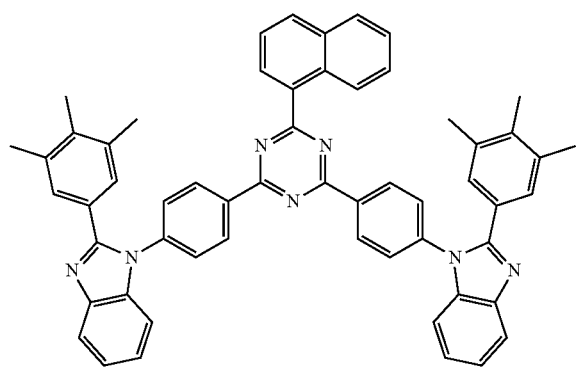
(45)
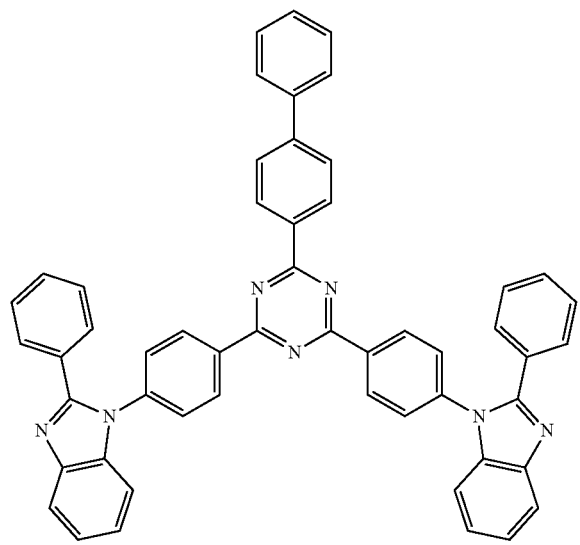
(46)
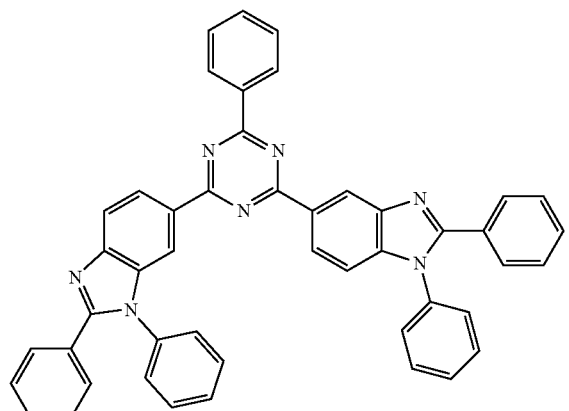

(47)
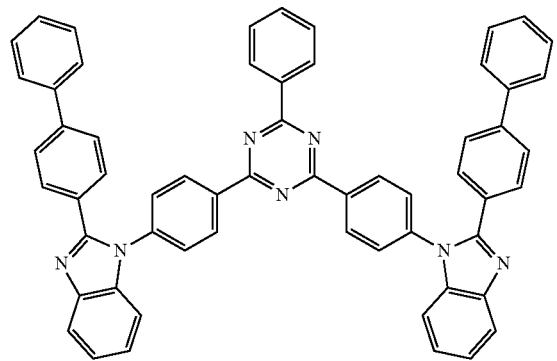
(48)
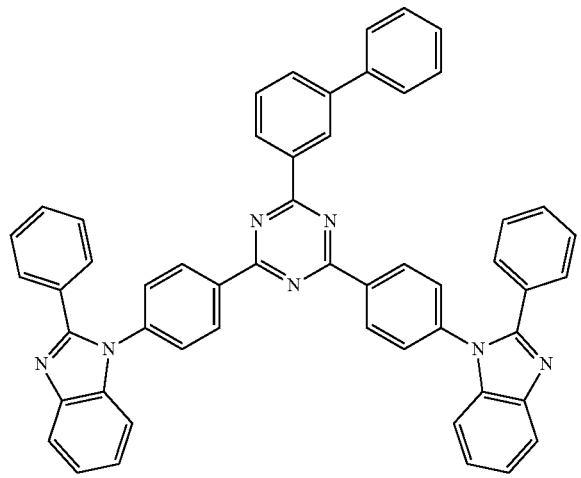
(49)
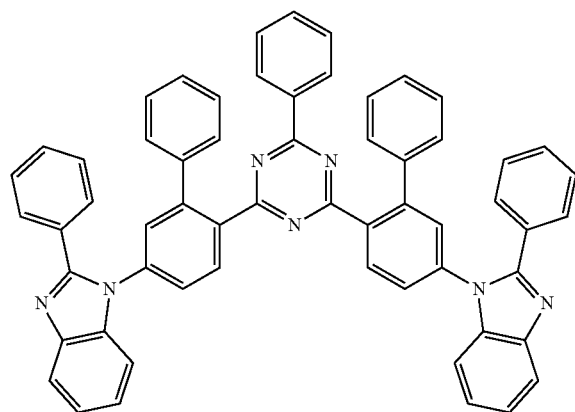
(50)
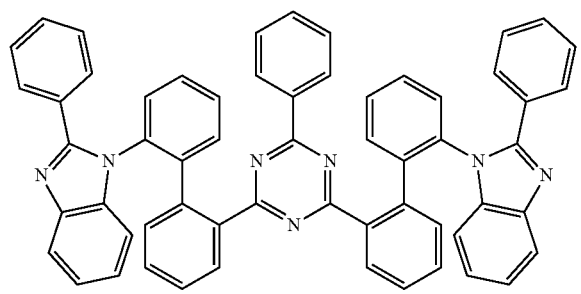
(51)
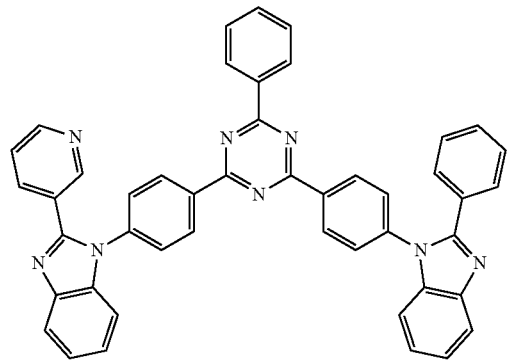
(52)
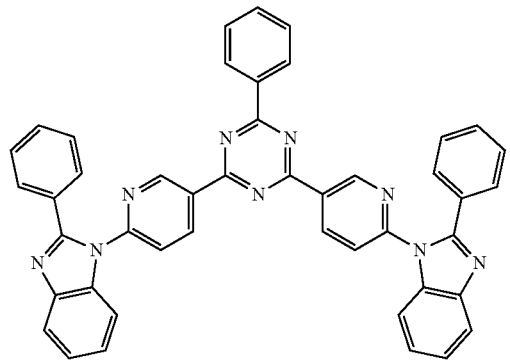

-continued
(53)
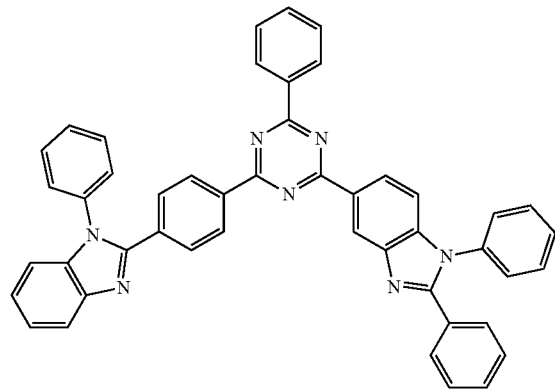
(54)
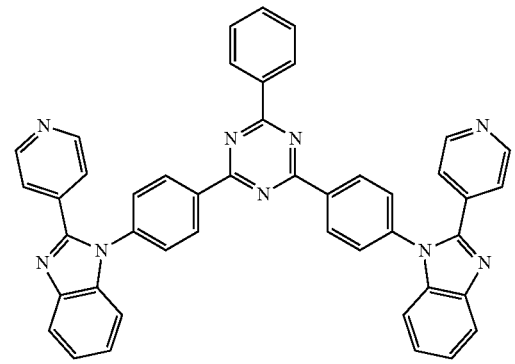
(55)
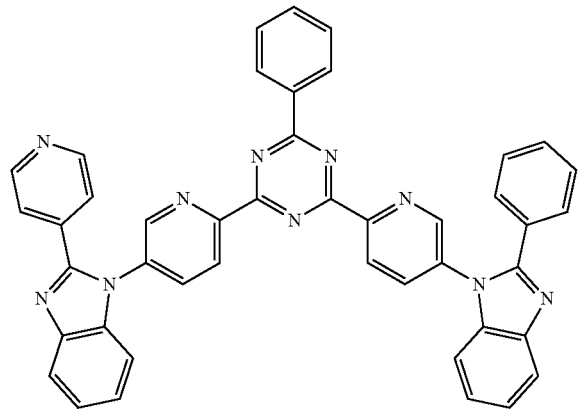
(56)
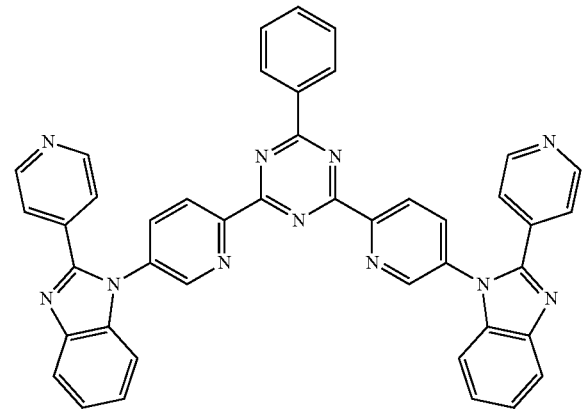
(57)
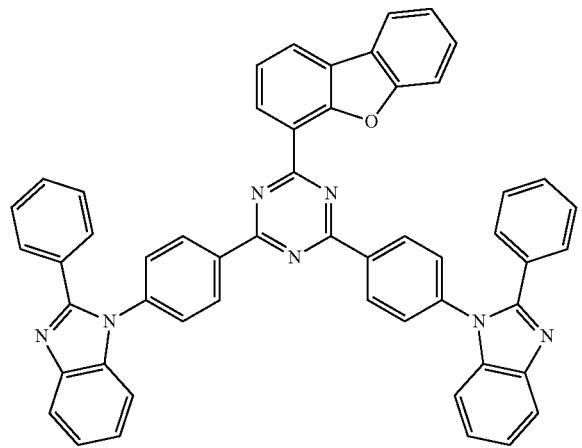
(58)
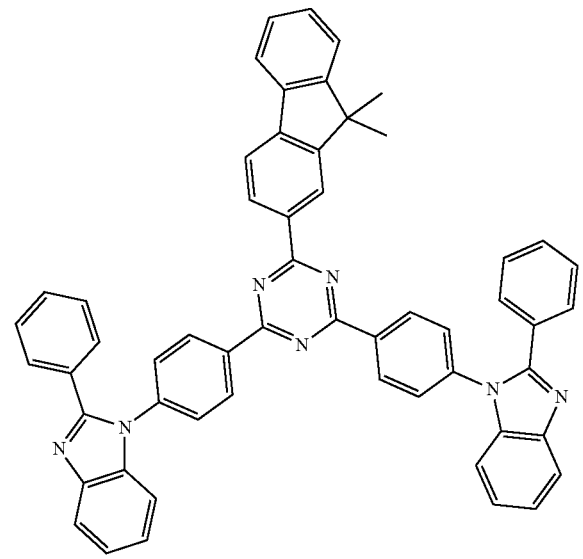

-continued
(59)
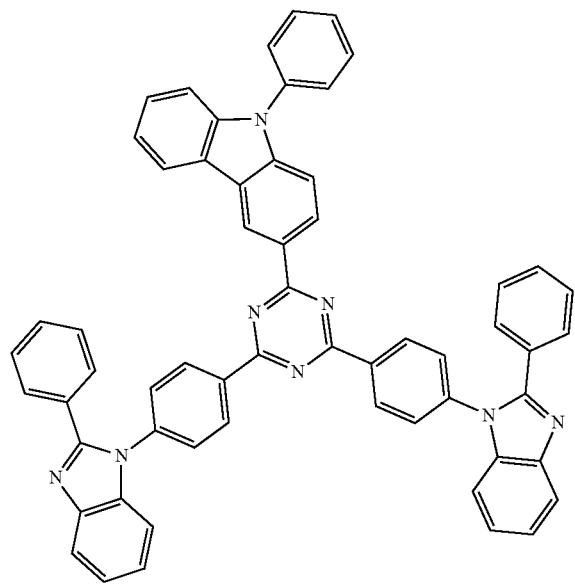
(60)
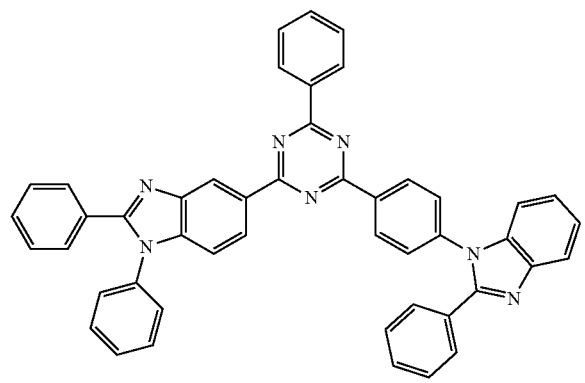
(61)
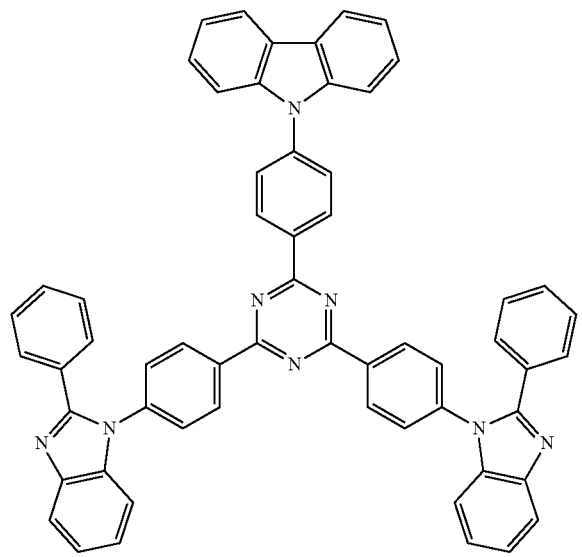
(62)
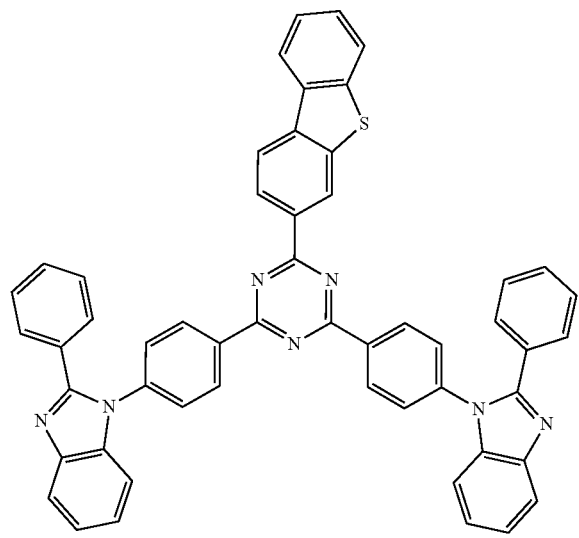

-continued
(63)
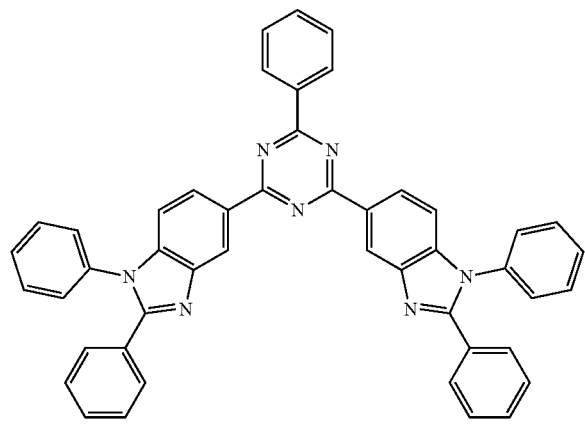
(64)
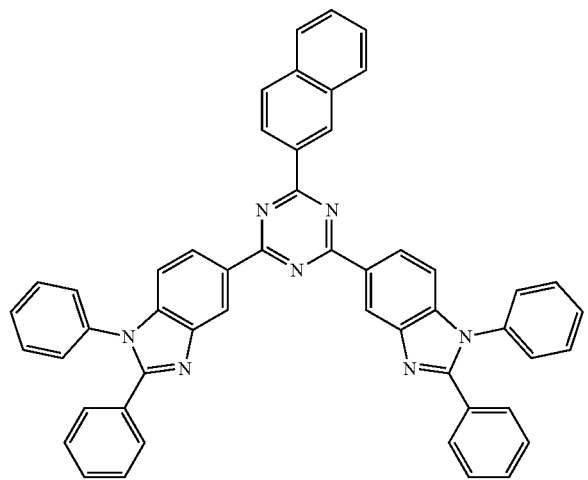
(65)
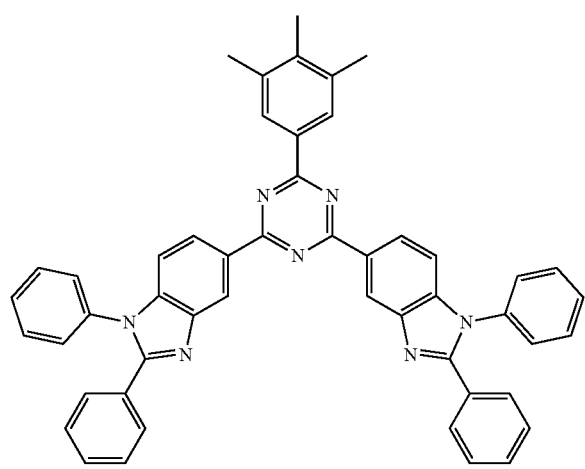
(66)
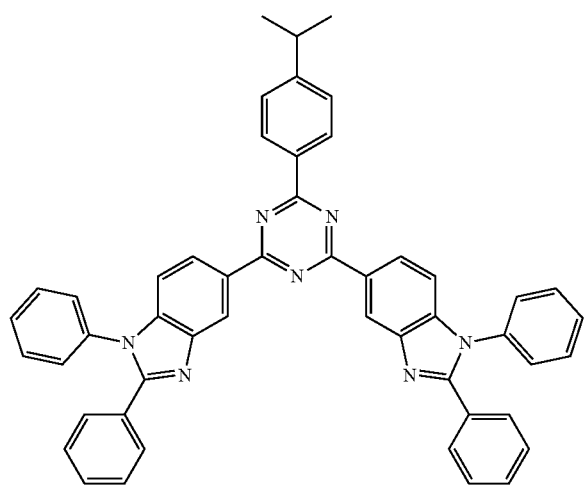
(67)
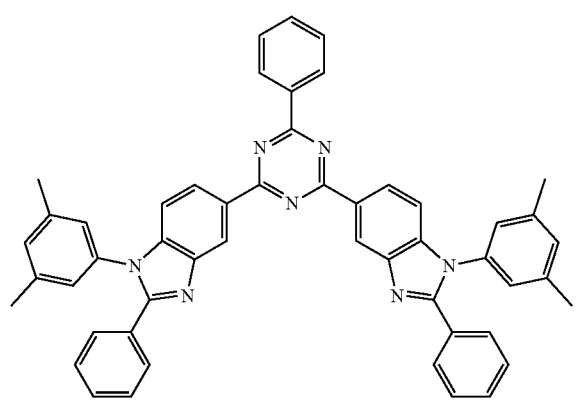
(68)
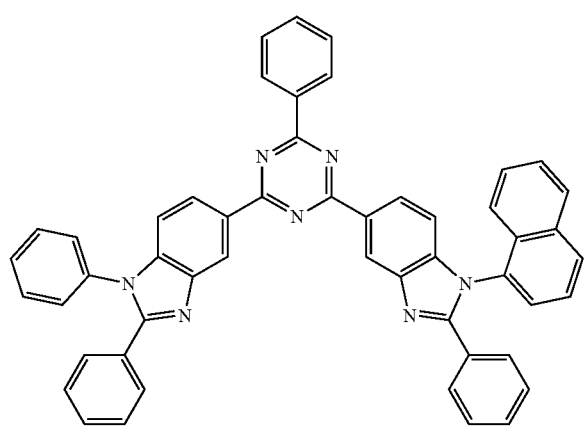

-continued
(69)
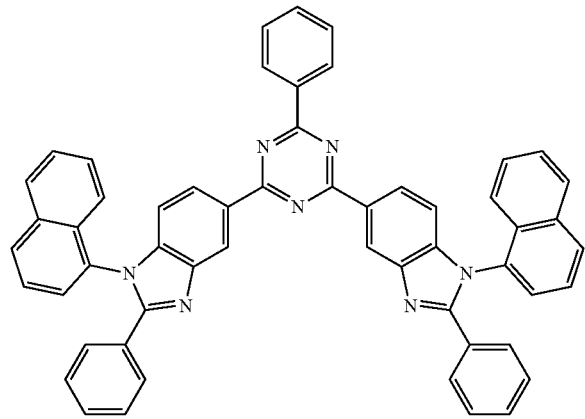
(70)
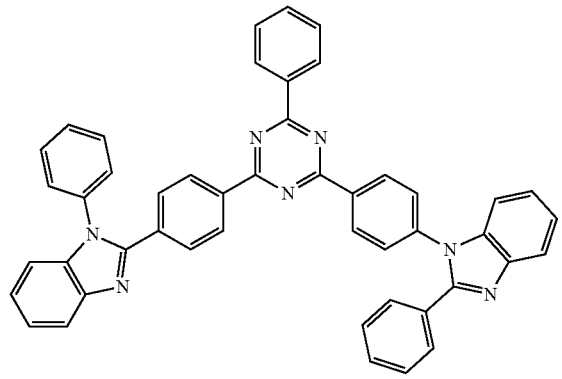
(71)
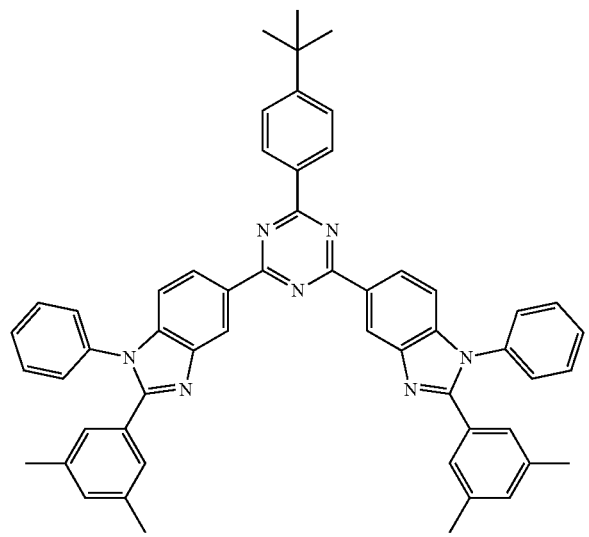
(72)
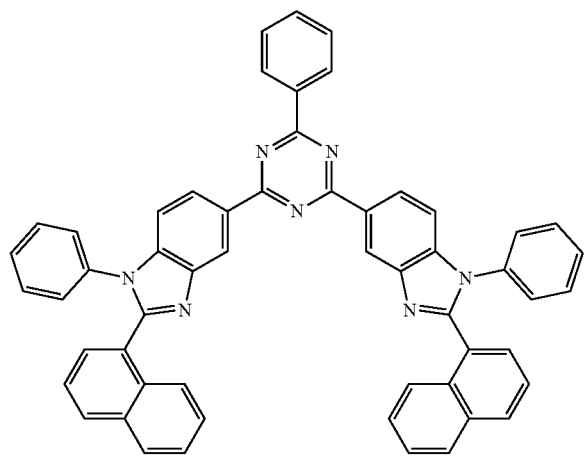
(73)
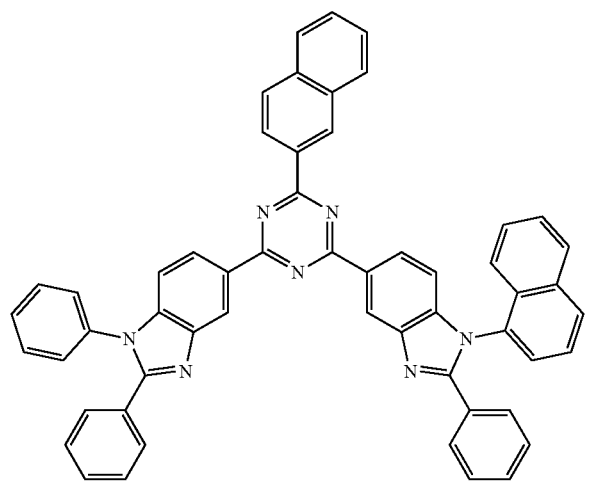
(74)
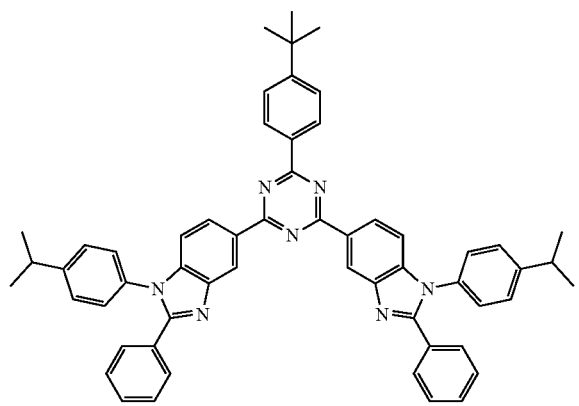

-continued
(75) 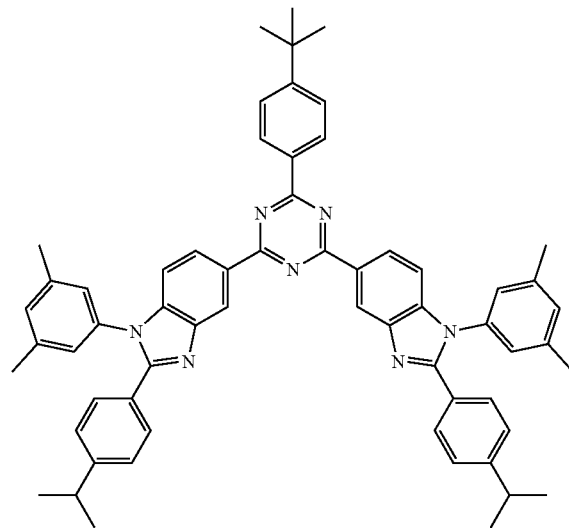
(76) 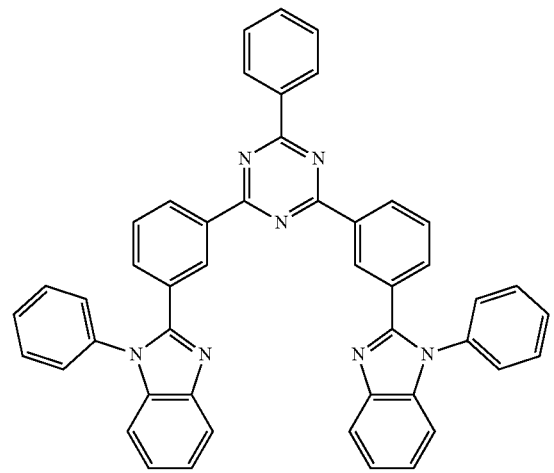
(77) 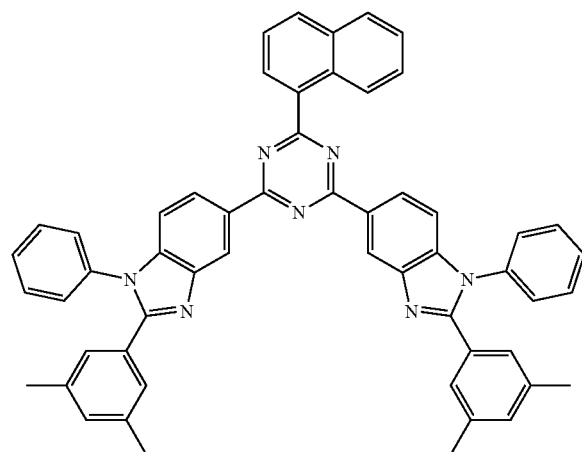
(78) 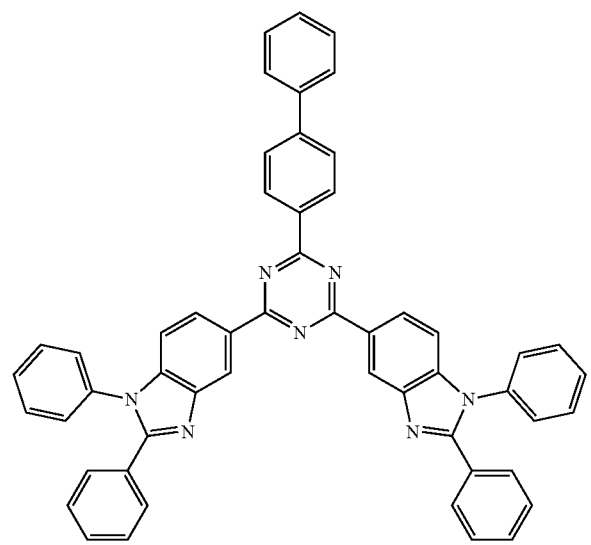
(79) 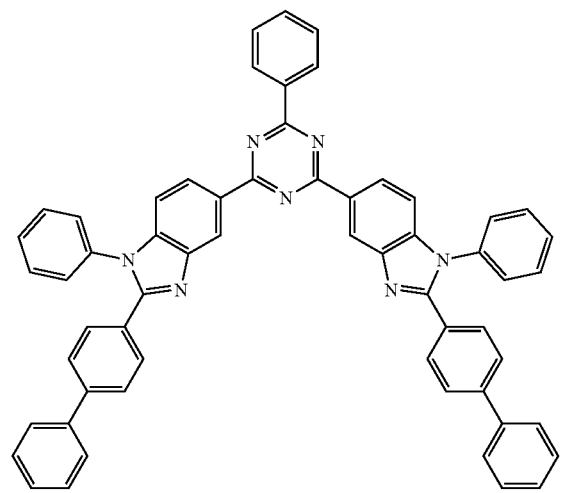
(80) 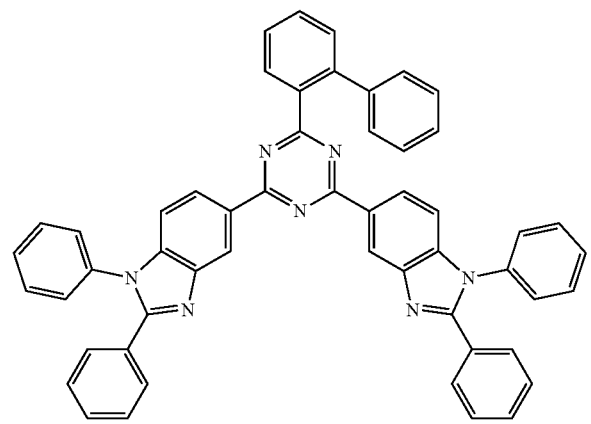

(81)
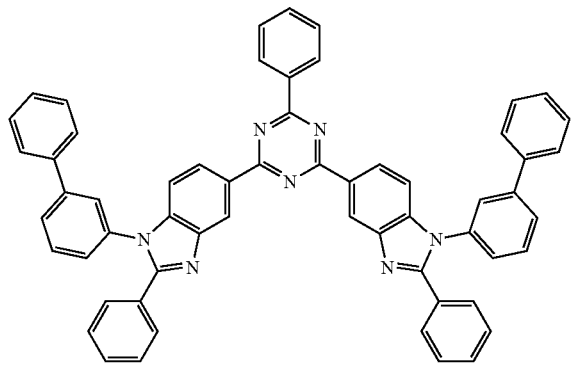
(82)
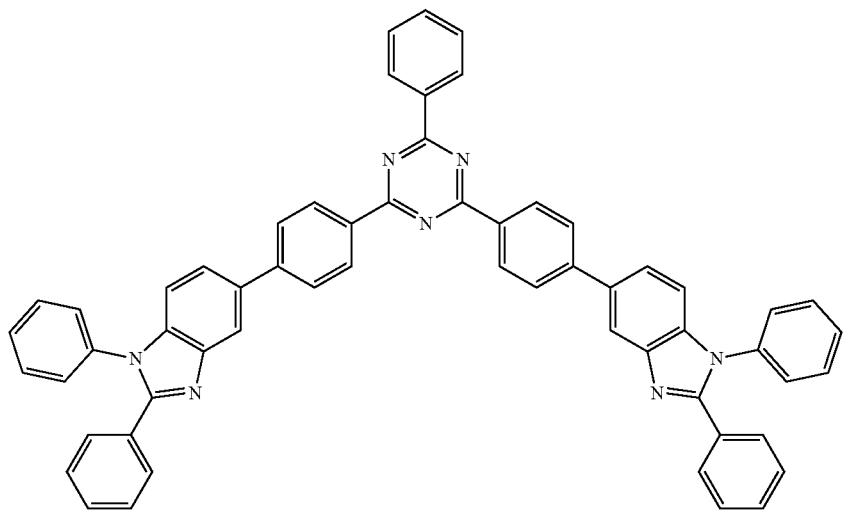
(83)
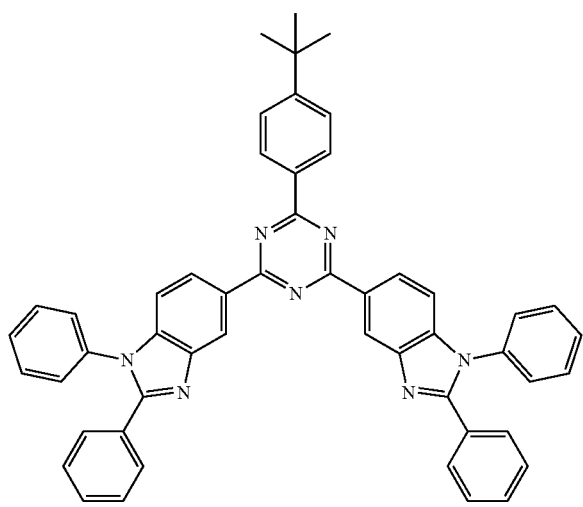
(84)
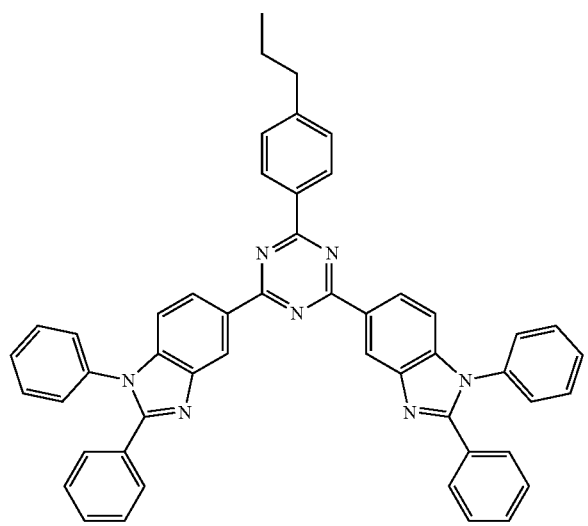

-continued
(85)
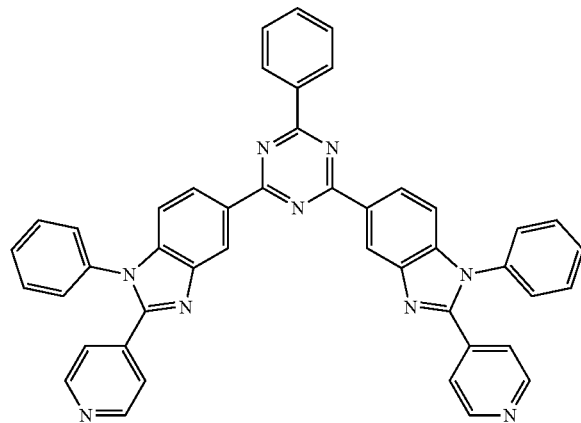
(86)
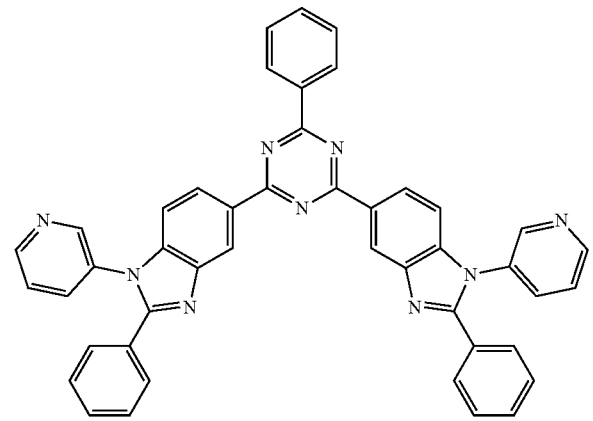
(87)
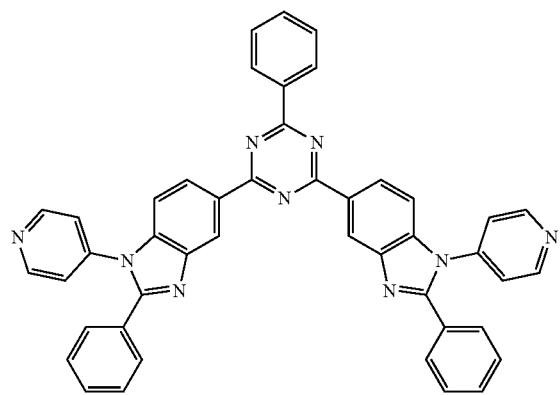
(88)
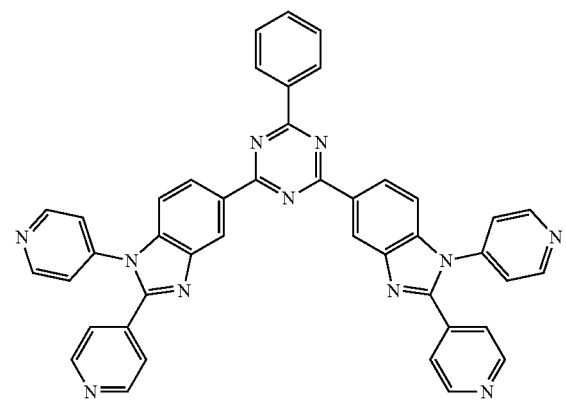
(89)
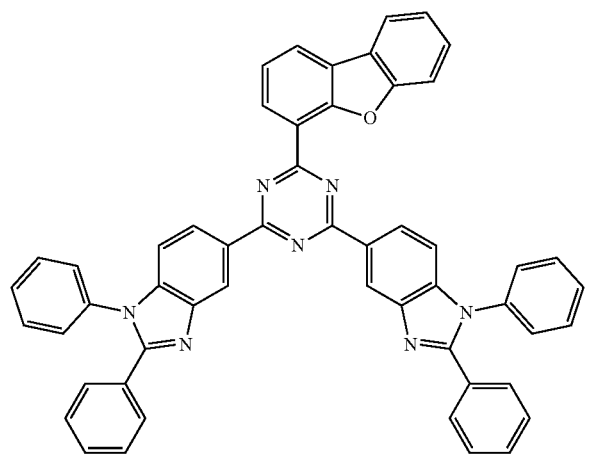
(90)
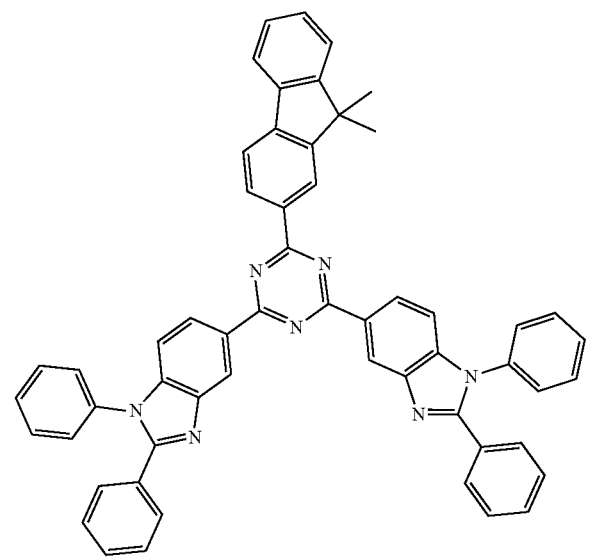

-continued
(91)
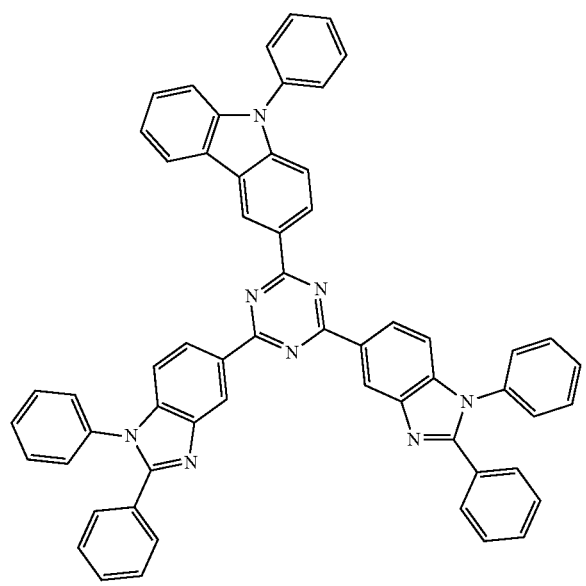
(92)
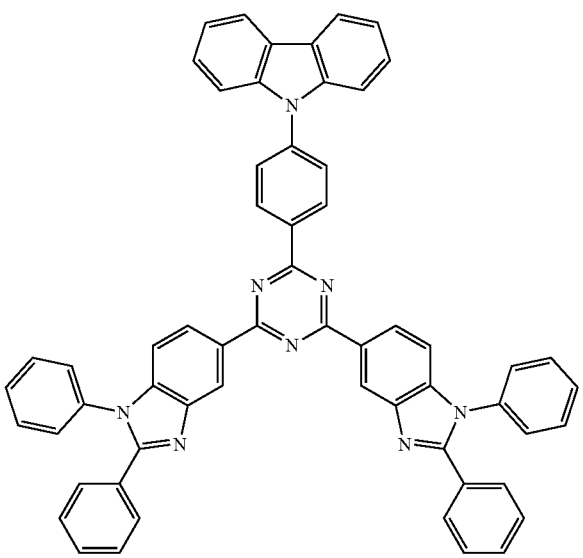
(93)
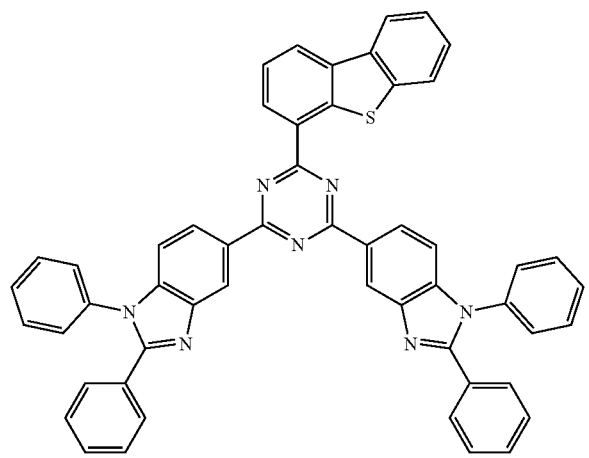
(94)
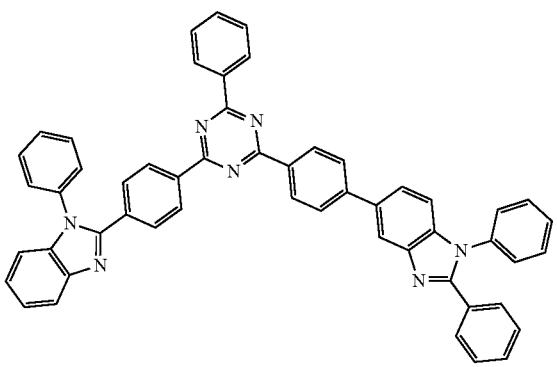

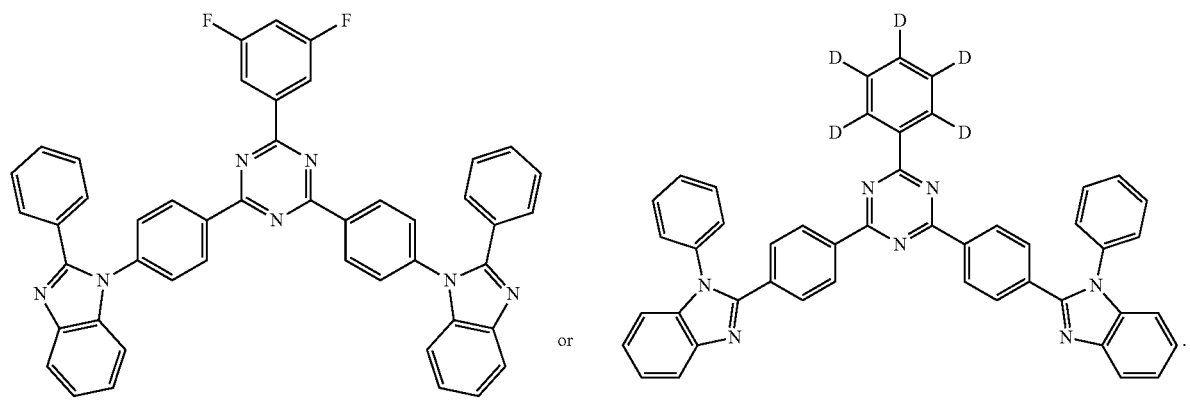

The applicant further provides a preparation method of the organic compound, and reaction equations occurring in the preparation process are as follows:

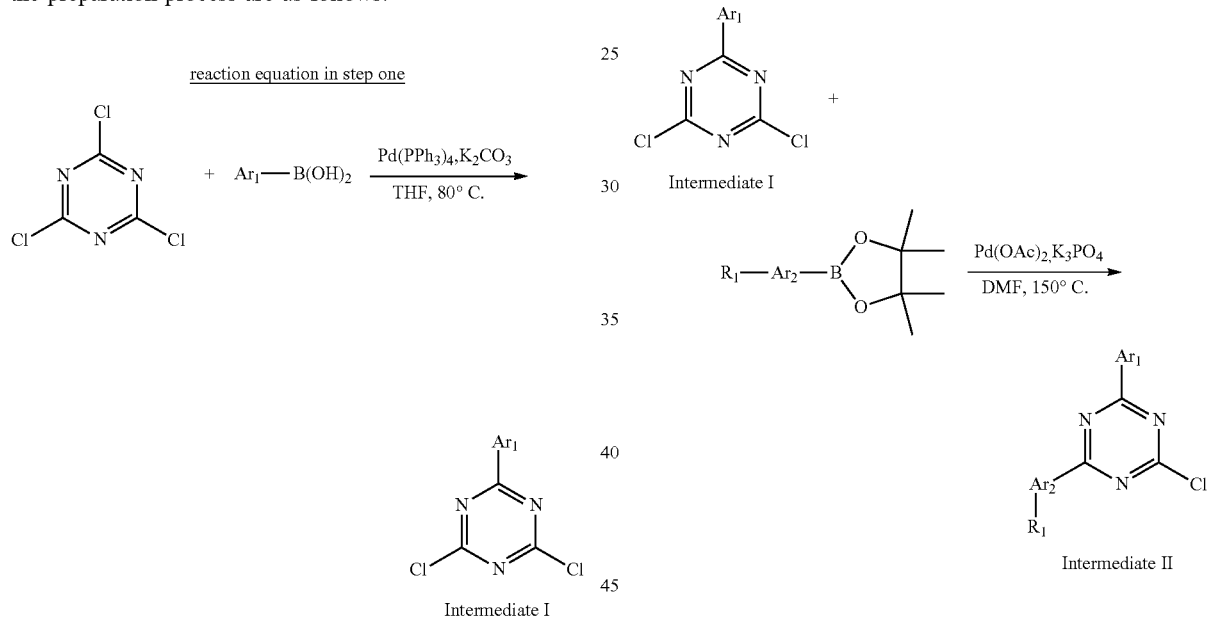

the reaction process particularly is:

step one: in a nitrogen atmosphere, weighing and dissolving a raw material, 2,4,6-trichloro-1,3,5-triazine in tetrahydrofuran, then, adding a boronic acid compound of $Ar_1$ and tetrakis(triphenylphosphine)palladium, stirring the mixture and then adding a saturated aqueous potassium carbonate solution, heating and refluxing a mixed solution containing the above reactants for 10-20 hours at a reaction temperature of 70 to 90° C.; after completion of the reaction, cooling and extracting the mixed solution with dichloromethane, drying the extract over anhydrous sodium sulfate and concentrating under a reduced pressure, and purifying the concentrated solid using a silica gel column to obtain a compound intermediate I; the molar ratio of 2,4,6-trichloro-1,3,5-triazine to $Ar_1$—$B(OH)_2$ is 1:1.0~1.5, the molar ratio of $Pd(PPh_3)_4$ to 2,4,6-trichloro-1,3,5-triazine is 0.005~0.05:1, the molar ratio of $K_2CO_3$ to 2,4,6-trichloro-1,3,5-triazine is 1.0~2.0:1, the dosage of THF is: 2,4,6-trichloro-1,3,5-triazine: THF=1 g: 10~20 ml;

step two: in a nitrogen atmosphere, weighing and dissolving the intermediate I in N,N-dimethylformamide, then adding

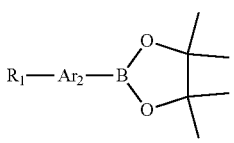

and palladium acetate, stirring the mixture and then adding an aqueous potassium phosphate solution, heating and refluxing a mixed solution containing the above reactants for 10-24 hours at a reaction temperature of 120 to 150° C.; after completion of the reaction, cooling, adding water, filtering and drying the mixture in a vacuum drying oven, and purifying the obtained residue using a silica gel column to obtain a compound intermediate II;

wherein, the molar ratio of the intermediate I to

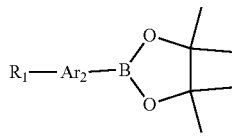

is 1:1.0~1.5, the molar ratio of Pd(OAc)$_2$ to the intermediate I is 0.001~0.02:1, the molar ratio of K$_3$PO$_4$ to the intermediate I is 1.0~2.0:1, the dosage of DMF is: the intermediate I: DMF=1 g: 10~20 ml;

reaction equation in step three

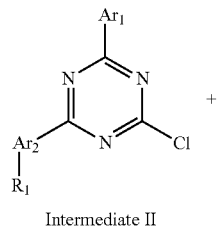

Intermediate II

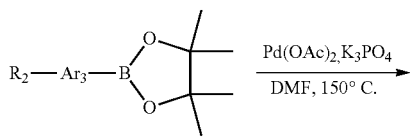

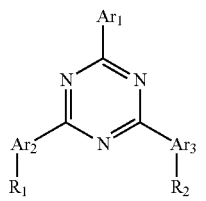

step three: in a nitrogen atmosphere, weighing and dissolving the intermediate II in N,N-dimethylformamide, then adding

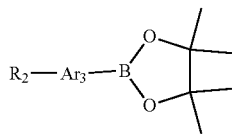

and palladium acetate, stirring the mixture and then adding an aqueous potassium phosphate solution, heating and refluxing a mixed solution containing the above reactants for 10-24 hours at a reaction temperature of 120 to 150° C.; after completion of the reaction, cooling, adding water, filtering and drying the mixture in a vacuum drying oven, and purifying the obtained residue a silica gel column to obtain a target compound;

wherein, the molar ratio of the intermediate II to

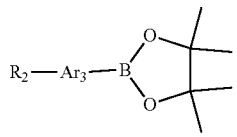

is 1:1.0~1.5, the molar ratio of Pd(OAc)$_2$ to the intermediate II is 0.001~0.02:1, the molar ratio of K$_3$PO$_4$ to the intermediate II is 1.0~2.0:1, the dosage of DMF is: the intermediate II: DMF=1 g: 15~30 ml.

The applicant further provides an application method of the organic compound in preparing an organic electroluminescent device.

The applicant further provides an organic electroluminescent device, including at least one functional layer containing the organic compound with triazine and benzimidazole as the core.

The applicant further provides an organic electroluminescent device including a hole block layer or an electron transport layer, wherein, the hole block layer or the electron transport layer contains the organic compound with triazine and benzimidazole as the core.

The applicant further provides an organic electroluminescent device including a CPL layer, i.e., a light extraction layer, and the CPL layer contains the organic compound with triazine and benzimidazole as the core.

The applicant further provides a lighting or display element, including the organic electroluminescent device.

The present invention achieves the following beneficial effects:

The structure of the organic compound of the present invention contains two rigid groups of triazine and benzimidazole, and the structural stability of the material is improved; the material of the present invention has a molecular weight between 700 and 850, in a spatial structure of the triazine, 4- and 6-positions are strong electron benzimidazoyl groups, 2-position is separated by a hole group, so that the material has a higher density and achieves a higher refractive index; the material is low in absorption and high in refractive index in the field of visible light; meanwhile, the material of the present invention has a relatively high glass transition temperature and molecular thermal stability; the evaporation temperature of the material with a molecular weight between 700 and 850 is generally less than 350° C. in a vacuum state, ensuring that the material does not decompose during the long-time evaporation in the mass production process, and reduces the influence on the deformation of the evaporation MASK due to the heat radiation of the evaporation temperature.

The material of the present invention is applied to the CPL layer of the OLED device, doesn't participate in the electron and hole transmission of the device, but is subjected to very high requirements on thermal stability, film crystallinity and light transmission (high refractive index). As described above, the triazine and benzimidazole are rigid groups, so that the stability of the material is improved; the high Tg temperature ensures that the material does not crystallize in the film state; the low evaporation temperature is the premise that the material can be applied to mass production; the high refractive index is the most major factor that the material of the present invention can be applied to a CPL layer.

With a deep HOMO energy level and a high electron mobility, the material of the present invention can effectively block holes/energy from transmitting from a light-emitting layer to the electron layer, so that the recombination efficiency of the hole and the electron in the light-emitting layer can be improved, thus the light-emitting efficiency of the OLED device can be enhanced and the service life of the OLED device can be prolonged. The present invention can effectively improve the light extraction efficiency of the OLED device when applied to the CPL layer of the OLED device. To sum up, the compound of the present invention has a good application effect and industrialization prospect in an OLED light-emitting device.

DETAILED DESCRIPTION OF THE INVENTION

Example 1: Synthesis of Intermediate I

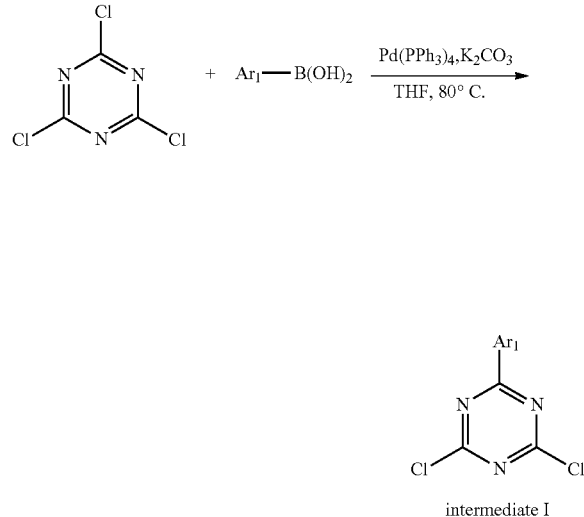

Figure 1:
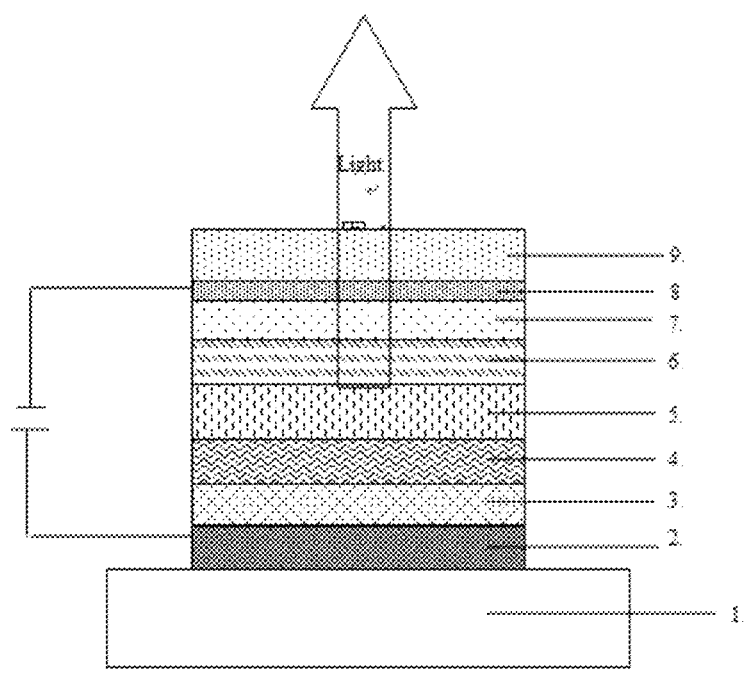
FIG. 1 is a schematic structural diagram when materials set forth in the present invention are applied to an OLED device; wherein, 1, an OLED device substrate, 2, an anode layer, 3, a hole injection layer, 4, a hole transport layer, 5, a light-emitting layer, 6, a hole block layer or an electron transport layer, 7, an electron injection layer, 8, a cathode layer, and 9, a CPL layer.

intermediate I in a nitrogen atmosphere, a raw material, 2,4,6-trichloro-1,3,5-triazine was weighed and dissolved in tetrahydrofuran, then, a boronic acid compound of $Ar_1$ and tetrakis(triphenylphosphine)palladium were added, the mixture was stirred and then a saturated aqueous potassium carbonate solution was added, a mixed solution containing the above reactants was heated and refluxed for 10-20 hours at a reaction temperature of 70 to 90° C.; after completion of the reaction, the mixed solution was cooled and extracted with dichloromethane, the extract was dried over anhydrous sodium sulfate and concentrated under a reduced pressure, the concentrated solid was purified using a silica gel column to obtain a compound intermediate I;

the molar ratio of 2,4,6-trichloro-1,3,5-triazine to $Ar_1$—$B(OH)_2$ was 1:1.0~1.5, the molar ratio of $Pd(PPh_3)_4$ to 2,4,6-trichloro-1,3,5-triazine was 0.005~0.05:1, the molar ratio of $K_2CO_3$ to 2,4,6-trichloro-1,3,5-triazine was 1.0~2.0:1, the dosage of THF was: 2,4,6-trichloro-1,3,5-triazine:THF=1 g: 10~20 ml;

Taking synthesis of an intermediate A1 as an example:

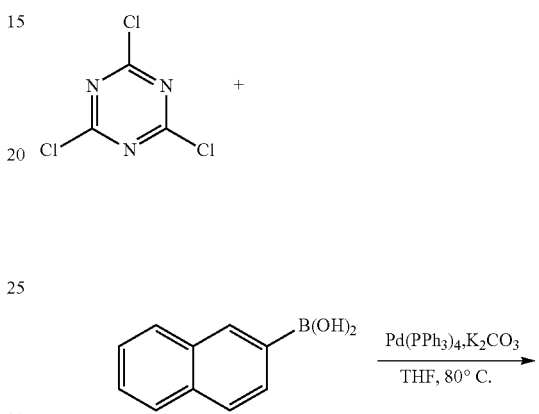

In a 250 ml three-necked flask, nitrogen gas was introduced, 0.04 mol of raw material, 2,4,6-trichloro-1,3,5-triazine, 100 ml of THF, 0.05 mol of 2-naphthalene boronic acid, 0.0004 mol of tetrakis(triphenylphosphine)palladium were added, the mixture was stirred and then 0.06 mol of $K_2CO_3$ aqueous solution (2M) was added, the mixed solution was heated to 80° C. and refluxed for 15 hours, sampled and spotted until completion of the reaction. The mixed solution was cooled naturally, extracted with 200 ml of dichloromethane, and the layers were separated, the extract liquid was dried over anhydrous sodium sulfate, and filtered, the filtrate was rotarily evaporated, and purified using a silica gel column to obtain an intermediate A1, the purity of HPLC was 99.5%, and the yield was 82.8%.

Elemental analysis structure (molecular formula $C_{13}H_7Cl_2N_3$): theoretical values C, 56.55; H, 2.56; Cl, 25.68; N, 15.22; test values: C, 56.56; H, 2.58; Cl, 25.65; N, 15.21. ESI-MS (m/z)(M+): the theoretical value was 275.00, the measured value was 275.27.

The intermediate I was prepared by the synthetic method of the intermediate A1, and particular structures were as shown in Table 1.

TABLE 1
| Raw material 1 | Raw material 2 | Intermediate I |
|---|---|---|
| 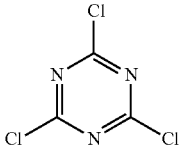 | 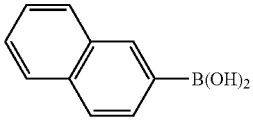 [SMILES: OB(O)c1ccc2ccccc2c1] | 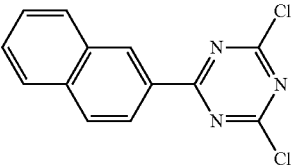<br>Intermediate A1 |
| 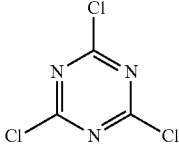 | 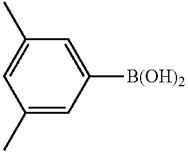 | 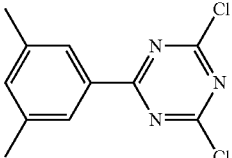<br>Intermediate A2 |
| 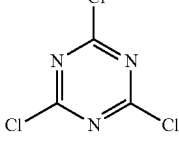 | 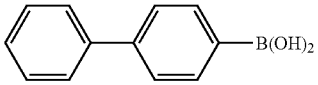 | 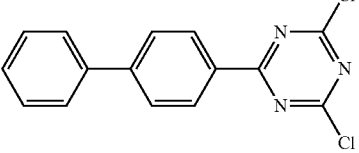<br>Intermediate A3 |
| 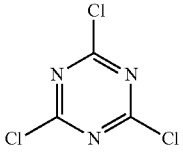 | 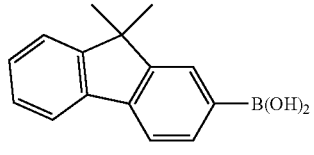 [SMILES: CC1(C)c2ccccc2-c2ccc(B(O)O)cc21] | 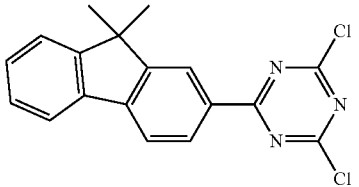<br>Intermediate A5 |
| 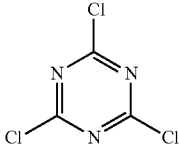 | 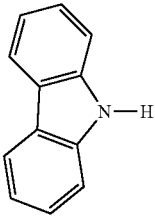 [SMILES: c1ccc2c(c1)[nH]c1ccccc12] | 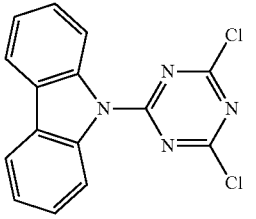<br>Intermediate A6 |
| 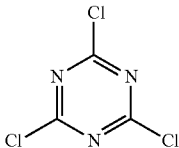 | 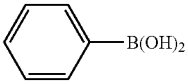 | 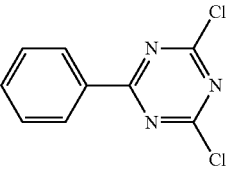<br>Intermediate A7 |

TABLE 1-continued

| Raw material 1 | Raw material 2 | Intermediate I |
| --- | --- | --- |
| cyanuric chloride | biphenyl-3-boronic acid | Intermediate A8 |
| cyanuric chloride | 9-phenyl-9H-carbazol-3-boronic acid | Intermediate A9 |
| cyanuric chloride | 4-tert-butylphenylboronic acid | Intermediate A10 |
| cyanuric chloride | 4-(9H-carbazol-9-yl)phenylboronic acid | Intermediate A11 |
| cyanuric chloride | dibenzofuran-4-boronic acid | |

Example 2: Synthesis of Intermediate

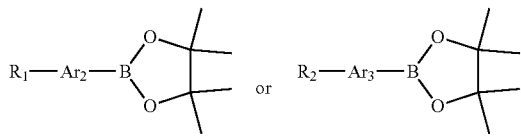

when Ar$_2$ or Ar$_3$ represents a structure represented by formula (2),

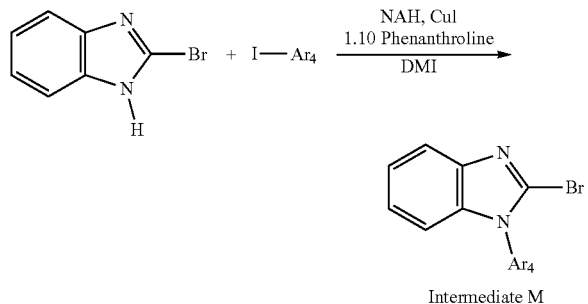

(1) In a 250 ml three-necked flask, nitrogen gas was introduced, 0.02 mol of raw material, 2-bromo-benzimidazole, 0.03 mol of iodobenzene, 0.04 mol of sodium hydride, 0.004 mol of cuprous iodide and 0.01 mol of phenanthroline were added and dissolved in 100 ml of 1,3-dimethyl-2-imidazolidinone, the reaction was performed by stirring for 20-30 hours, after completion of the reaction, water was added and the mixture was extracted with dichloromethane, the organic layer was dried over anhydrous sodium sulfate, eluted using a 1:100 by volume mixture of petroleum ether and ethyl acetate as the eluent, and purified by column chromatography to obtain an intermediate M;

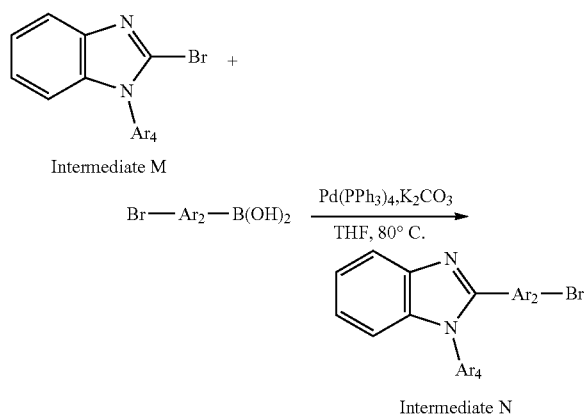

(2) in a nitrogen atmosphere, the intermediate M was weighed and dissolved in tetrahydrofuran, then, and tetrakis(triphenylphosphine)palladium were added, the mixture was stirred and then a saturated aqueous potassium carbonate solution was added, a mixed solution containing the above reactants was heated and refluxed for 10-20 hours at a reaction temperature of 70 to 90° C.; after completion of the reaction, the mixed solution was cooled and extracted with dichloromethane, the extract was dried over anhydrous sodium sulfate and concentrated under a reduced pressure, the concentrated solid was purified using a silica gel column to obtain a compound intermediate N;

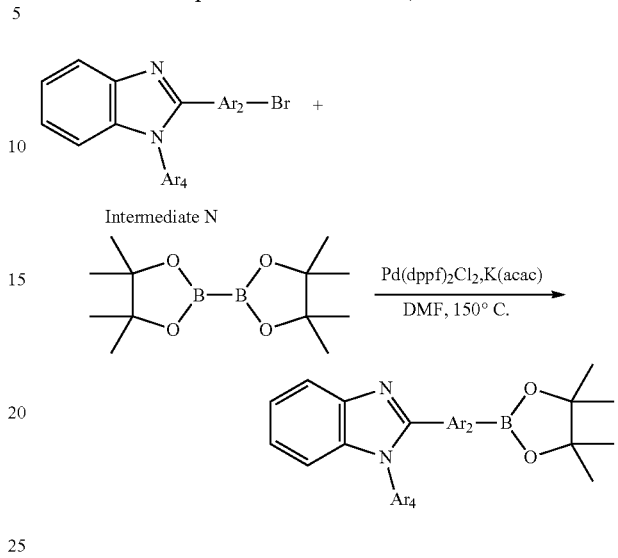

(3) in a nitrogen atmosphere, the intermediate N was weighed and dissolved in N,N-dimethylformamide (DMF), then bis(pinacolato)diboron, [1,1'-bis(diphenylphosphino)-ferrocene]dichloropalladium (II) and potassium acetate were added, the mixture was stirred, a mixed solution containing the above reactants was heated and refluxed for 5-10 hours at a reaction temperature of 120 to 150° C.; after completion of the reaction, the mixture was cooled, filtered and dried in a vacuum drying oven. The obtained residue was separated and purified using silica gel column obtain a compound intermediate IV;

when Ar$_2$ or Ar$_3$ represents a structure represented by formula (3),

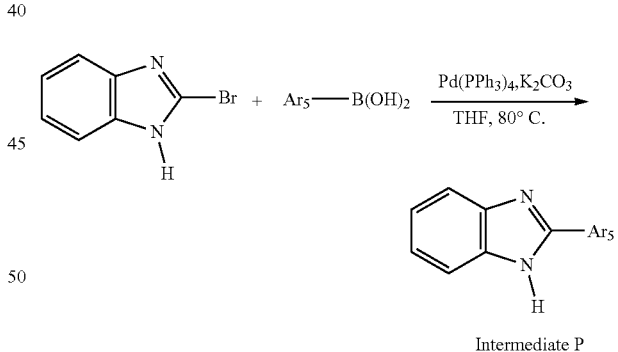

(1) in a nitrogen atmosphere, 2-bromo-benzimidazole was weighed and dissolved in tetrahydrofuran, then, A$_5$—B(OH)$_2$ and tetrakis(triphenylphosphine)palladium were added, the mixture was stirred and then a saturated aqueous potassium carbonate solution was added, a mixed solution containing the above reactants was heated and refluxed for 5-15 hours at a reaction temperature of 70 to 90° C.; after completion of the reaction, the mixed solution was cooled and extracted with dichloromethane, the extract was dried over anhydrous sodium sulfate and concentrated under a reduced pressure, the concentrated solid was purified using a silica gel column to obtain a compound intermediate P;

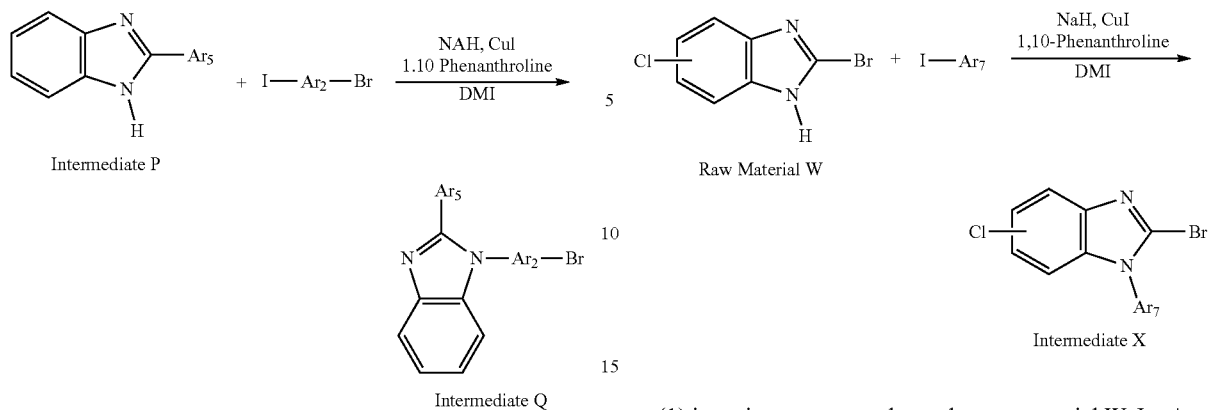

Intermediate P

Intermediate Q

Raw Material W

Intermediate X (1) in a nitrogen atmosphere, the raw material W, I—Ar$_7$, sodium hydride, cuprous iodide and phenanthroline were added and dissolved in 1,3-dimethyl-2-imidazolidinone, the reaction was performed by stirring for 20-30 hours, after completion of the reaction, water was added and the mixture was extracted with dichloromethane, the organic layer was dried over anhydrous sodium sulfate, eluted using a mixture of petroleum ether and ethyl acetate as the eluent, and purified by column chromatography to obtain an intermediate X;

(2) in a nitrogen atmosphere, the intermediate P, I—Ar$_2$—Br, sodium hydride, cuprous iodide and phenanthroline were added and dissolved in 1,3-dimethyl-2-imidazolidinone, the reaction was performed by stirring for 20-30 hours, after completion of the reaction, water was added and the mixture was extracted with dichloromethane, the organic layer was dried over anhydrous sodium sulfate, eluted using a mixture of petroleum ether and ethyl acetate as the eluent, and purified by column chromatography to obtain an intermediate Q;

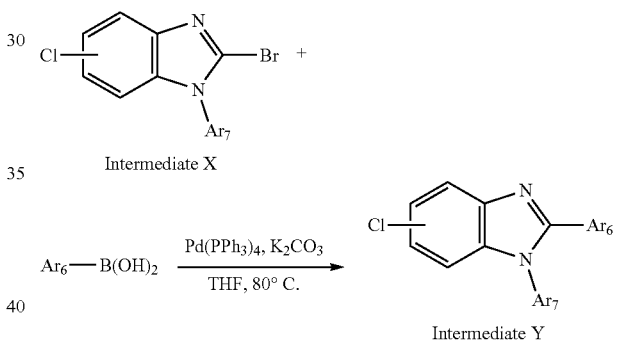

Intermediate X

Intermediate Y

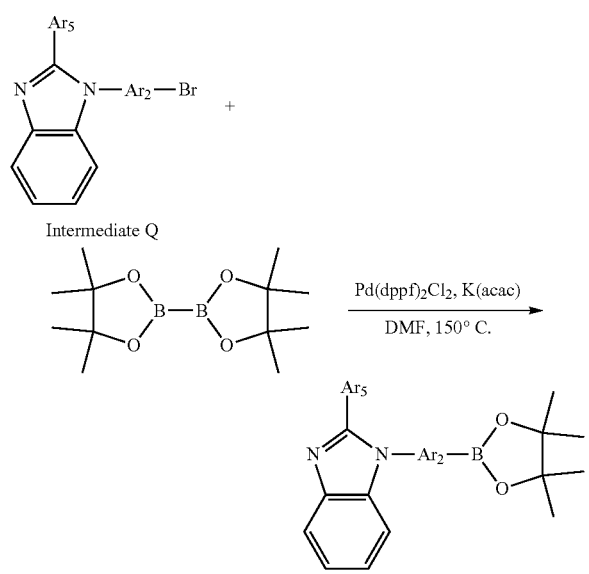

Intermediate Q (3) in a nitrogen atmosphere, the intermediate Q was weighed and dissolved in N,N-dimethylformamide (DMF), then bis(pinacolato)diboron, [1,1'-bis(diphenylphosphino)-ferrocene]dichloropalladium (II) and potassium acetate were added, the mixture was stirred, a mixed solution containing the above reactants was heated and refluxed for 5-10 hours at a reaction temperature of 120 to 150° C.; after completion of the reaction, the mixture was cooled, filtered and dried in a vacuum drying oven. The obtained residue was separated and purified using silica gel column obtain a compound intermediate IV;

when Ar$_2$ or Ar$_3$ represents a structure represented by formula (4), (2) in a nitrogen atmosphere, an intermediate X was weighed and dissolved in tetrahydrofuran, then, Ar$_6$—B(OH)$_2$ and tetrakis(triphenylphosphine)palladium were added, the mixture was stirred and then a saturated aqueous potassium carbonate solution was added, a mixed solution containing the above reactants was heated and refluxed for 5-15 hours at a reaction temperature of 70 to 90° C.; after completion of the reaction, the mixed solution was cooled and extracted with dichloromethane, the extract was dried over anhydrous sodium sulfate and concentrated under a reduced pressure, the concentrated solid was purified using a silica gel column to obtain a compound intermediate Y;

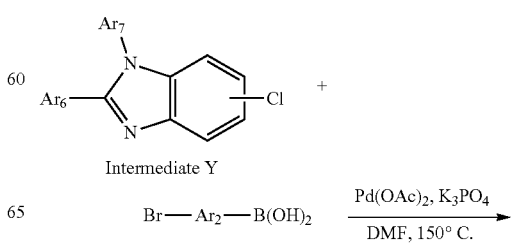

Intermediate Y

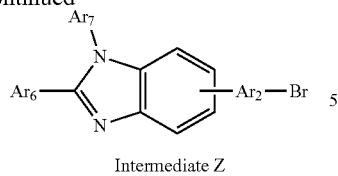

Intermediate Z (3) in a nitrogen atmosphere, the intermediate Y was weighed and dissolved in N,N-dimethylformamide, then Br—Ar$_2$—B(OH)$_2$ and palladium acetate were added, the mixture was stirred and then an aqueous potassium phosphate solution was added, a mixed solution containing the above reactants was heated and refluxed for 10-24 hours at a reaction temperature of 120 to 150° C.; after completion of the reaction, cooling, water was added, the mixture was filtered and dried in a vacuum drying oven, and the obtained residue is purified using a silica gel column to obtain a compound intermediate Z.

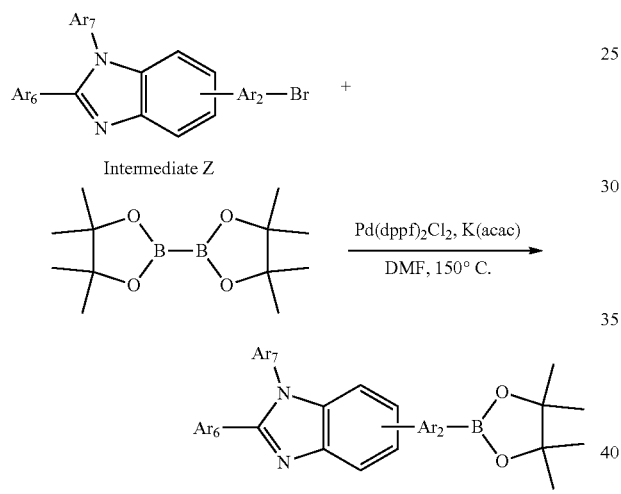

(4) in a nitrogen atmosphere, the intermediate Z was weighed and dissolved in N,N-dimethylformamide (DMF), then bis(pinacolato)diboron, [1,1'-bis(diphenylphosphino)-ferrocene]dichloropalladium (II) and palladium acetate were added, the mixture was stirred, a mixed solution containing the above reactants was heated and refluxed for 5-10 hours at a reaction temperature of 120 to 150° C.; after completion of the reaction, the mixture was cooled, filtered and dried in a vacuum drying oven. The obtained residue is purified using a silica gel column to obtain a compound intermediate IV;

Taking synthesis of an intermediate B7 as an example:

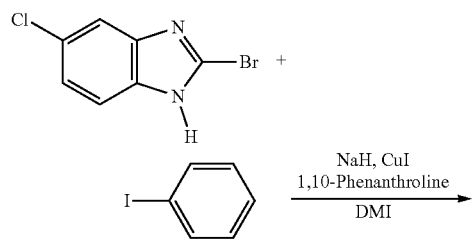

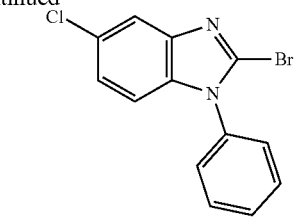

Intermediate X1

(1) In a 250 ml three-necked flask, nitrogen gas was introduced, 0.02 mol of raw material, 2-bromo-5-chloro-1H-benzimidazole, 0.03 mol of iodobenzene, 0.04 mol of sodium hydride, 0.004 mol of cuprous iodide and 0.01 mol of phenanthroline were added and dissolved in 100 ml of 1,3-dimethyl-2-imidazolidinone, the reaction was performed by stirring for 20-30 hours, after completion of the reaction, water was added and the mixture was extracted with dichloromethane, the organic layer was dried over anhydrous sodium sulfate, eluted using a 1:100 by volume mixture of petroleum ether and ethyl acetate as the eluent, and purified by column chromatography to obtain an intermediate X1; the purity of HPLC was 99.7%, and the yield was 78.5%.

Elemental analysis structure (molecular formula $C_{13}H_8BrClN_2$): theoretical values C, 50.76; H, 2.62; Br, 25.98; Cl, 11.53; N, 9.11; test values: C, 50.74; H, 2.63; Br, 25.96; Cl, 11.55; N, 9.12. ESI-MS (m/z)(M$^+$): the theoretical value was 305.96, the measured value was 306.24.

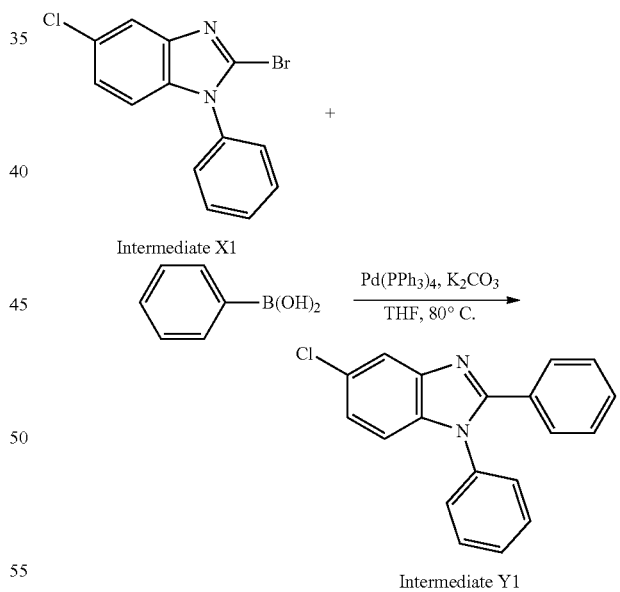

(2) In a 250 ml three-necked flask, nitrogen gas was introduced, 0.04 mol of the intermediate X1, 100 ml of THF, 0.05 mol of phenylboronic acid, 0.0004 mol of tetrakis(triphenylphosphine)palladium were added, the mixture was stirred and then 0.06 mol of K$_2$CO$_3$ aqueous solution (2M) was added, the mixed solution was heated to 80° C. and refluxed for 10 hours, sampled and spotted until completion of the reaction. The mixed solution was cooled naturally, extracted with 200 ml of dichloromethane, and the layers were separated, the extract liquid was dried over anhydrous sodium sulfate, and filtered, the filtrate was rotarily evaporated, and purified using a silica gel column to obtain an intermediate Y1, the purity of HPLC was 99.8%, and the yield was 88.2%.

Elemental analysis structure (molecular formula $C_{19}H_{13}ClN_2$): theoretical values C, 74.88; H, 4.30; Cl, 11.63; N, 9.19; test values: C, 74.84; H, 4.33; Cl, 11.65; N, 9.18. ESI-MS (m/z)(M$^+$): the theoretical value was 304.08, the measured value was 304.52.

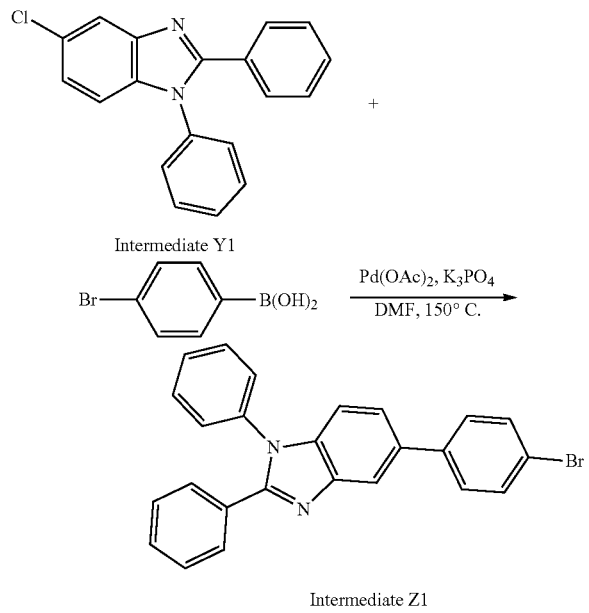

(3) In a 250 ml three-necked flask, nitrogen gas was introduced, 0.02 mol of the intermediate Y1, 120 ml of DMF, 0.04 mol of phenylboronic acid, 0.0002 mol of palladium acetate were added, the mixture was stirred and then 0.02 mol of K$_3$PO$_4$ aqueous solution was added, the mixed solution was heated to 130° C. and refluxed for 10 hours, sampled and spotted until completion of the reaction. The mixed solution was cooled naturally, extracted with 200 ml of dichloromethane, and the layers were separated, the extract liquid was dried over anhydrous sodium sulfate, and filtered, the filtrate was rotarily evaporated, and purified using a silica gel column to obtain an intermediate Z1, the purity of HPLC was 99.5%, and the yield was 80.5%.

Elemental analysis structure (molecular formula $C_{25}H_{17}BrN_2$): theoretical values C, 70.60; H, 4.03; Br, 18.79; N, 6.59; test values: C, 70.60; H, 4.05; Br, 18.78; N, 6.57. ESI-MS (m/z)(M$^+$): the theoretical value was 424.06, the measured value was 424.34.

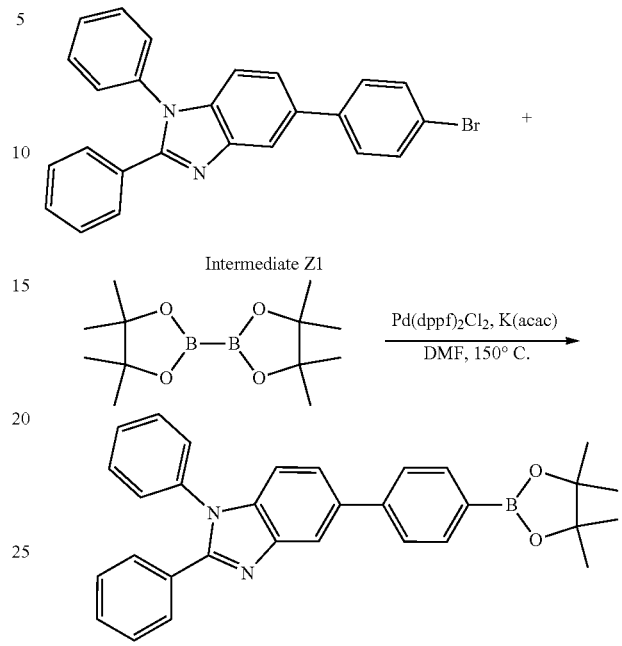

(4) In a 500 ml three-necked flask, nitrogen gas was introduced, 0.05 mol of the intermediate Z1 was added and dissolved in 300 ml of N,N-dimethylformamide (DMF), then 0.06 mol of bis(pinacolato)diboron, 0.0005 mol of [1,1'-bis(diphenylphosphino)-ferrocene]dichloropalladium (II) and 0.125 mol of potassium acetate were added, the mixture was stirred, a mixed solution containing the above reactants was heated and refluxed for 10 hours at a reaction temperature of 120 to 150° C.; after completion of the reaction, cooling, 200 ml of water was added, the mixture was filtered and dried in a vacuum drying oven. The obtained residue was separated and purified using silica gel column obtain a compound intermediate B7; the purity of HPLC was 99.2%, and the yield was 81.2%. Elemental analysis structure (molecular formula $C_{31}H_{29}BN_2O_2$: theoretical values C, 78.82; H, 6.19; B, 2.29; N, 5.93; 0, 6.77; test values: C, 78.92; H, 6.14; B, 2.25; N, 5.94; 0, 6.75. ESI-MS (m/z)(M$^+$): the theoretical value was 472.23, the measured value was 472.59. The intermediate IV was prepared by the synthetic method of the intermediate B7, and particular structures were as shown in Table 2.

TABLE 2

| Raw material 4 | Raw material 5 | Raw material 6 | Intermediate IV |
|---|---|---|---|
| 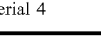 |  |  |  Intermediate B1 |

TABLE 2-continued

| Raw material 4 | Raw material 5 | Raw material 6 | Intermediate IV |
|---|---|---|---|
| 2-bromo-1H-benzimidazole | 1-iodo-4-isopropylbenzene | 4-bromophenylboronic acid | Intermediate B2 |
| 2-bromo-1H-benzimidazole | 1-bromo-4-iodobenzene | phenylboronic acid | Intermediate B3 |
| 2-bromo-1H-benzimidazole | 1-bromo-4-iodobenzene | 4-isopropylphenylboronic acid | Intermediate B4 |
| 2-bromo-5-chloro-1H-benzimidazole | iodobenzene | phenylboronic acid | Intermediate B5 |
| 2-bromo-1H-benzimidazole | iodobenzene | 3-bromophenylboronic acid | Intermediate B6 |
| 2-bromo-5-chloro-1H-benzimidazole | iodobenzene | phenylboronic acid + 1,4-phenyldiboronic acid | Intermediate B7 |

TABLE 2-continued

| Raw material 4 | Raw material 5 | Raw material 6 | Intermediate IV |
|---|---|---|---|
| 2-bromo-benzimidazole | 4-iodopyridine | 4-bromophenylboronic acid | Intermediate B8 |
| 2-bromo-benzimidazole | iodobenzene | 3-bromo-3'-boronic acid biphenyl | (structure shown) |
| 2-bromo-benzimidazole | 2-iodonaphthalene | 4-bromophenylboronic acid | (structure shown) |

Example 3: Synthesis of Compound 1

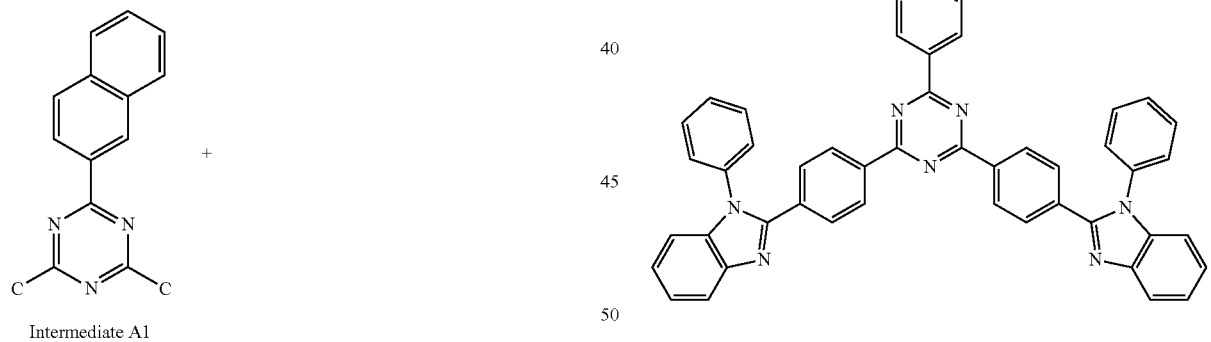

In a 250 ml three-necked flask, nitrogen gas was introduced, 0.01 mol of the intermediate A1, 150 ml of DMF, 0.03 mol of the intermediate B1, 0.0002 mol of palladium acetate were added, the mixture was stirred and then 0.02 mol of $K_3PO_4$ aqueous solution was added, the mixed solution was heated to 150° C. and refluxed for 24 hours, sampled and spotted until completion of the reaction. The mixed solution was cooled naturally, extracted with 200 ml of dichloromethane, and the layers were separated, the extract liquid was dried over anhydrous sodium sulfate, and filtered, the filtrate was rotarily evaporated, and purified using a silica gel column to obtain a target product, the purity of HPLC was 99.1%, and the yield was 72.1%.

Elemental analysis structure (molecular formula $C_{51}H_{33}N_7$): theoretical values C, 82.35; H, 4.47; N, 13.18;

test values: C, 82.37; H, 4.48; N, 13.15. ESI-MS (m/z)(M+): the theoretical value was 743.28, the measured value was 743.62.

Example 4: Synthesis of Compound 10

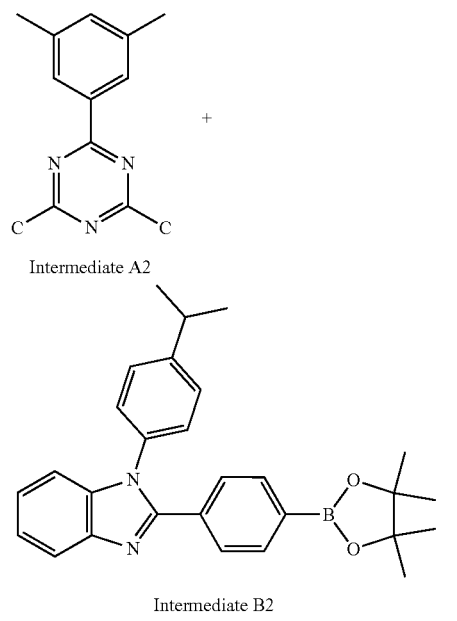

Example 5: Synthesis of Compound 13

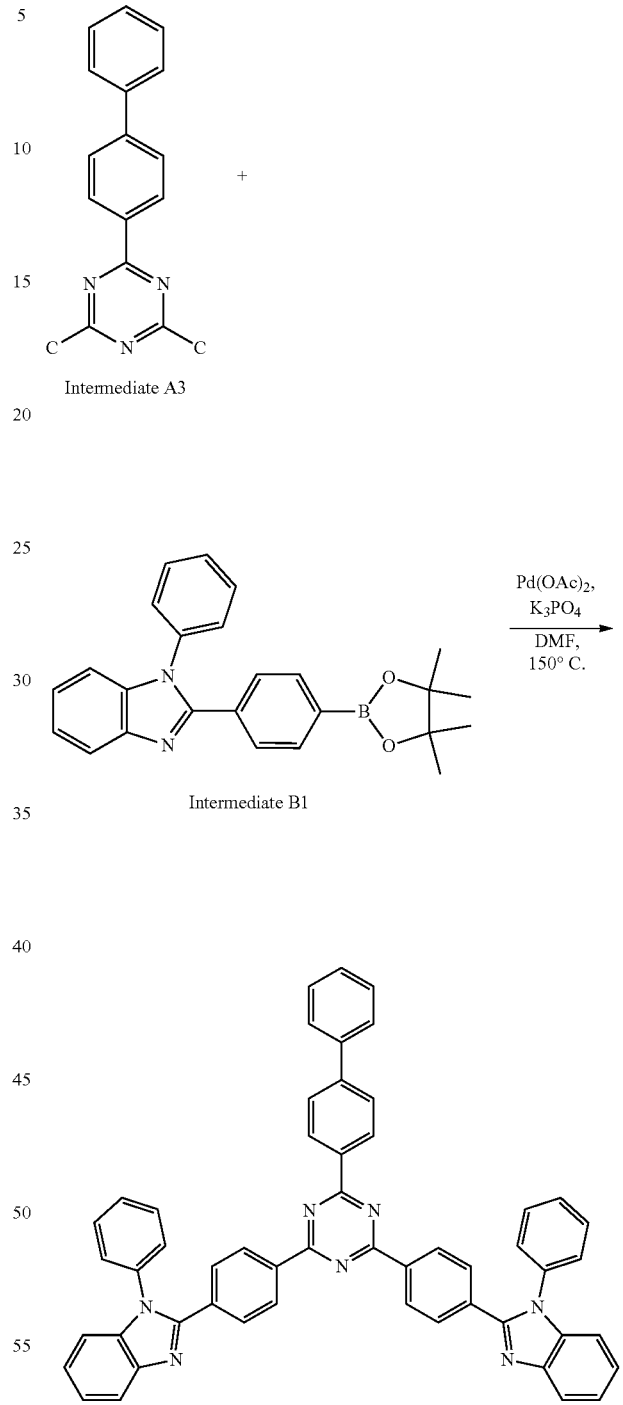

In a 250 ml three-necked flask, nitrogen gas was introduced, 0.01 mol of the intermediate A2, 150 ml of DMF, 0.03 mol of the intermediate B2, 0.0002 mol of palladium acetate were added, the mixture was stirred and then 0.02 mol of $K_3PO_4$ aqueous solution was added, the mixed solution was heated to 150° C. and refluxed for 24 hours, sampled and spotted until completion of the reaction. The mixed solution was cooled naturally, extracted with 200 ml of dichloromethane, and the layers were separated, the extract liquid was dried over anhydrous sodium sulfate, and filtered, the filtrate was rotarily evaporated, and purified using a silica gel column to obtain a target product, the purity of HPLC was 99.3%, and the yield was 75.4%.

Elemental analysis structure (molecular formula $C_{55}H_{47}N_7$): theoretical values C, 81.96; H, 5.88; N, 12.16; test values: C, 81.99; H, 5.86; N, 12.15. ESI-MS (m/z)(M+): the theoretical value was 805.39, the measured value was 805.74.

The preparation method of the compound 13 was the same with that in Example 3, except that the intermediate A1 was replaced with the intermediate A3.

Elemental analysis structure (molecular formula $C_{53}H_{35}N_7$): theoretical values C, 82.68; H, 4.58; N, 12.74; test values: C, 82.68; H, 4.56; N, 12.76. ESI-MS (m/z)(M+): the theoretical value was 769.30, the measured value was 769.67.

Example 6: Synthesis of Compound 19

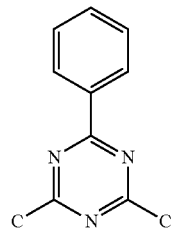

Intermediate A7

+

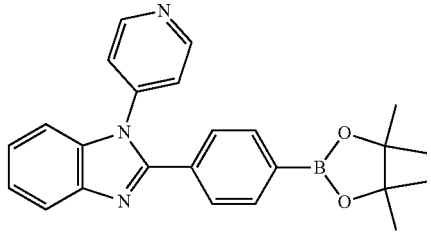

Intermediate B8

$\xrightarrow{\text{Pd(OAc)}_2, \text{K}_3\text{PO}_4, \text{DMF}, 150°\text{C.}}$

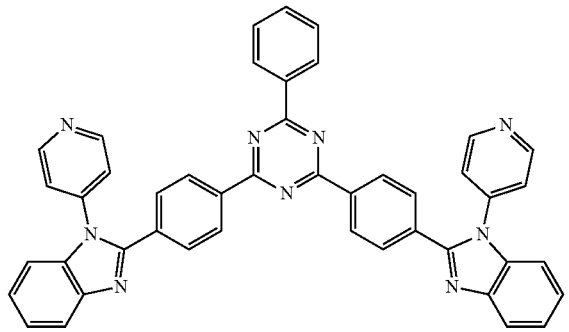

The preparation method of the compound 19 was the same with that in Example 3, except that the intermediate A1 was replaced with the intermediate A7; the intermediate B1 was replaced with the intermediate B8.

Elemental analysis structure (molecular formula $C_{45}H_{29}N_9$): theoretical values C, 77.68; H, 4.20; N, 18.12; test values: C, 77.68; H, 4.20; N, 18.12. ESI-MS (m/z)(M$^+$): the theoretical value was 695.25, the measured value was 695.25.

Example 7: Synthesis of Compound 25

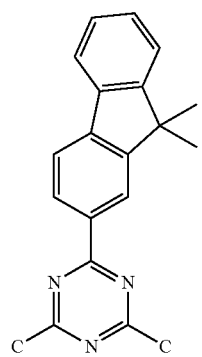

Intermediate A5

+

Intermediate B1

$\xrightarrow{\text{Pd(OAc)}_2, \text{K}_3\text{PO}_4, \text{DMF}, 150°\text{C.}}$

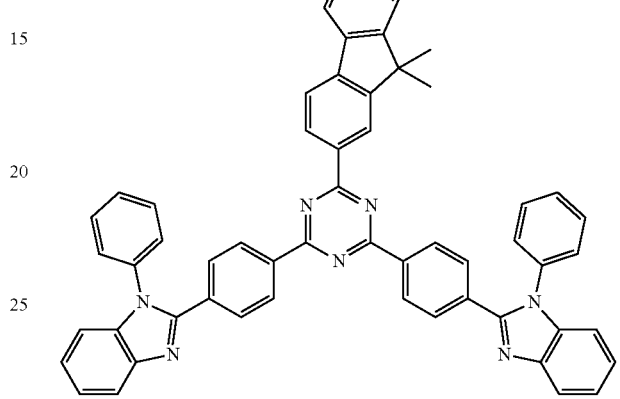

The preparation method of the compound 25 was the same with that in Example 3, except that the intermediate A1 was replaced with the intermediate A5.

Elemental analysis structure (molecular formula $C_{56}H_{39}N_7$): theoretical values C, 83.04; H, 4.85; N, 12.11; test values: C, 83.01; H, 4.86; N, 12.13. ESI-MS (m/z)(M$^+$): the theoretical value was 809.33, the measured value was 809.66.

Example 8: Synthesis of Compound 27

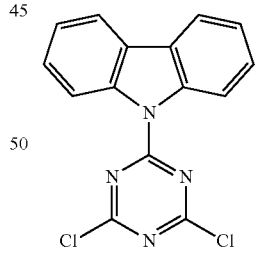

Intermediate A6

+

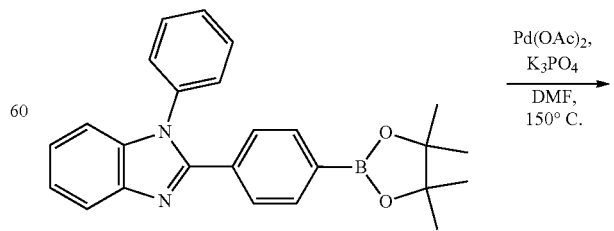

Intermediate B1

$\xrightarrow{\text{Pd(OAc)}_2, \text{K}_3\text{PO}_4, \text{DMF}, 150°\text{C.}}$

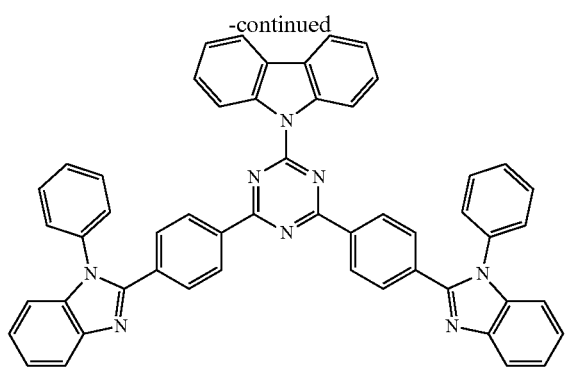

The preparation method of the compound 27 was the same with that in Example 3, except that the intermediate A1 was replaced with the intermediate A6.

Elemental analysis structure (molecular formula $C_{53}H_{34}N_8$): theoretical values C, 81.31; H, 4.38; N, 14.31; test values: C, 81.31; H, 4.36; N, 14.33. ESI-MS (m/z)(M$^+$): the theoretical value was 782.29, the measured value was 782.67.

Example 9: Synthesis of Compound 31

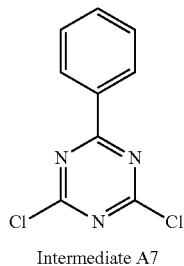
Intermediate A7

+

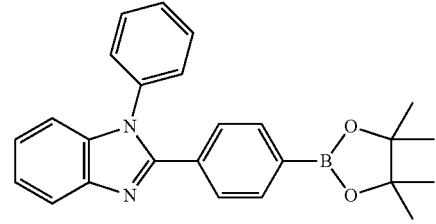
Intermediate B1

$\xrightarrow{\text{Pd(OAc)}_2, \text{K}_3\text{PO}_4}$
DMF, 150° C.

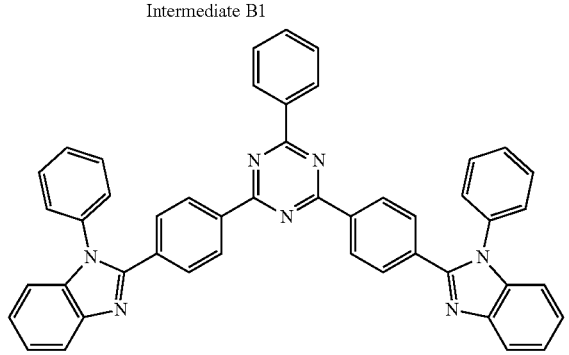

The preparation method of the compound 31 was the same with that in Example 3, except that the intermediate A1 was replaced with the intermediate A7.

Elemental analysis structure (molecular formula $C_{47}H_{31}N_7$): theoretical values C, 81.36; H, 4.50; N, 14.13; test values: C, 81.33; H, 4.52; N, 14.15. ESI-MS (m/z)(M$^+$): the theoretical value was 693.26, the measured value was 693.58.

Example 10: Synthesis of Compound 32

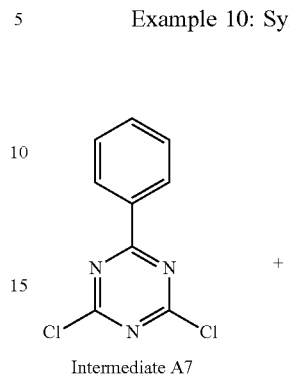
Intermediate A7

+

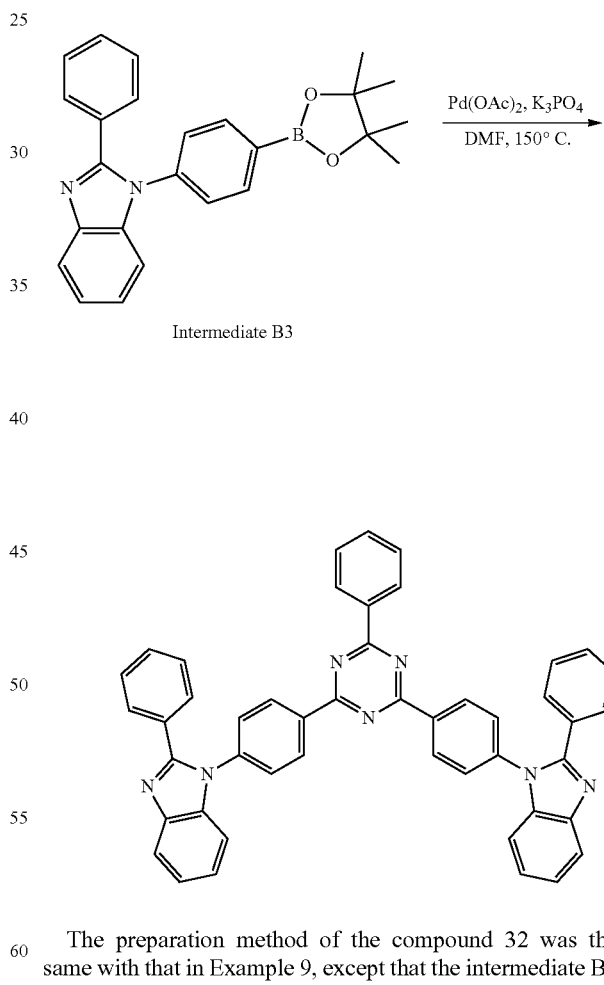
Intermediate B3

$\xrightarrow{\text{Pd(OAc)}_2, \text{K}_3\text{PO}_4}$
DMF, 150° C.

The preparation method of the compound 32 was the same with that in Example 9, except that the intermediate B1 was replaced with the intermediate B3.

Elemental analysis structure (molecular formula $C_{47}H_{31}N_7$): theoretical values C, 81.36; H, 4.50; N, 14.13; test values: C, 81.35; H, 4.51; N, 14.14. ESI-MS (m/z)(M$^+$): the theoretical value was 693.26, the measured value was 693.67.

Example 11: Synthesis of Compound 39

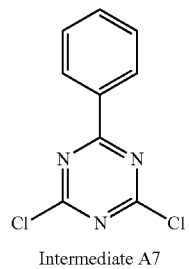

Intermediate A7

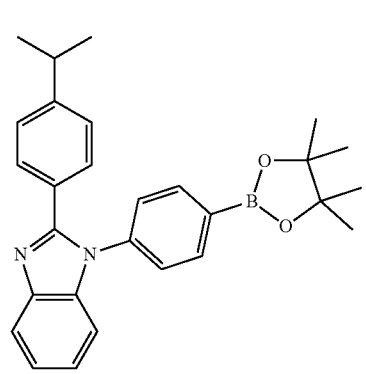

Intermediate B4

Example 12: Synthesis of Compound 48

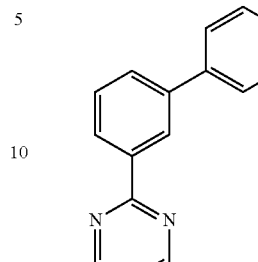

Intermediate A8

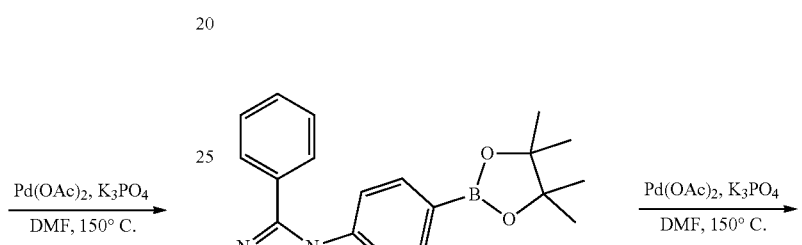

Intermediate B3

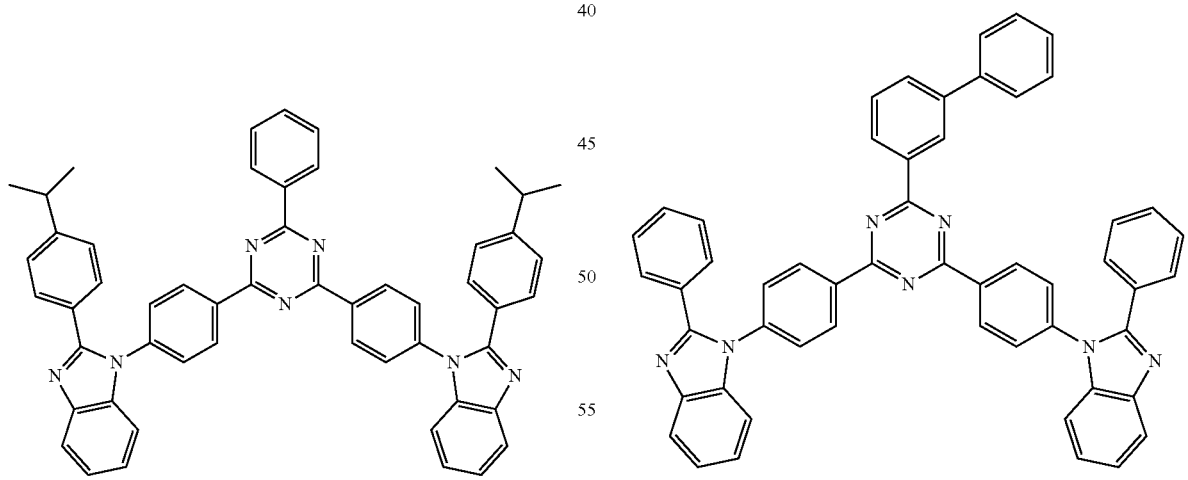

The preparation method of the compound 39 was the same with that in Example 9, except that the intermediate B1 was replaced with the intermediate B4.

Elemental analysis structure (molecular formula $C_{53}H_{43}N_7$): theoretical values C, 81.83; H, 5.57; N, 12.60; test values: C, 81.83; H, 5.54; N, 12.63. ESI-MS (m/z)(M$^+$): the theoretical value was 777.36, the measured value was 777.67.

The preparation method of the compound 48 was the same with that in Example 10, except that the intermediate A7 was replaced with the intermediate A8.

Elemental analysis structure (molecular formula $C_{53}H_{35}N_7$): theoretical values C, 82.68; H, 4.58; N, 12.74; test values: C, 82.67; H, 4.56; N, 12.77. ESI-MS (m/z)(M$^+$): the theoretical value was 769.30, the measured value was 769.73.

Example 13: Synthesis of Compound 53

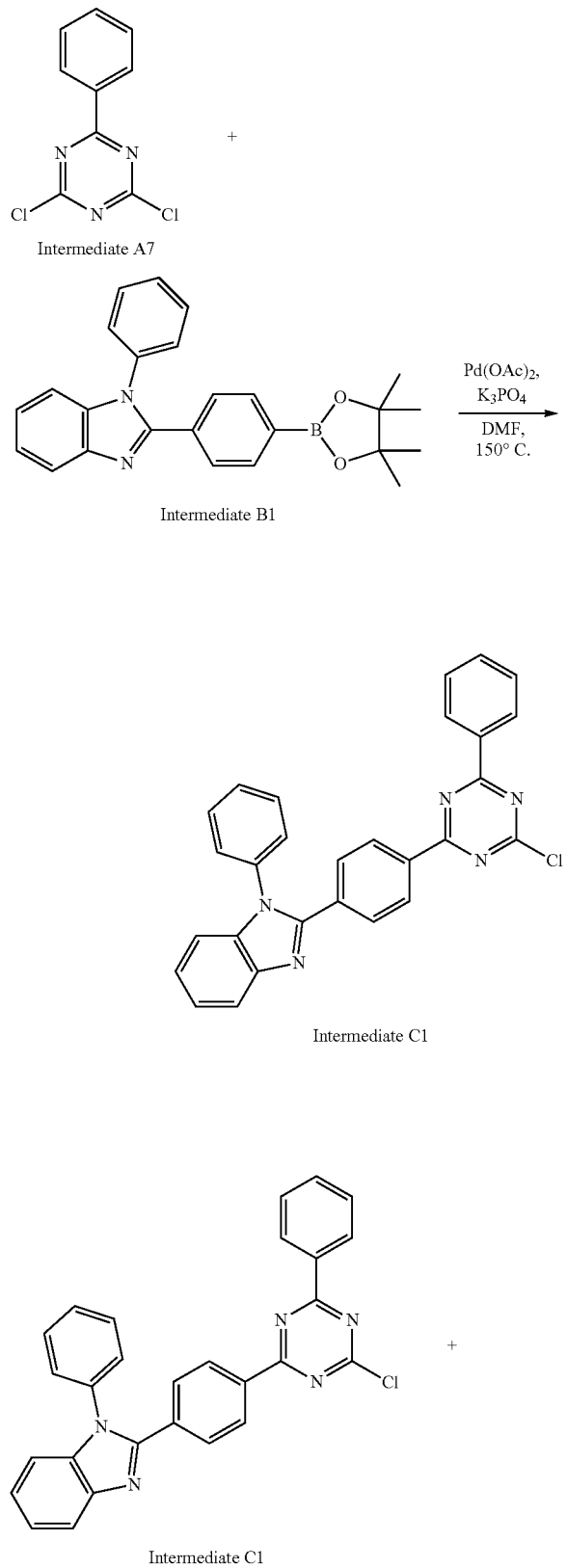

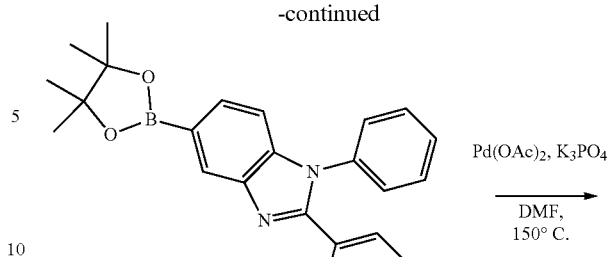

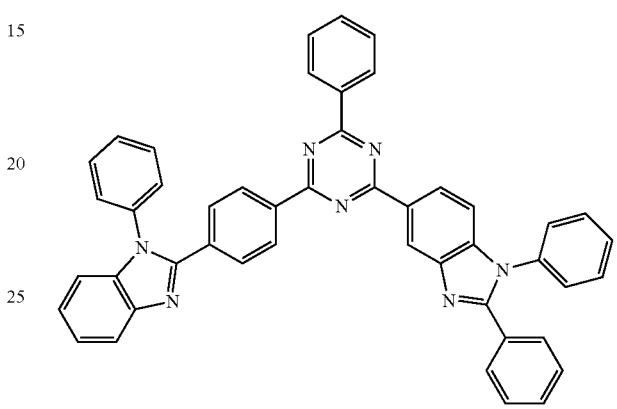

In a 250 ml three-necked flask, nitrogen gas was introduced, 0.01 mol of the intermediate A7, 150 ml of DMF, 0.015 mol of the intermediate B1, 0.0001 mol of palladium acetate were added, the mixture was stirred and then 0.01 mol of $K_3PO_4$ aqueous solution was added, the mixed solution was heated to 150° C. and refluxed for 24 hours, sampled and spotted until completion of the reaction. The mixed solution was cooled naturally, extracted with 200 ml of dichloromethane, and the layers were separated, the extract liquid was dried over anhydrous sodium sulfate, and filtered, the filtrate was rotarily evaporated, and purified using a silica gel column to obtain the intermediate C1, the purity of HPLC was 99.2%, and the yield was 85.1%.

Elemental analysis structure (molecular formula $C_{28}H_{18}ClN_5$): theoretical values C, 73.12; H, 3.94; Cl, 7.71; N, 15.23; test values: C, 73.13; H, 3.96; Cl, 7.70; N, 15.21. ESI-MS (m/z)(M+): the theoretical value was 459.13, the measured value was 459.37.

In a 250 ml three-necked flask, nitrogen gas was introduced, 0.01 mol of the intermediate C1, 150 ml of DMF, 0.015 mol of the intermediate B5, 0.0001 mol of palladium acetate were added, the mixture was stirred and then 0.01 mol of $K_3PO_4$ aqueous solution was added, the mixed solution was heated to 150° C. and refluxed for 24 hours, sampled and spotted until completion of the reaction. The mixed solution was cooled naturally, extracted with 200 ml of dichloromethane, and the layers were separated, the extract liquid was dried over anhydrous sodium sulfate, and filtered, the filtrate was rotarily evaporated, and purified using a silica gel column to obtain the intermediate C1, the purity of HPLC was 99.5%, and the yield was 71.7%.

Elemental analysis structure (molecular formula $C_{47}H_{31}N_7$): theoretical values C, 81.36; H, 4.50; N, 14.13; test values: C, 81.34; H, 4.51; N, 14.15. ESI-MS (m/z)(M+): the theoretical value was 693.26, the measured value was 693.71.

Example 14: Synthesis of Compound 59

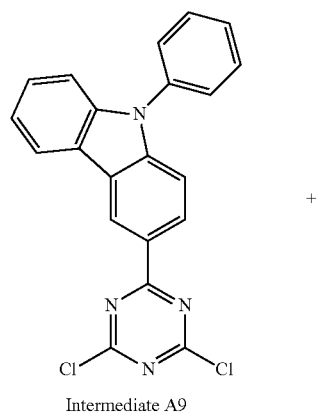
Intermediate A9

+

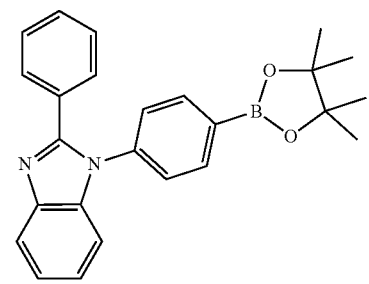
Intermediate B3

Pd(OAc)$_2$, K$_3$PO$_4$
DMF, 150° C.

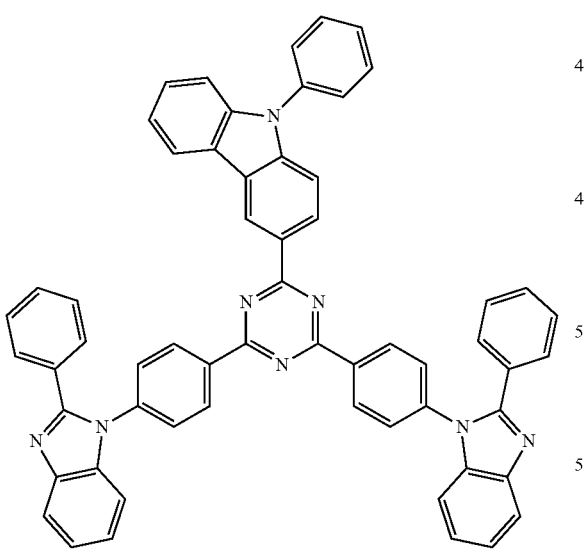

The preparation method of the compound 59 was the same with that in Example 10, except that the intermediate A7 was replaced with the intermediate A9.

Elemental analysis structure (molecular formula C$_{59}$H$_{38}$N$_8$): theoretical values C, 82.50; H, 4.46; N, 13.04; test values: C, 82.51; H, 4.47; N, 13.02. ESI-MS (m/z)(M$^+$): the theoretical value was 858.32, the measured value was 858.72.

Example 15: Synthesis of Compound 63

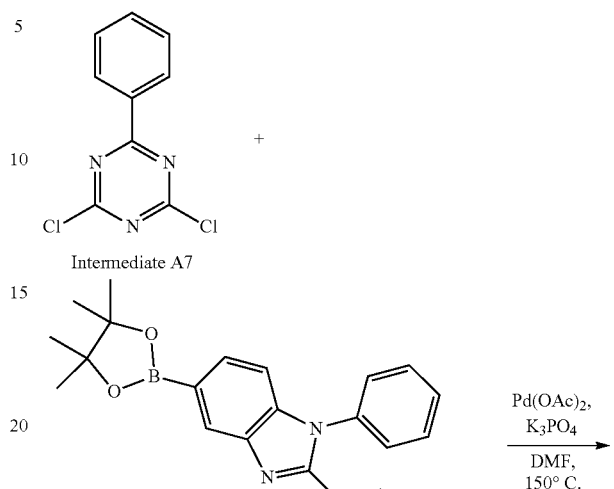
Intermediate A7

+

Intermediate B5

Pd(OAc)$_2$, K$_3$PO$_4$
DMF, 150° C.

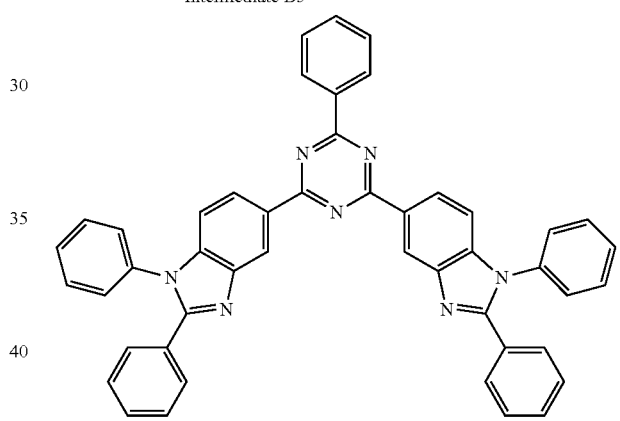

The preparation method of the compound 63 was the same with that in Example 9, except that the intermediate B1 was replaced with the intermediate B5.

Elemental analysis structure (molecular formula C$_{47}$H$_{31}$N$_7$): theoretical values C, 81.36; H, 4.50; N, 14.13; test values: C, 81.33; H, 4.53; N, 14.14. ESI-MS (m/z)(M$^+$): the theoretical value was 693.26, the measured value was 693.65.

Example 16: Synthesis of Compound 70

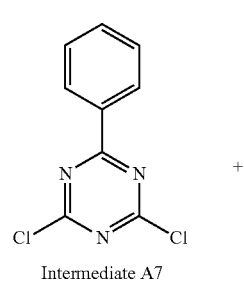
Intermediate A7

+

-continued
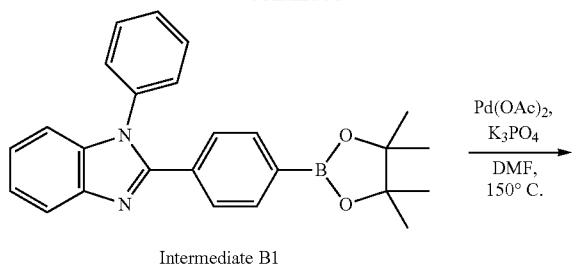
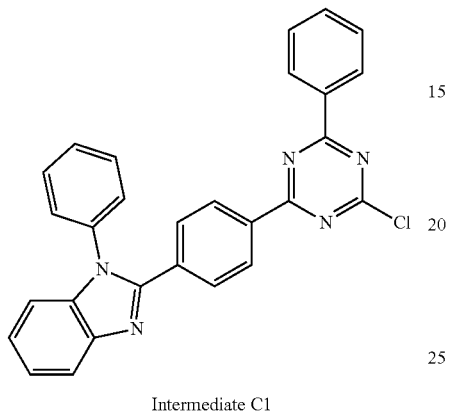
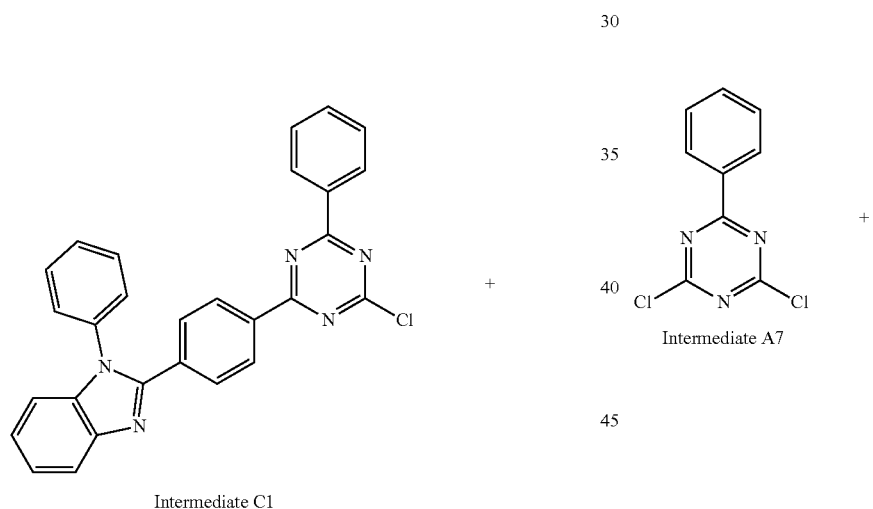
The preparation method of the compound 70 was the same with that in Example 13, except that the intermediate B5 was replaced with the intermediate B3.
Elemental analysis structure (molecular formula $C_{47}H_{31}N_7$): theoretical values C, 81.36; H, 4.50; N, 14.13; test values: C, 81.32; H, 4.54; N, 14.14. ESI-MS (m/z)(M$^+$): the theoretical value was 693.26, the measured value was 693.66.
Example 17: Synthesis of Compound 76
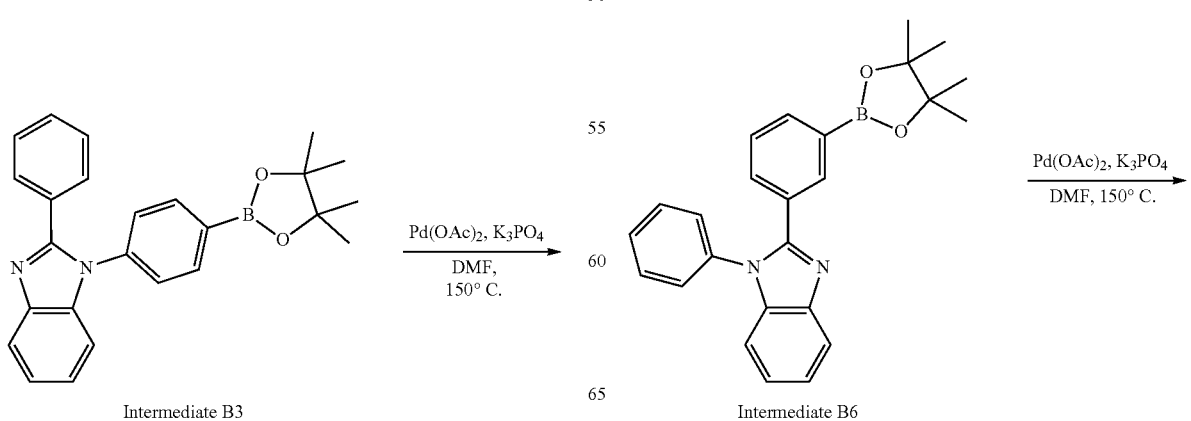

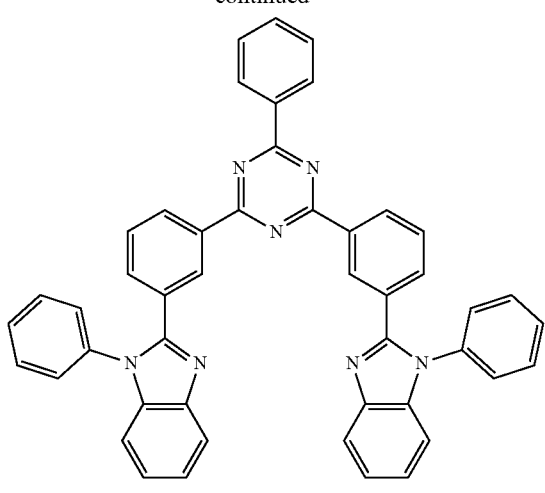
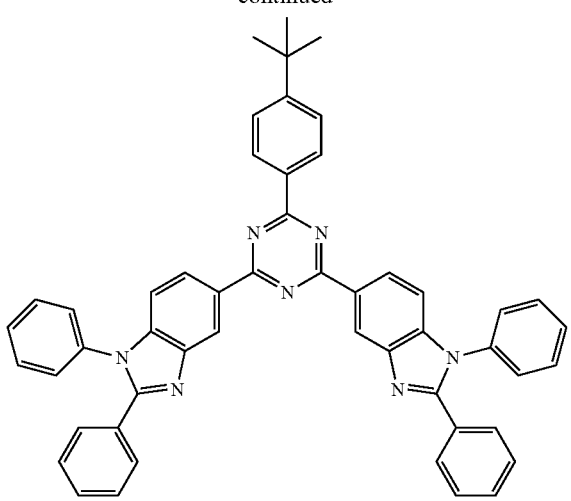

The preparation method of the compound 76 was the same with that in Example 9, except that the intermediate B1 was replaced with the intermediate B6.

Elemental analysis structure (molecular formula $C_{47}H_{31}N_7$): theoretical values C, 81.36; H, 4.50; N, 14.13; test values: C, 81.37; H, 4.52; N, 14.11. ESI-MS (m/z)(M⁺): the theoretical value was 693.26, the measured value was 693.54.

The preparation method of the compound 83 was the same with that in Example 15, except that the intermediate A7 was replaced with the intermediate A10.

Elemental analysis structure (molecular formula $C_{51}H_{39}N_7$): theoretical values C, 81.68; H, 5.24; N, 13.07; test values: C, 81.71; H, 5.25; N, 13.04. ESI-MS (m/z)(M⁺): the theoretical value was 749.33, the measured value was 749.64.

Example 18: Synthesis of Compound 83

Example 19: Synthesis of Compound 92

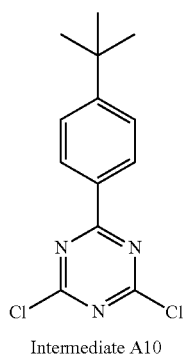

Intermediate A10

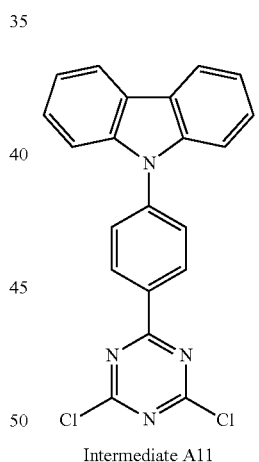

Intermediate A11

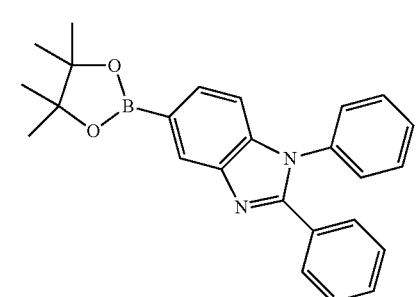

Intermediate B5

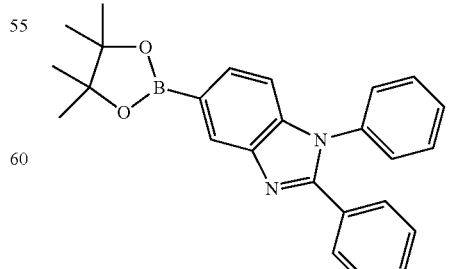

Intermediate B5

-continued

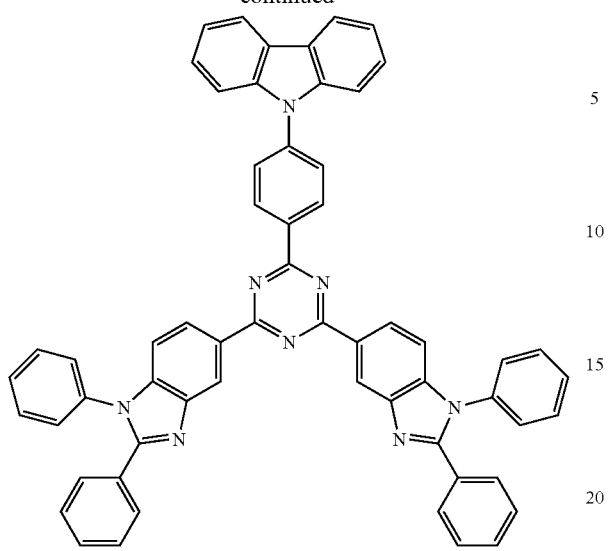

The preparation method of the compound 92 was the same with that in Example 18, except that the intermediate A10 was replaced with the intermediate A11.

Elemental analysis structure (molecular formula $C_{59}H_{38}N_8$): theoretical values C, 82.50; H, 4.46; N, 13.04; test values: C, 82.51; H, 4.47; N, 13.02. ESI-MS (m/z)(M$^+$): the theoretical value was 858.32, the measured value was 858.73.

Example 20: Synthesis of Compound 94

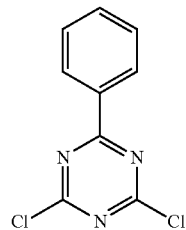

Intermediate A7

+

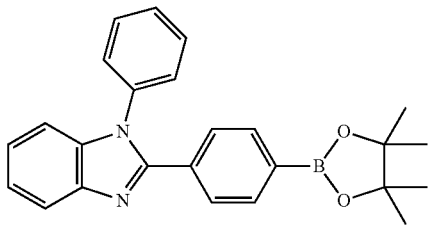

Intermediate B1

$\xrightarrow{\text{Pd(OAc)}_2, \text{K}_3\text{PO}_4, \text{DMF}, 150° \text{C.}}$ -continued

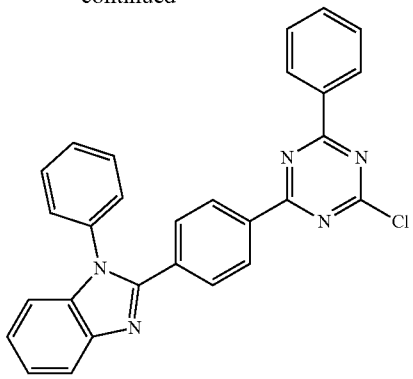

Intermediate C1

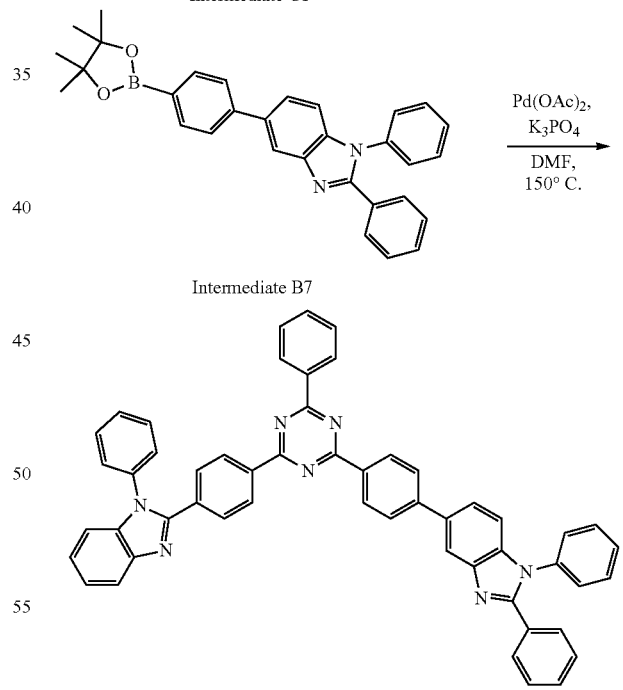

The preparation method of the compound 94 was the same with that in Example 13, except that the intermediate B5 was replaced with the intermediate B7.

Elemental analysis structure (molecular formula $C_{53}H_{35}N_7$): theoretical values C, 82.68; H, 4.58; N, 12.74; test values: C, 82.70; H, 4.57; N, 12.73. ESI-MS (m/z)(M$^+$): the theoretical value was 769.30, the measured value was 769.62.

Figure 2:
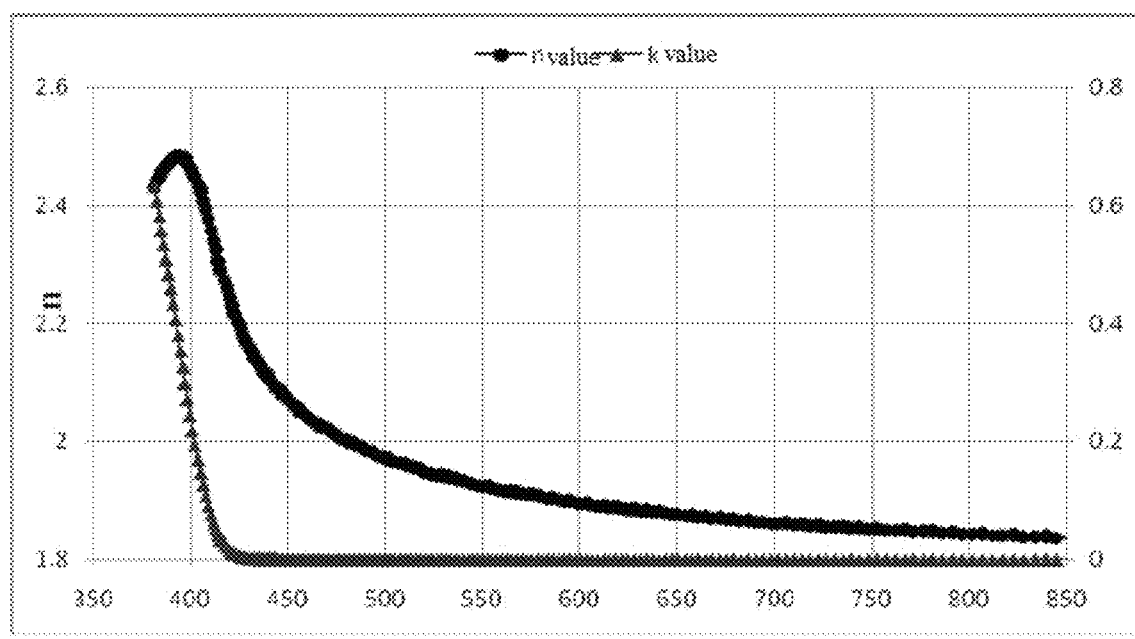
FIG. 2 is a refractive index test graph of a compound 76.

The organic compound of the present invention is used as a CPL layer material in a light-emitting device, and has a high Tg temperature (glass transition temperature) and a high refractive index. Thermal property tests and refractive index tests were performed on the compounds of the present invention and the existing materials, respectively, and the results were as shown in Table 3. Particularly, the refractive index test graph of the compound 76 was as shown in FIG. 2.

TABLE 3

| Compound | Tg (° C.) | Refractive index | |
| --- | --- | --- | --- |
| | | n@450 nm | n@600 nm |
| Compound 1 | 155 | 2.051 | 1.963 |
| Compound 10 | 151 | 1.974 | 1.892 |
| Compound 13 | 157 | 2.079 | 1.985 |
| Compound 19 | 146 | 1.953 | 1.862 |
| Compound 25 | 158 | 2.031 | 1.957 |
| Compound 27 | 147 | 1.988 | 1.895 |
| Compound 31 | 156 | 2.018 | 1.975 |
| Compound 32 | 155 | 2.076 | 1.989 |
| Compound 39 | 154 | 2.045 | 1.985 |
| Compound 48 | 157 | 2.094 | 1.979 |
| Compound 53 | 155 | 2.055 | 1.967 |
| Compound 59 | 161 | 1.984 | 1.876 |
| Compound 63 | 156 | 2.095 | 1.988 |
| Compound 70 | 155 | 2.084 | 1.976 |
| Compound 76 | 153 | 2.075 | 1.908 |
| Compound 83 | 147 | 1.975 | 1.867 |
| Compound 92 | 158 | 1.987 | 1.894 |
| Compound 94 | 153 | 2.094 | 1.975 |
| CBP | — | 1.874 | 1.794 |
| Alq3 | 149 | 1.780 | 1.731 |
| TPBi | 121 | 1.801 | 1.734 |

Note: the glass transition temperature (Tg) was determined by differential scanning calorimetry (DSC, DSC204F1 Differential Scanning Calorimeter, NETZSCH, Germany) at a heating rate of 10° C./min; the refractive index was measured using an ellipsometer (J. A. Woollam Co., USA, Model: ALPHA-SE), and the tests were conducted in an atmospheric environment.

As can be seen from the table above, compared to the currently-used materials, such as CBP, Alq3 and TPBi, the organic compound of the present invention has a relatively high glass transition temperature and a high refractive index, and meanwhile, since there are rigid groups of triazine and benzimidazole, the thermal stability of the material can be guaranteed. Therefore, the organic material with triazine and benzimidazole as the core of the present invention can effectively improve the light extraction efficiency of a device and ensure a long service life of the OLED device when applied to the CPL layer of the OLED device.

Hereinafter, the application effect of the OLED material synthetized in the present invention in the device will be described in detail through Device examples 1 to 21 and Device comparative example 1. Compared to Device example 1, Device examples 2 to 21 and Device comparative example 1 of the present invention have identical device fabricating processes, adopt the same substrate materials and electrode materials, and maintain consistency in film thickness of the electrode material, except that Device examples 2 to 18 replace the CPL layer material in the device; Device examples 19 to 21 replace the hole block layer or the electron transport layer material, and performance test results of the device in each example are as shown in Table 4.

Device example 1: as shown in FIG. 1, an electroluminescent device was prepared by the steps of:

a) cleaning an ITO anode layer 2 on a transparent OLED device substrate 1, cleaning in deionized water, acetone and alcohol each for 15 minutes, and then treating in a plasma cleaner for 2 minutes;

b) vapor-depositing a hole injection layer material HAT-CN with a thickness of 10 nm on the ITO anode layer 2 by vacuum vapor deposition, wherein, this layer functions as a hole injection layer 3;

c) vapor-depositing a hole transport layer material NPB with a thickness of 80 nm on the hole injection layer 3 by vacuum vapor deposition, wherein, this layer functions as a hole transport layer 4;

d) vapor-depositing a light-emitting layer 5 with a thickness of 30 nm on the hole transport layer 4, wherein, CBP functions as a host material, Ir(ppy)$_3$ functions as a dopant material, and a mass ratio of Ir(ppy)$_3$ to CBP is 1:9;

e) vapor-depositing an electron transport material TPBI with a thickness of 40 nm on the light-emitting layer 5 by vacuum vapor deposition, wherein, this organic material layer is used as a hole block layer or an electron transport layer 6;

f) vapor-depositing an electron injection layer LiF with a thickness of 1 nm by vacuum vapor deposition on the hole block layer or an electron transport layer 6, wherein, this layer functions as an electron injection layer 7;

g) vapor-depositing a cathode Mg:Ag/Ag layer on the electron injection layer 7 by vacuum vapor deposition, Mg:Ag (at a doping ratio of 9:1) layer has a thickness of 15 nm, the Ag layer has a thickness of 3 nm, and this layer is a cathode layer 8;

h) vapor-depositing CPL material compound 1 with a thickness of 50 nm by vacuum vapor deposition on the cathode layer 8, wherein, this organic material layer is used as a CPL layer 9.

After the fabrication of the electroluminescent device was completed according to the above steps, the current efficiency and the service life of the device were measured, and the results were as shown in table 4. Molecular structural formulas of related materials were as shown below:

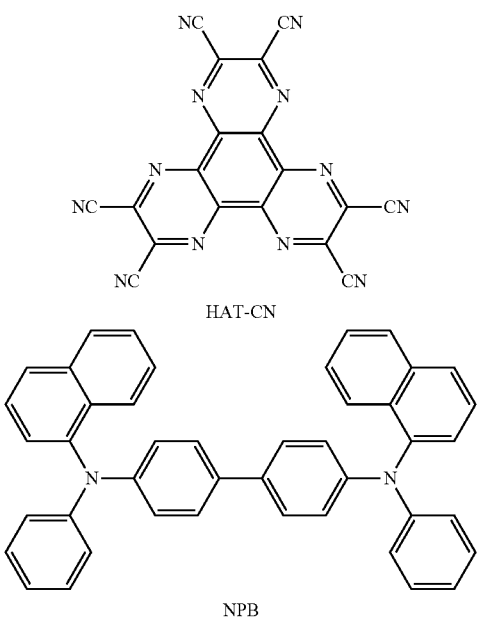

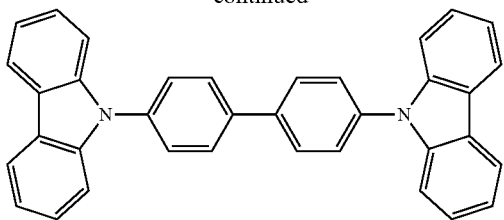

CBP

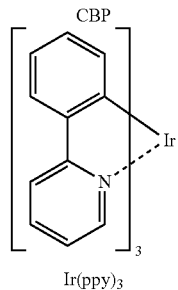

Ir(ppy)₃

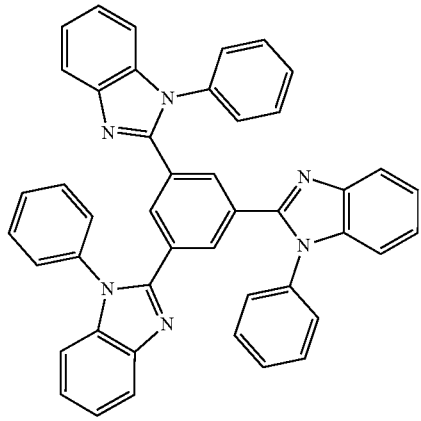

TPBI

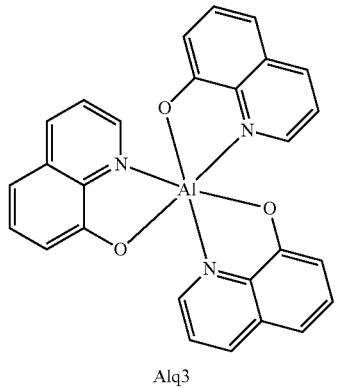

Alq3

Device example 2: CPL layer material of the electroluminescent device was changed to Compound 10 of the present invention. Device example 3: CPL layer material of the electroluminescent device was changed to Compound 13 of the present invention. Device example 4: CPL layer material of the electroluminescent device was changed to Compound 19 of the present invention. Device example 5: CPL layer material of the electroluminescent device was changed to Compound 25 of the present invention. Device example 6: CPL layer material of the electroluminescent device was changed to Compound 27 of the present invention. Device example 7: CPL layer material of the electroluminescent device was changed to Compound 31 of the present invention. Device example 8: CPL layer material of the electroluminescent device was changed to Compound 32 of the present invention. Device example 9: CPL layer material of the electroluminescent device was changed to Compound 39 of the present invention. Device example 10: CPL layer material of the electroluminescent device was changed to Compound 48 of the present invention. Device example 11: CPL layer material of the electroluminescent device was changed to Compound 53 of the present invention. Device example 12: CPL layer material of the electroluminescent device was changed to Compound 59 of the present invention. Device example 13: CPL layer material of the electroluminescent device was changed to Compound 63 of the present invention. Device example 14: CPL layer material of the electroluminescent device was changed to Compound 70 of the present invention. Device example 15: CPL layer material of the electroluminescent device was changed to Compound 76 of the present invention. Device example 16: CPL layer material of the electroluminescent device was changed to Compound 83 of the present invention. Device example 17: CPL layer material of the electroluminescent device was changed to Compound 92 of the present invention. Device example 18: CPL layer material of the electroluminescent device was changed to Compound 94 of the present invention. Device example 19: the hole block layer or the electron transport layer material of the electroluminescent device was changed to Compound 19 of the present invention. Device example 20: the hole block layer or the electron transport layer material of the electroluminescent device was changed to Compound 52 of the present invention. Device example 21: the hole block layer or the electron transport layer material of the electroluminescent device was changed to Compound 85 of the present invention. Device comparative example 1: CPL layer material of the electroluminescent device was changed to a known material Alq3. The measured data of the electroluminescent device is as shown in Table 4.

TABLE 4

| | @10 mA/cm² | | |
|---|---|---|---|
| No. | Current efficiency(cd/A) | Brightness (cd/m²) | Color |
| Device example 1 | 53.61 | 5361.14 | Green light |
| Device example 2 | 52.71 | 5271.29 | Green light |
| Device example 3 | 53.94 | 5393.81 | Green light |
| Device example 4 | 52.47 | 5246.78 | Green light |
| Device example 5 | 53.38 | 5337.80 | Green light |
| Device example 6 | 52.88 | 5287.62 | Green light |
| Device example 7 | 53.23 | 5322.63 | Green light |
| Device example 8 | 53.90 | 5390.31 | Green light |
| Device example 9 | 53.54 | 5354.14 | Green light |
| Device example 10 | 54.11 | 5411.32 | Green light |
| Device example 11 | 53.66 | 5365.81 | Green light |
| Device example 12 | 52.83 | 5282.96 | Green light |
| Device example 13 | 54.12 | 5412.48 | Green light |
| Device example 14 | 54.00 | 5399.65 | Green light |
| Device example 15 | 53.89 | 5389.15 | Green light |
| Device example 16 | 52.72 | 5272.45 | Green light |
| Device example 17 | 52.86 | 5286.46 | Green light |
| Device example 18 | 54.11 | 5411.32 | Green light |
| Device example 19 | 61.65 | 6165.31 | Green light |
| Device example 20 | 63.25 | 6325.54 | Green light |
| Device example 21 | 66.34 | 6634.39 | Green light |
| Device comparative example 1 | 48.28 | 4828 | Green light |

Figure 3:
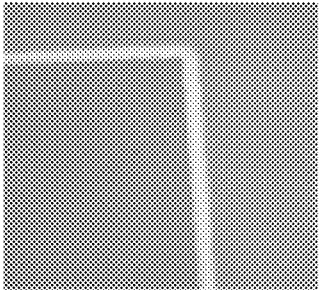
FIG. 3 is a comparative diagram of film accelerated experiments between a compound 32 and a known material CBP.
Figure 3:
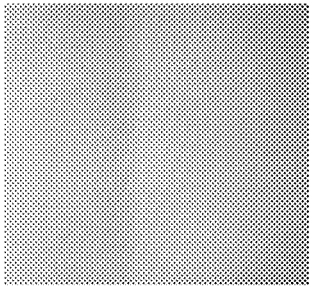
Figure 3:
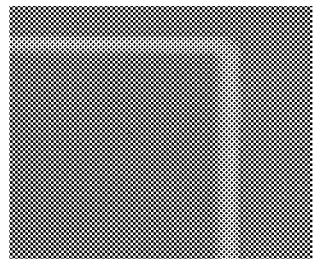
Figure 3:
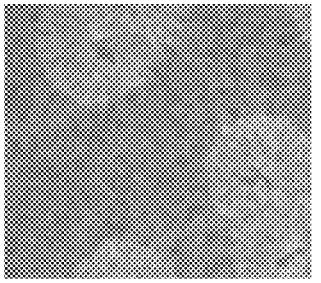
Figure 3:
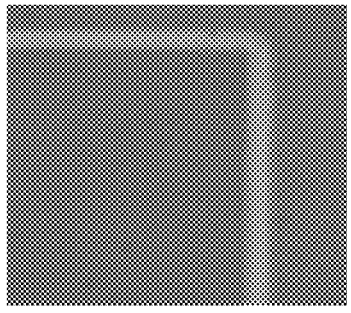

As can be seen from results in Table 4, after the organic compound with triazine and benzimidazole as the core of the present invention was applied to fabrication of the OLED light-emitting device, the light extraction efficiency was improved significantly when compared with that in device comparative example 1, both brightness and efficiency of the device were improved under the same current density; since brightness and efficiency had been improved, the power consumption of the OLED device under constant brightness was relatively reduced, and the service life of the OLED device was prolonged. In order to illustrate the phase-state crystallization stability of the material film of the present invention, the material compound 32 of the present invention and a known material CBP were subjected to film accelerated crystallization experiments: the compound 32 and the CBP were vapor-deposited on the alkali-free glass by vacuum vapor deposition, respectively, and packaged in a glove-box (content of water and oxygen <0.1 ppm), the packaged samples were placed under double 85 (temperature 85° C., humidity 85%) conditions, and observed periodically with microscope (LEICA, DM8000M, 5*10 magnification) for the crystalline state of the material film. The experimental results were as shown in Table 5, and surface morphologies of the materials were as shown in FIG. 3:

TABLE 5

| | Name of material | |
|---|---|---|
| | Compound 32 | CBP |
| After film-forming of the material | The surface is smooth, flat, uniform | The surface is smooth, flat, uniform |
| 72 h after the experiment | The surface is smooth, flat, uniform, with no crystallization | The surface forms several dispersed circular crystallization surfaces |
| 600 h after the experiment | The surface is smooth, flat, uniform, with no crystallization | The surface is cracked |

The above experiment shows that the film crystallization stability of the material disclosed in the present invention is far higher than that of known materials, and has beneficial effects on the service life after being applied to an OLED device.

What is claimed is:

1. An organic compound with triazine and benzimidazole as a core, wherein a structure of the organic compound is represented by the following formula (1):

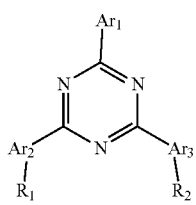

formula (1)

and wherein, $Ar_1$ is one selected from the group consisting of phenyl, naphthyl, biphenyl, terphenyl, anthryl, dibenzofuranyl, dibenzothiophenyl, 9,9-dimethylfluorenyl or 9-phenylcarbazolyl, substituted or unsubstituted by halogen atoms, protium atoms, deuterium atoms, tritium atoms, and linear or branched alkyl with 1 to 10 carbons;

$Ar_2$ is a single bond or one selected from the group consisting of phenyl, naphthyl, biphenyl, terphenyl, anthryl or pyridyl, substituted or unsubstituted by halogen atoms, protium atoms, deuterium atoms, tritium atoms, and linear or branched alkyl with 1 to 10 carbons;

$Ar_3$ is a single bond or one selected from the group consisting of phenyl, naphthyl, biphenyl, terphenyl, anthryl or pyridyl, substituted or unsubstituted by halogen atoms, protium atoms, deuterium atoms, tritium atoms, and linear or branched alkyl with 1 to 10 carbons;

$R_1$ is one selected from the group consisting of formula (2), formula (3) and formula (4); $R_2$ is one selected from the group consisting of formula (2), formula (3) and formula (4); wherein formula (2), formula (3) and formula (4) are:

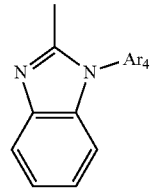

formula (2)

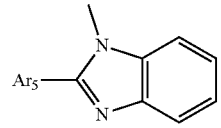

formula (3)

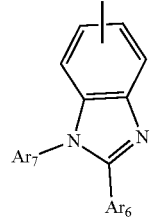

formula (4)

and wherein, $Ar_4$ is one selected from the group consisting of phenyl, naphthyl, biphenyl, terphenyl or pyridyl, substituted or unsubstituted by halogen atoms, and linear or branched alkyl with 1 to 10 carbons;

$Ar_5$ is one selected from the group consisting of phenyl, naphthyl, biphenyl, terphenyl or pyridyl, substituted or unsubstituted by halogen atoms, and linear or branched alkyl with 1 to 10 carbons;

$Ar_6$ is one selected from the group consisting of phenyl, naphthyl, biphenyl, terphenyl or pyridyl, substituted or unsubstituted by halogen atoms, and linear or branched alkyl with 1 to 10 carbons;

$Ar_7$ is one selected from the group consisting of phenyl, naphthyl, biphenyl, terphenyl or pyridyl, substituted or unsubstituted by halogen atoms, and linear or branched alkyl with 1 to 10 carbons.

2. The organic compound according to claim 1, wherein a particular structural formula of the organic compound is any one selected from the group consisting of:

(1)
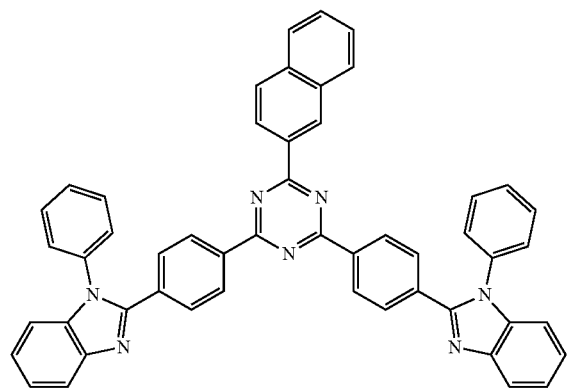
(2)
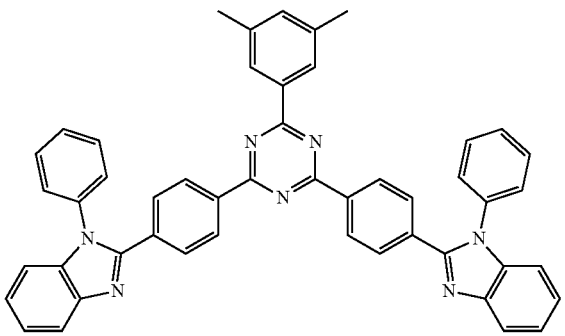
(3)
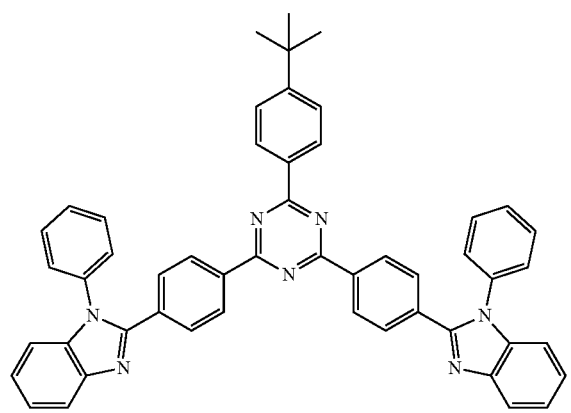
(4)
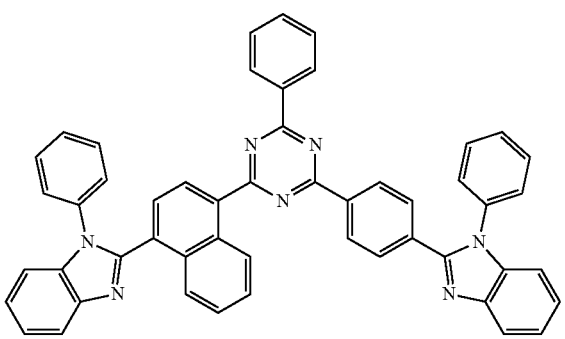
(5)
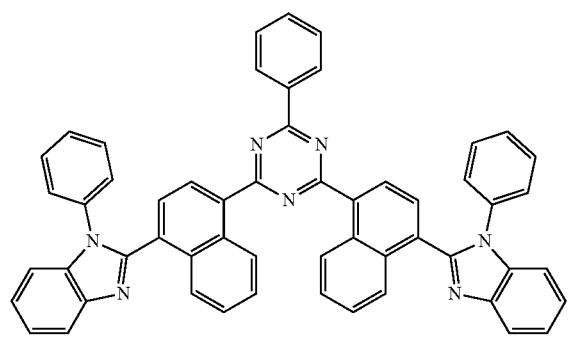
(6)
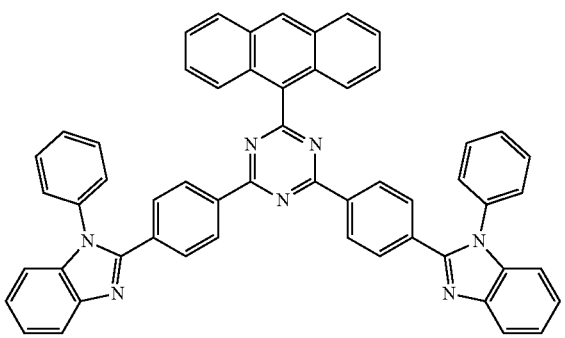
(7)
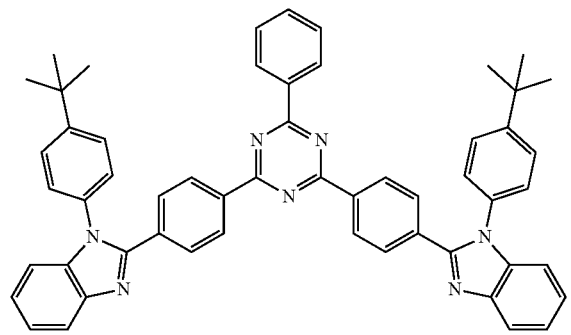
(8)
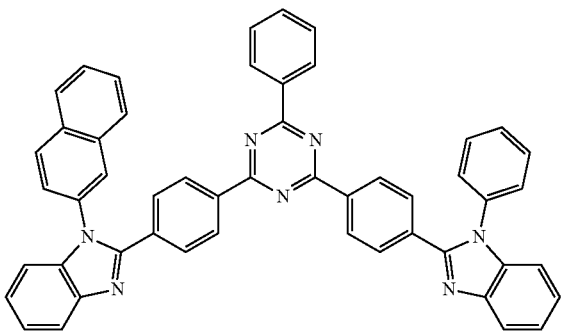

-continued
(9)
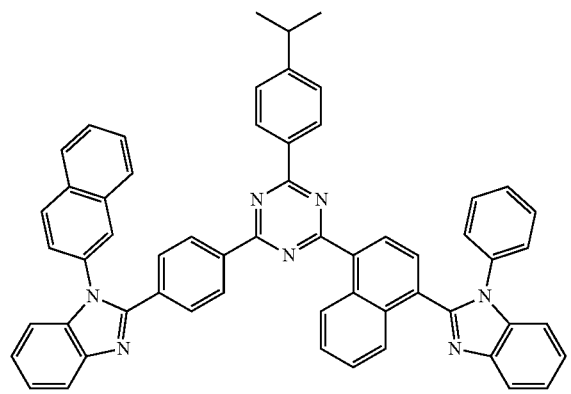
(10)
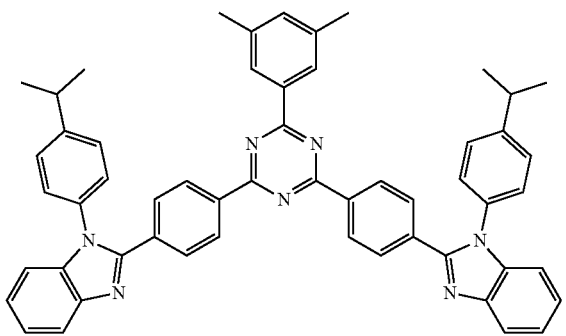
(11)
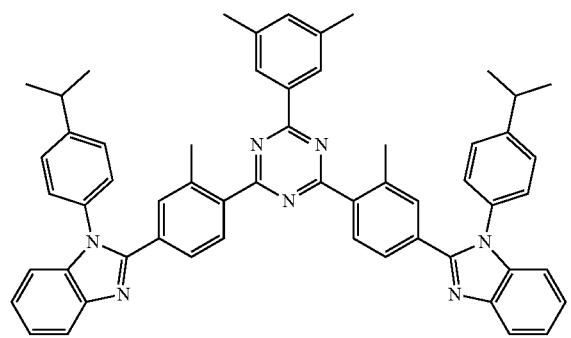
(12)
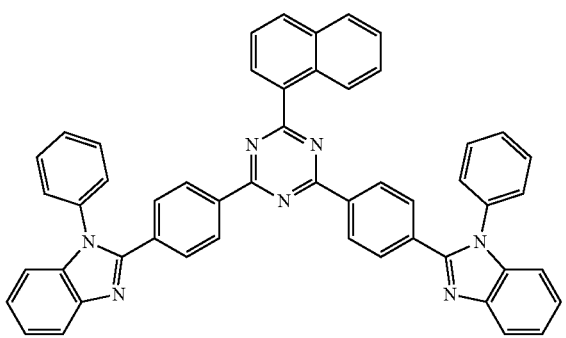
(13)
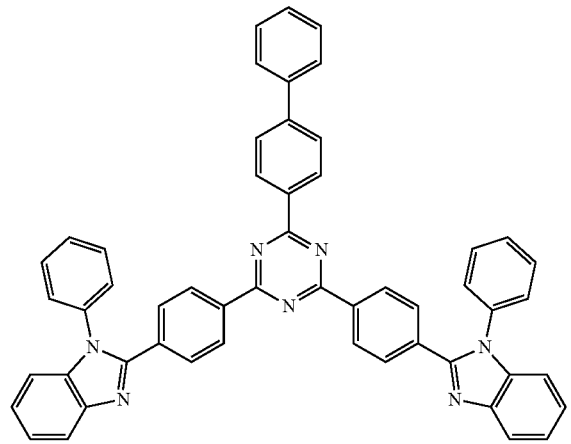
(14)
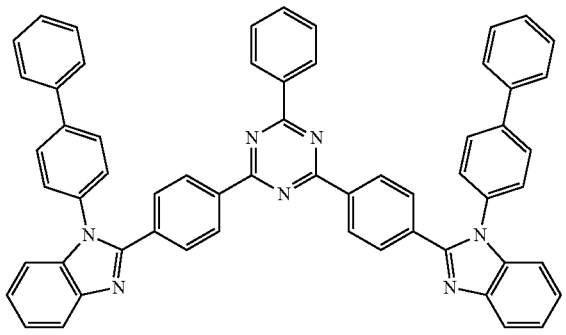
(15)
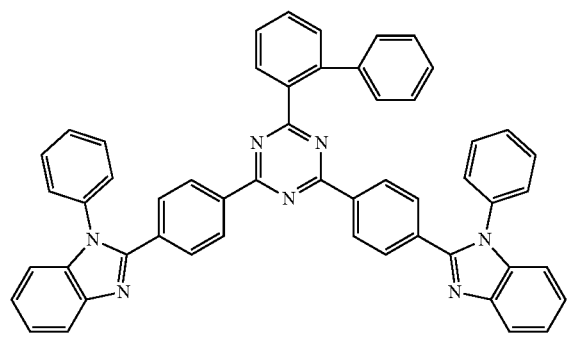

(16)
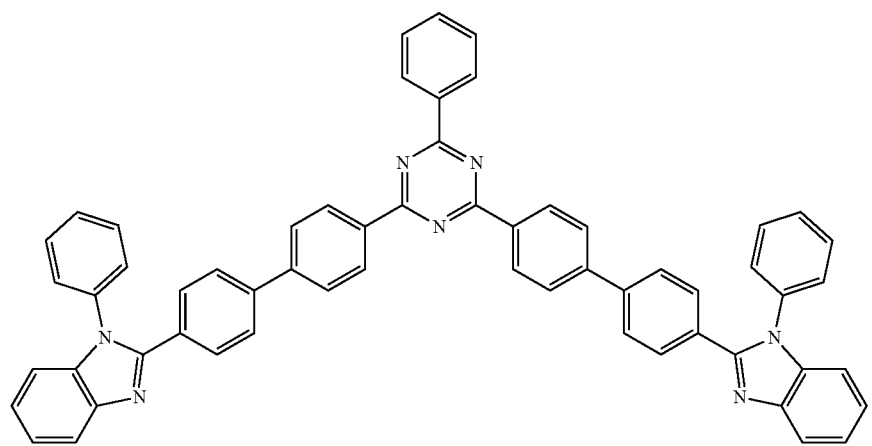
(17)
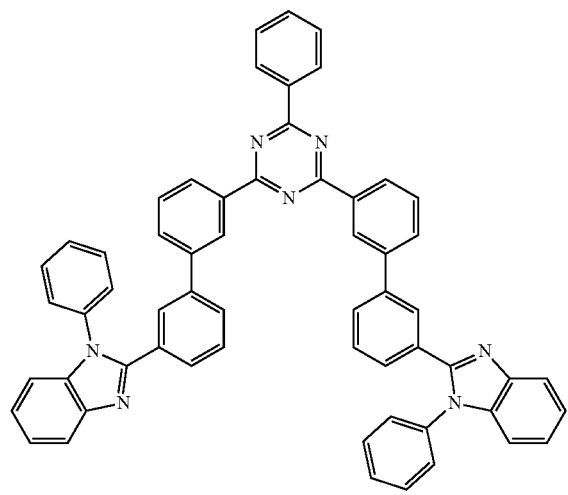
(18)
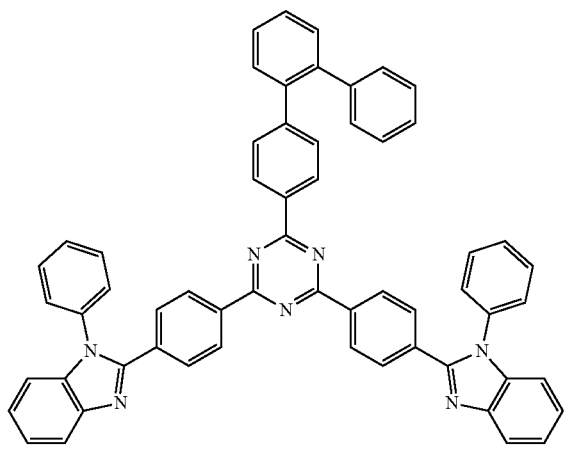
(19)
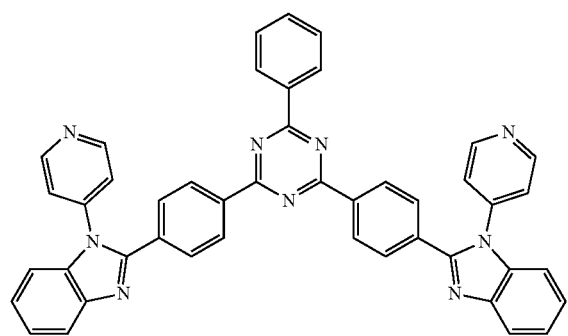
(20)
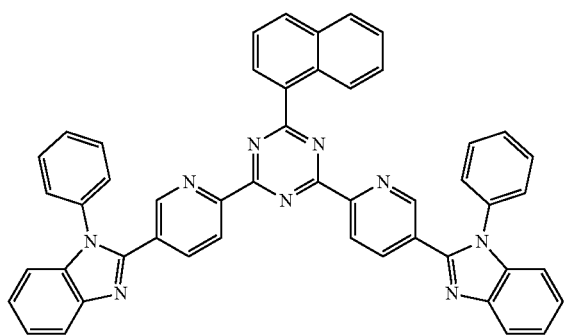

-continued
(21)
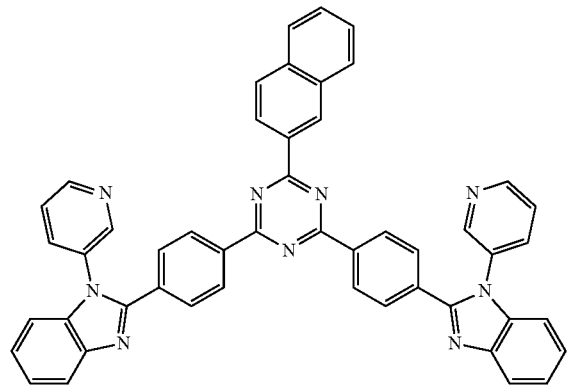
(22)
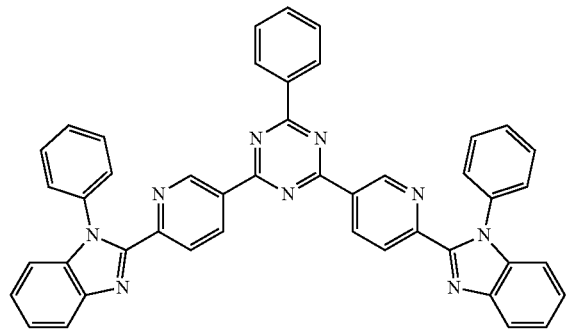
(23)
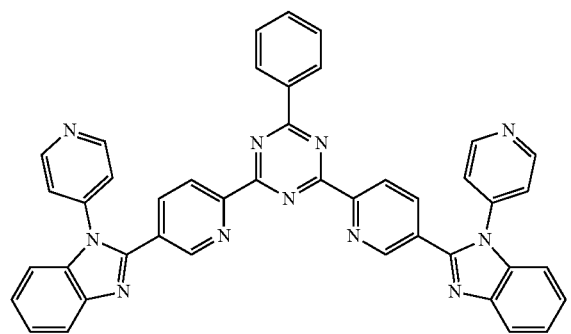
(24)
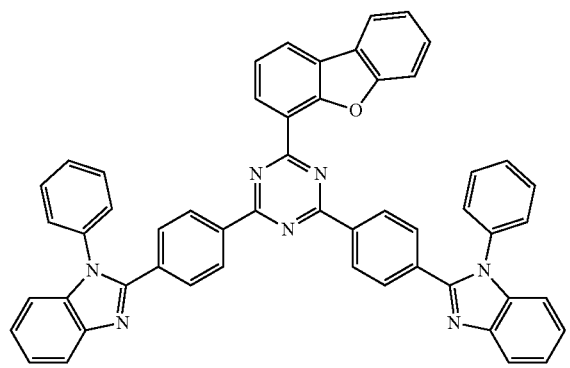
(25)
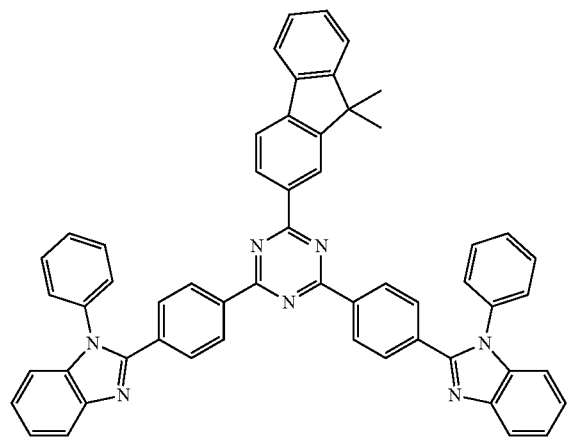
(26)
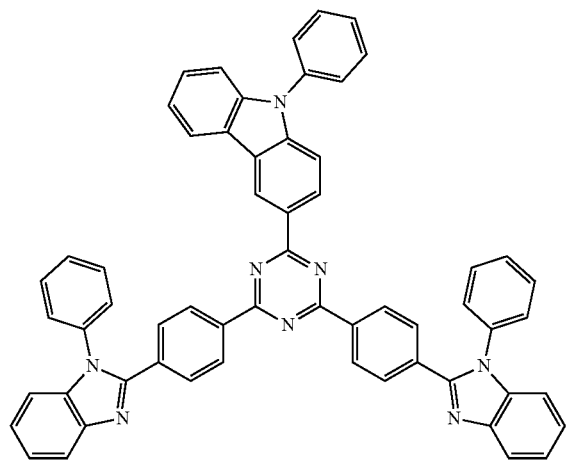

-continued
(27)
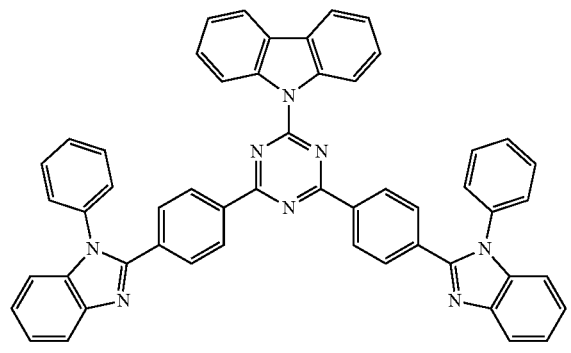
(28)
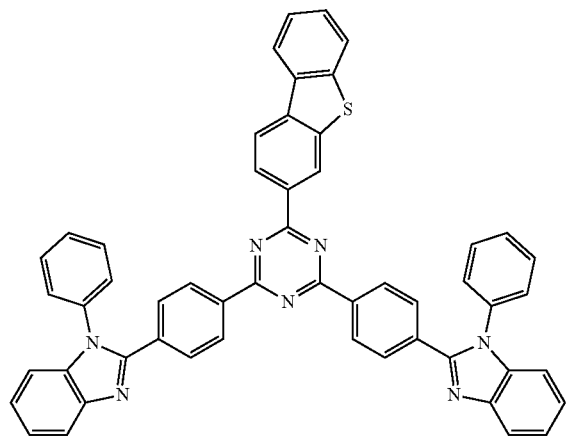
(29)
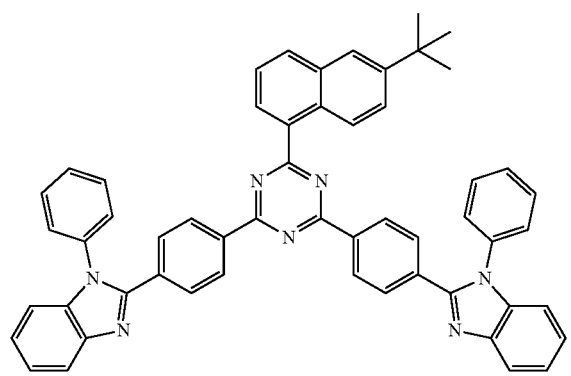
(30)
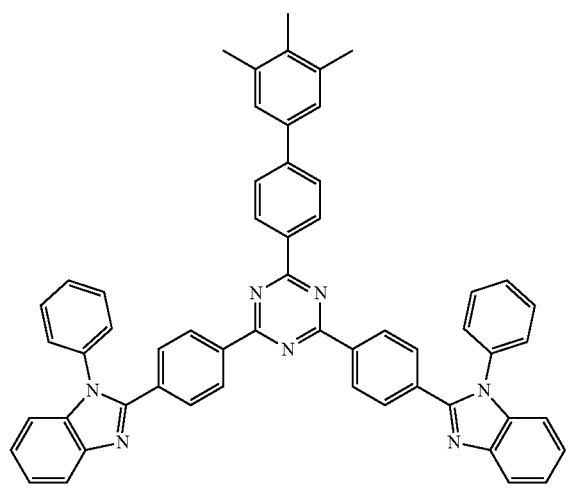
(31)
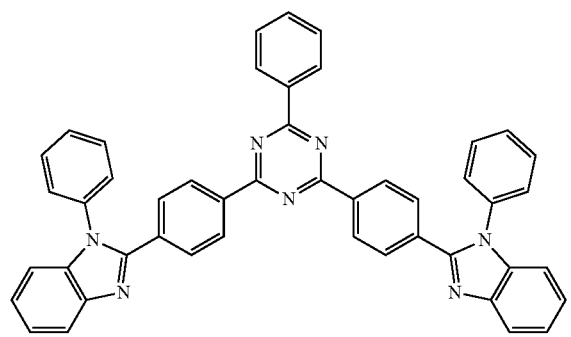
(32)
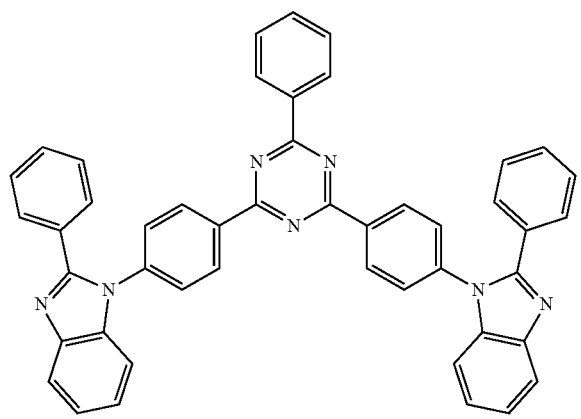

(33)
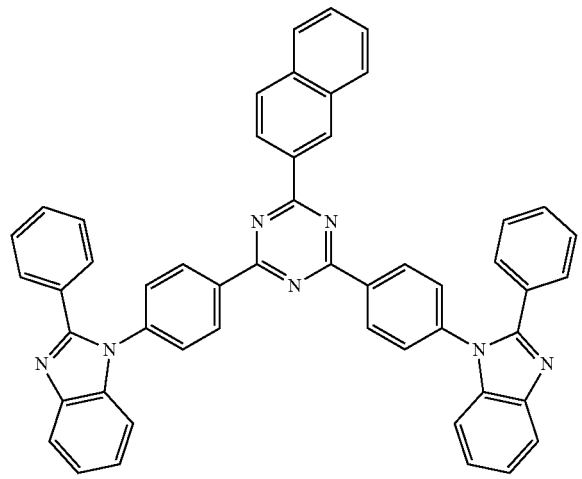
(34)
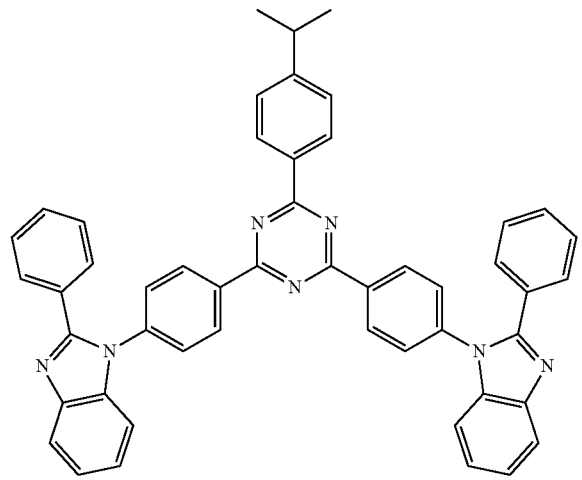
(35)
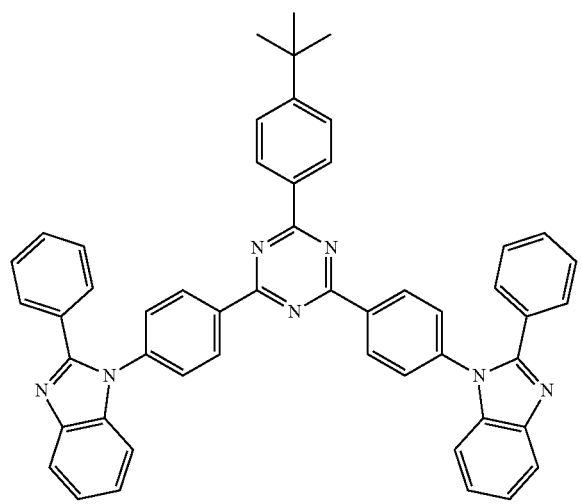
(36)
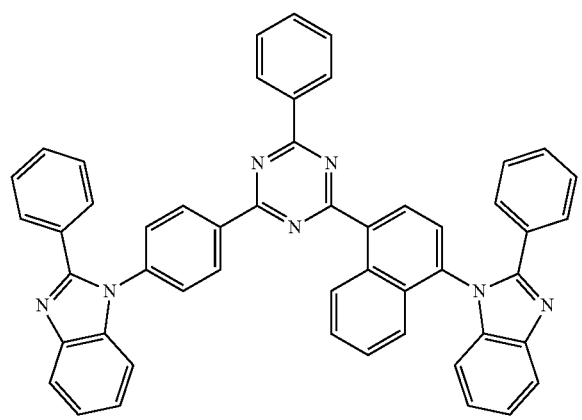
(37)
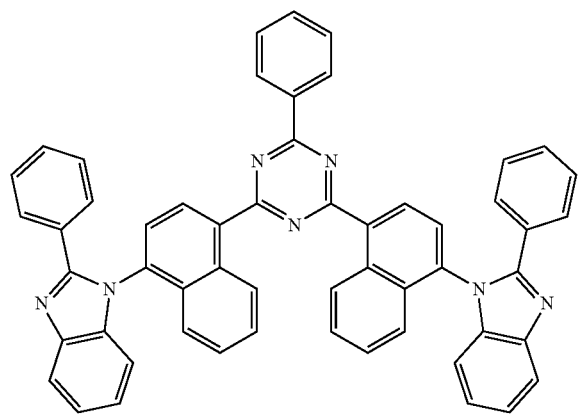
(38)
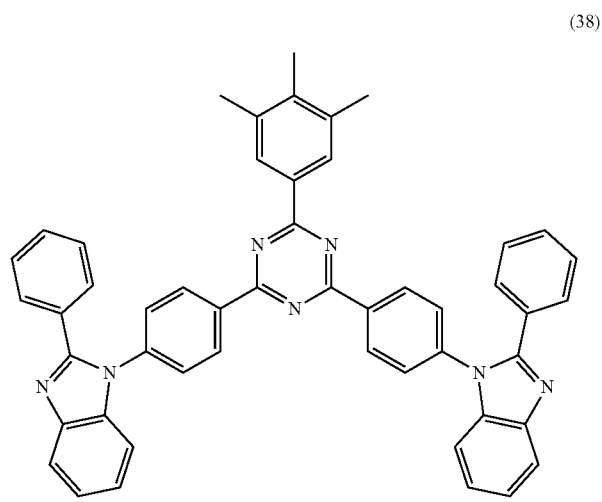

-continued
(39)
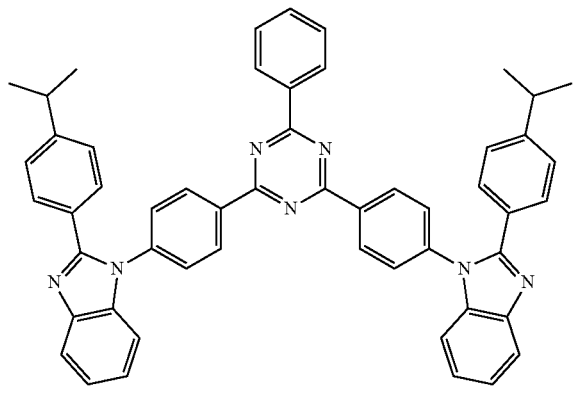
(40)
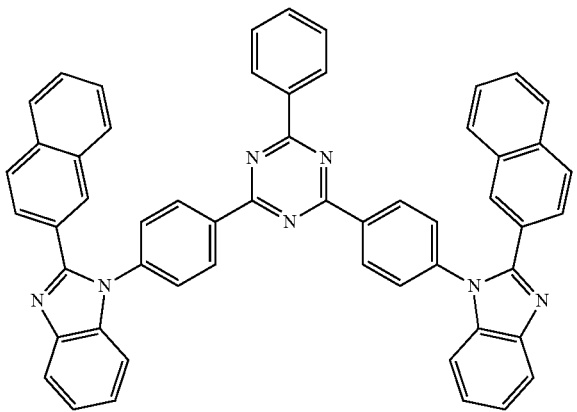
(41)
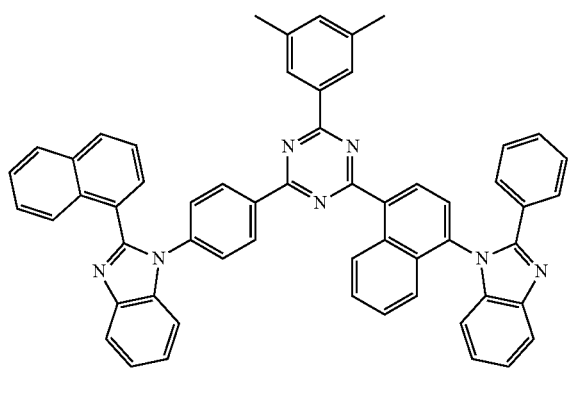
(42)
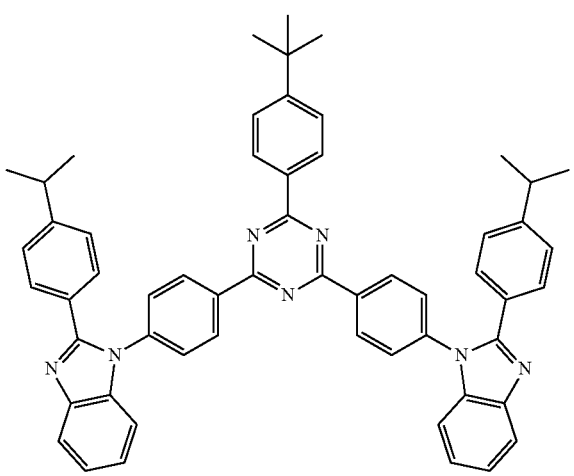
(43)
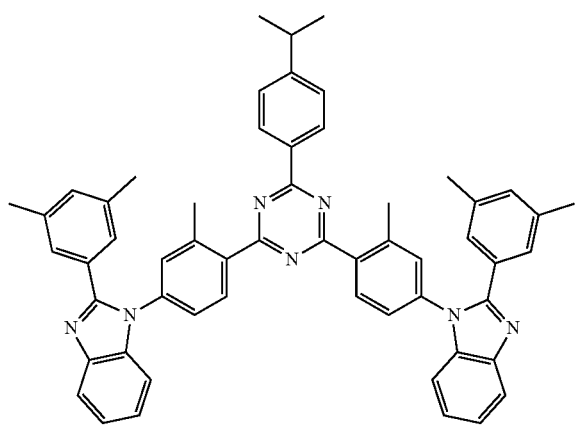
(44)
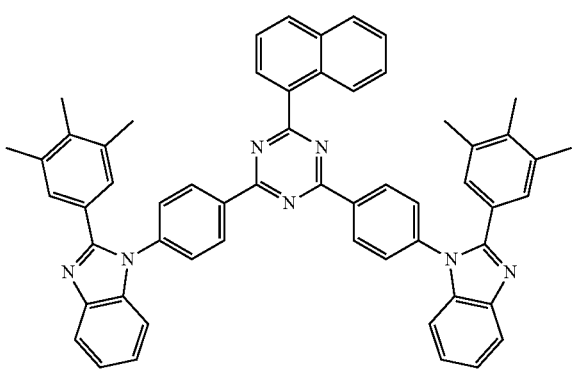

-continued
(45)
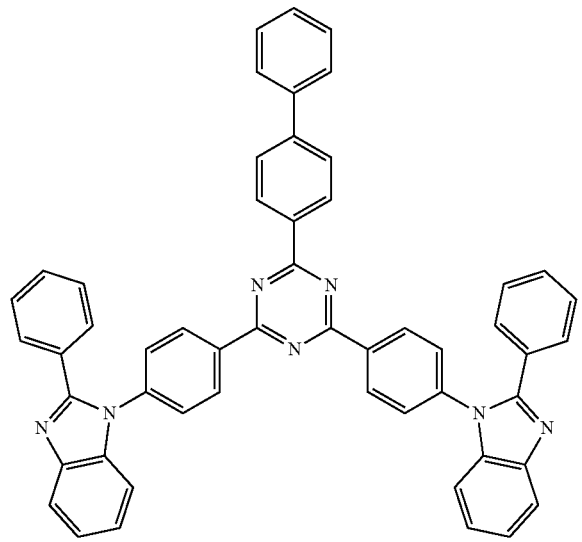
(46)
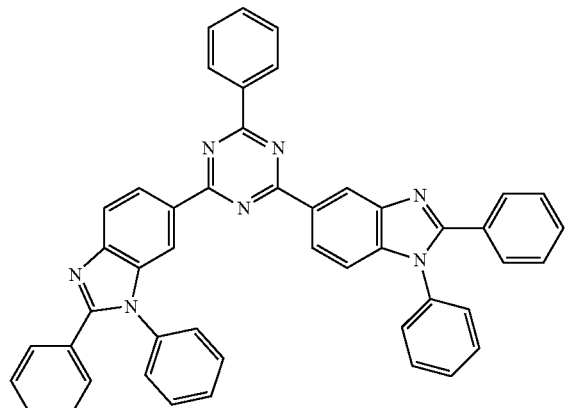
(47)
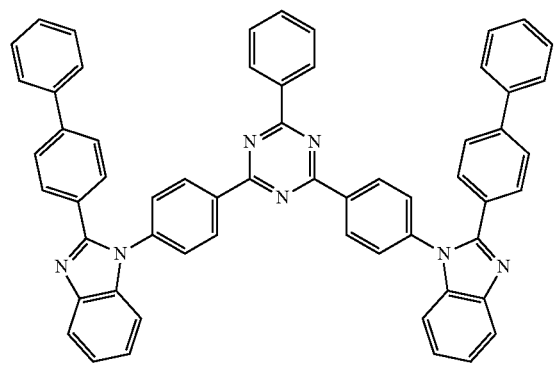
(48)
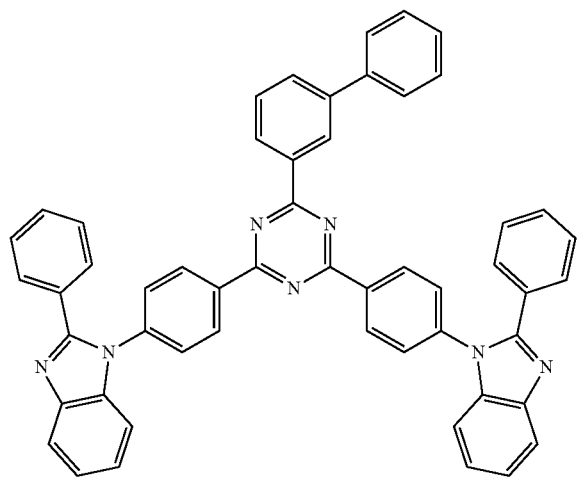
(49)
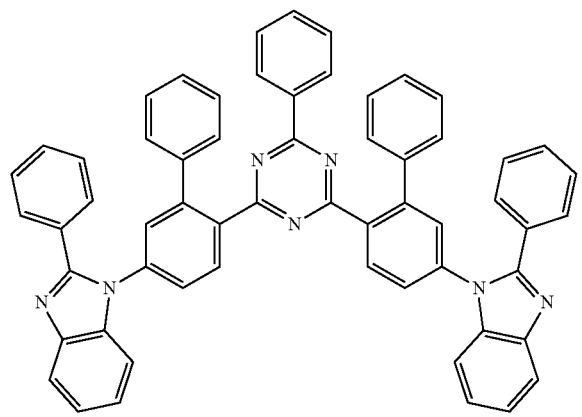
(50)
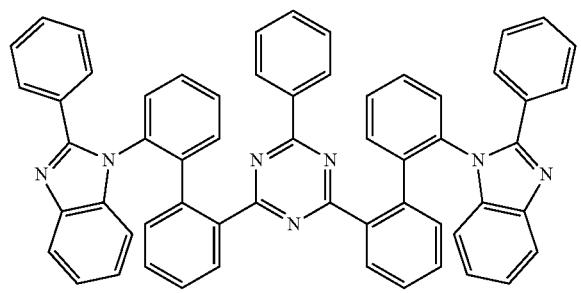

-continued
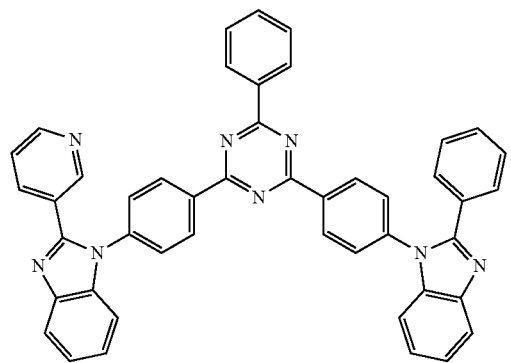
(51)
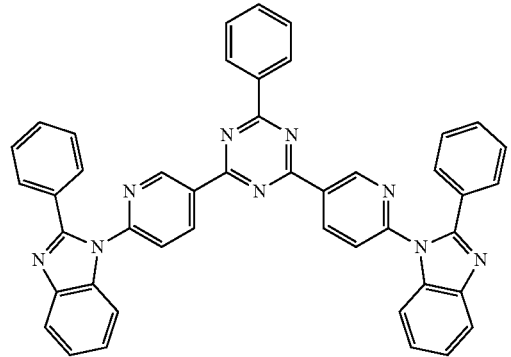
(52)
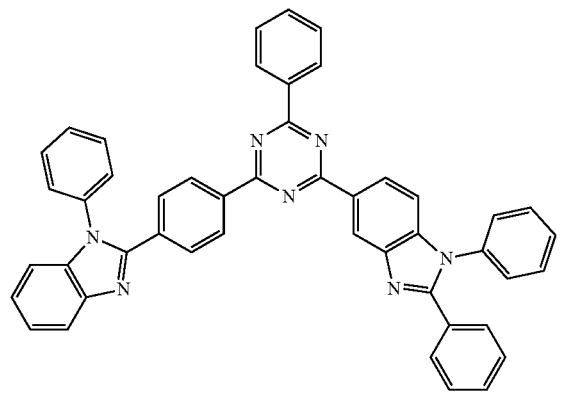 [SMILES: c1ccc(-c2nc(-c3ccc(-c4nc5ccccc5n4-c4ccccc4)cc3)nc(-c3ccc4c(c3)nc(-c3ccccc3)n4-c3ccccc3)n2)cc1]
(53)
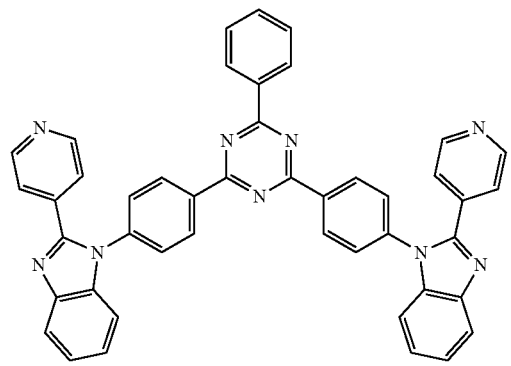
(54)
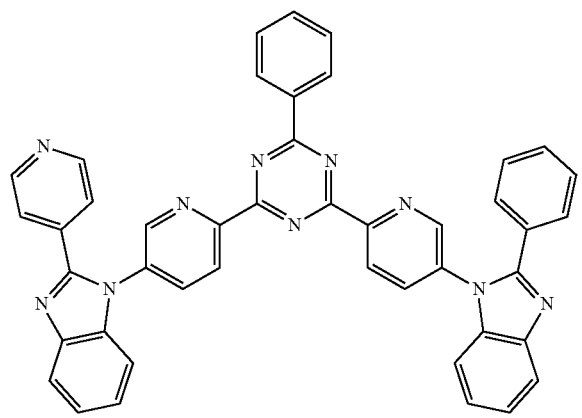
(55)
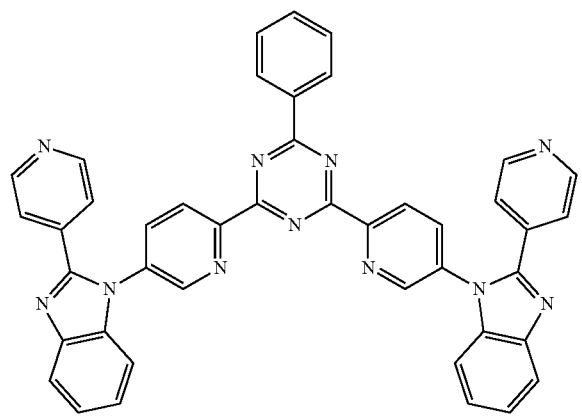
(56)

-continued
(57)
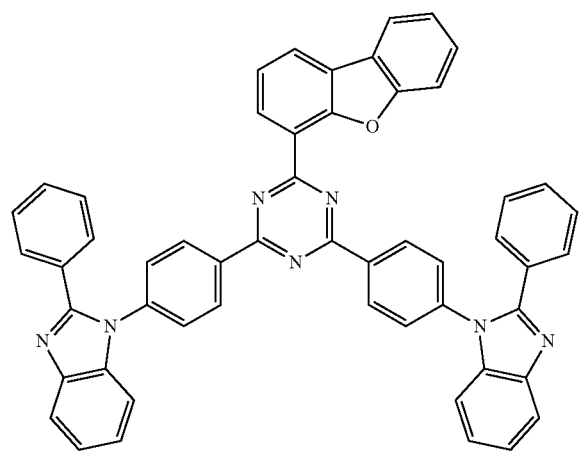
(58)
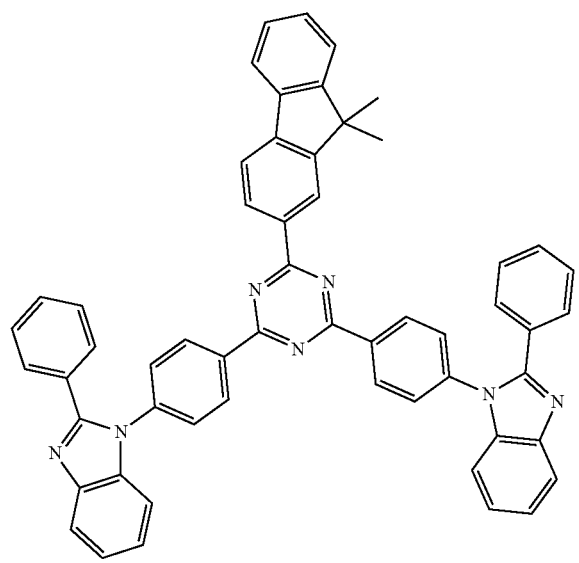
(59)
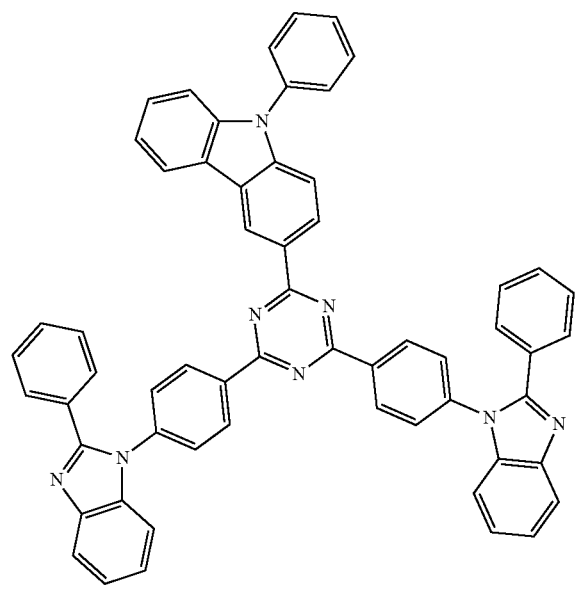
(60)
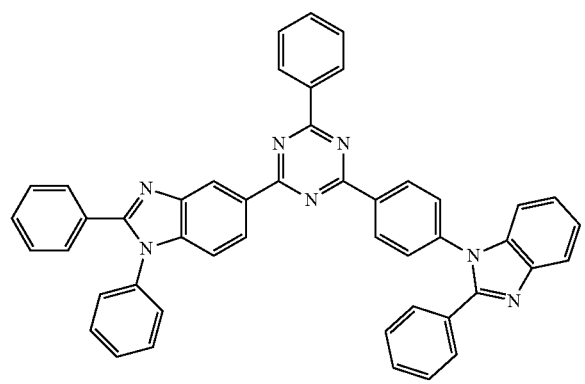

-continued
(61)
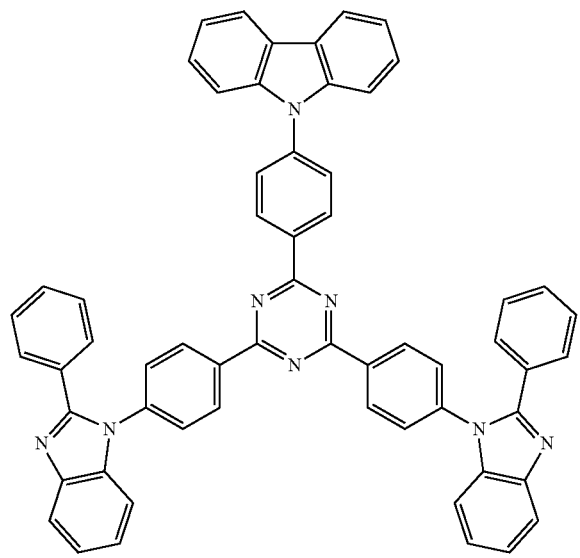
(62)
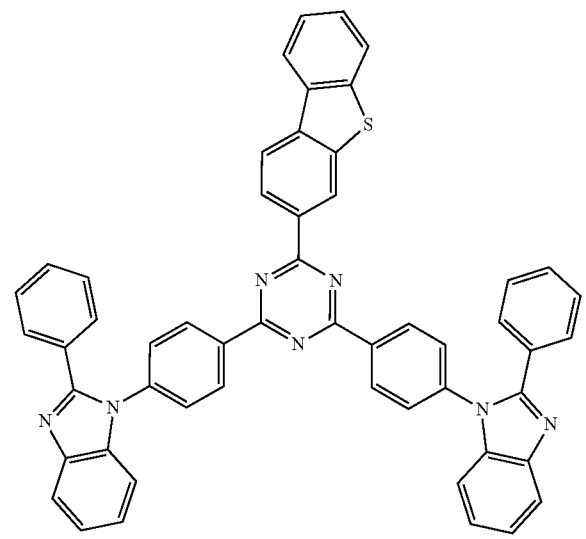
(63)
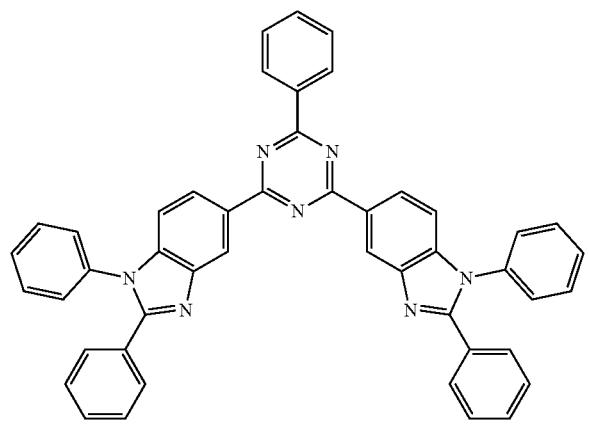
(64)
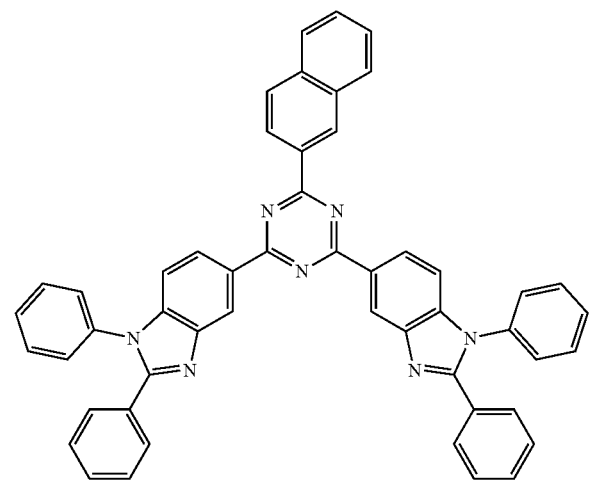
(65)
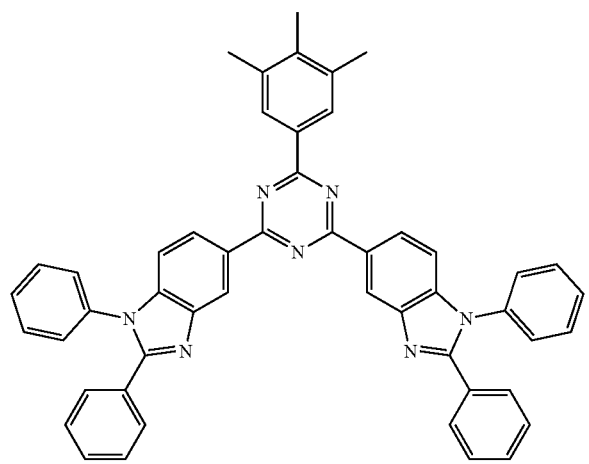
(66)
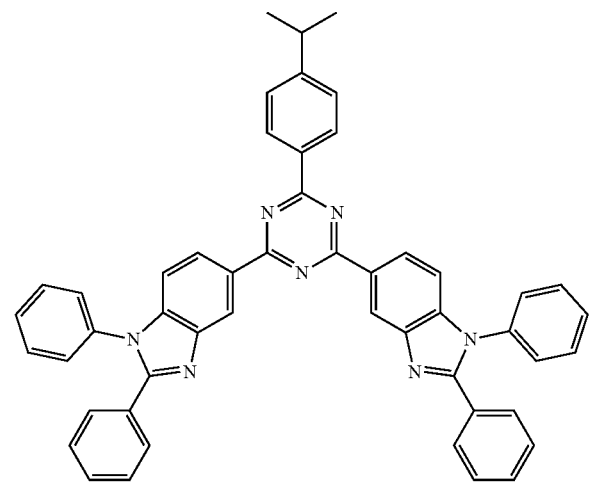

-continued
(67)
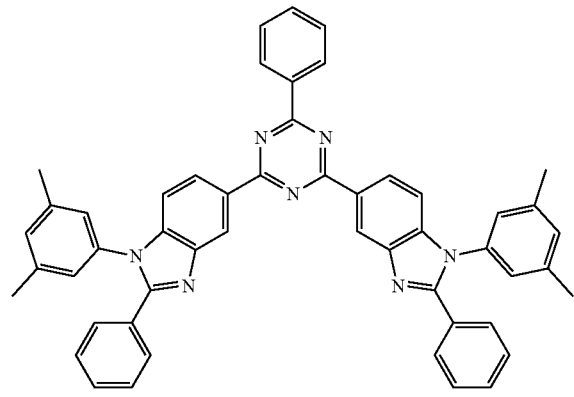
(68)
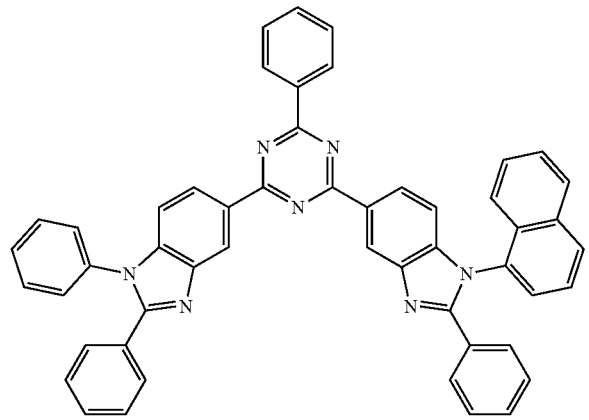
(69)
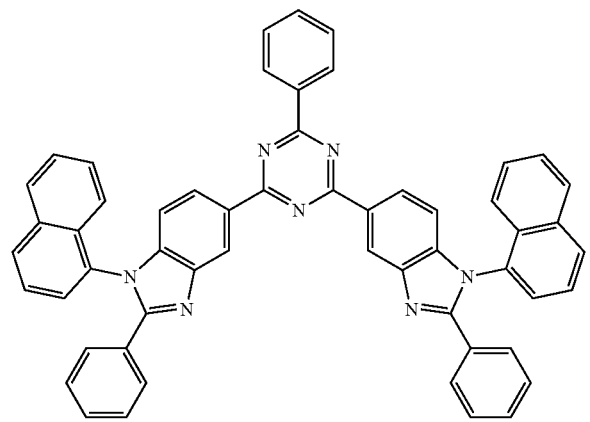
(70)
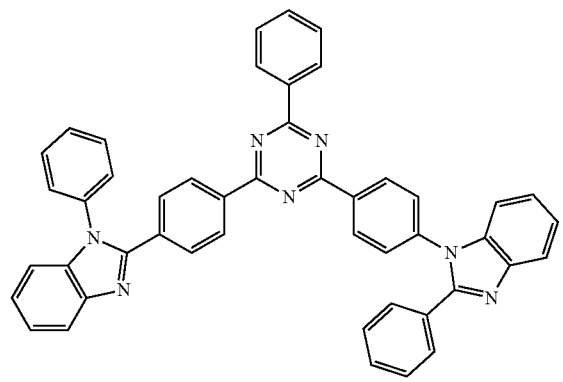 [SMILES: c1ccc(-c2nc(-c3ccc(-c4nc5ccccc5n4-c4ccccc4)cc3)nc(-c3ccc(-n4c(-c5ccccc5)nc5ccccc54)cc3)n2)cc1]
(71)
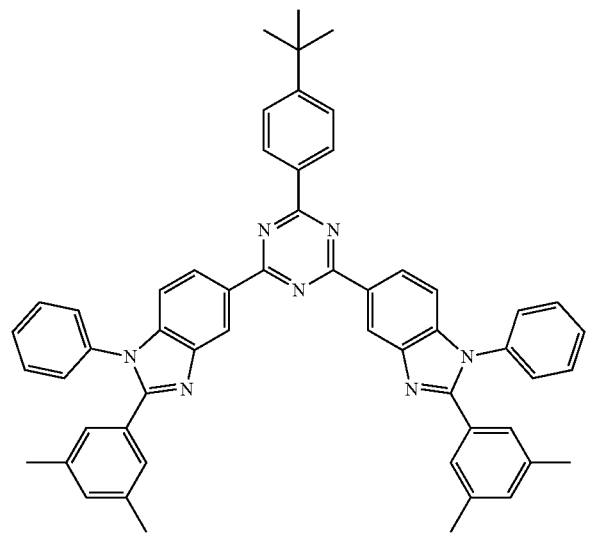
(72)
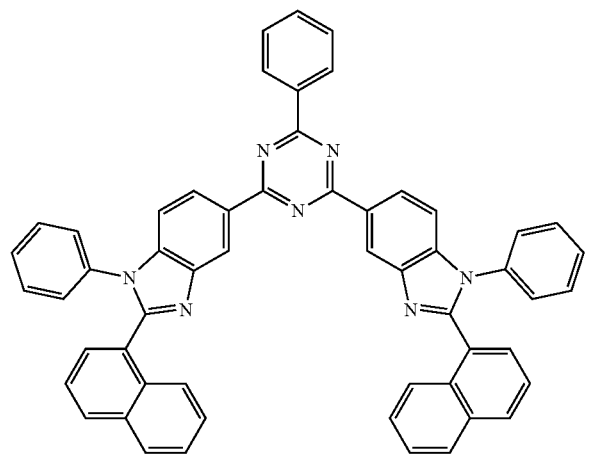

-continued
(73)
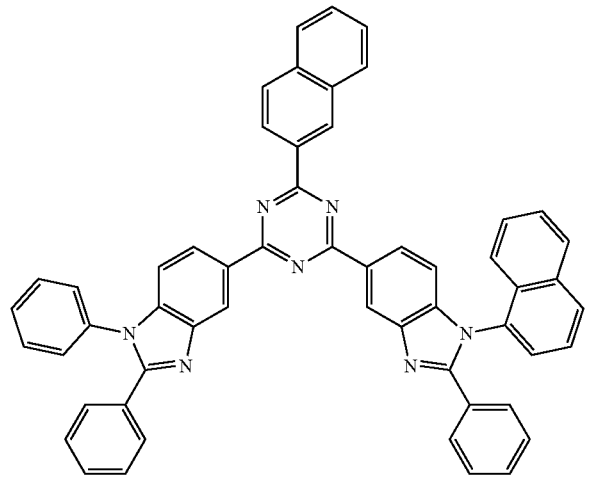
(74)
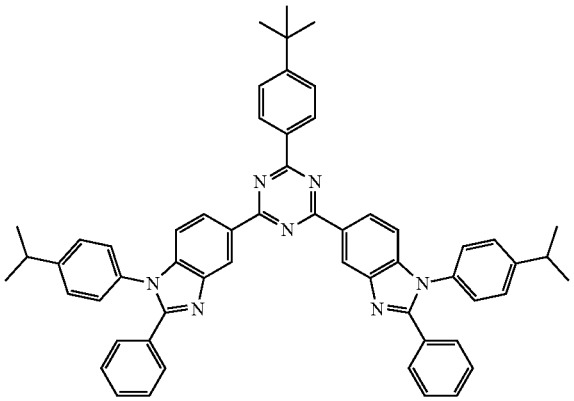
(75)
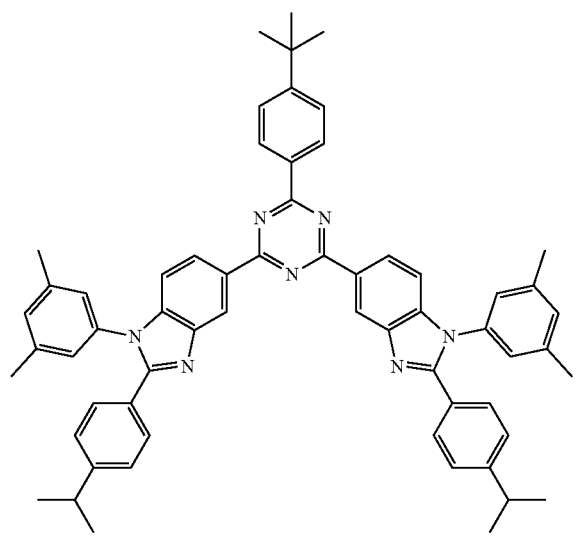
(76)
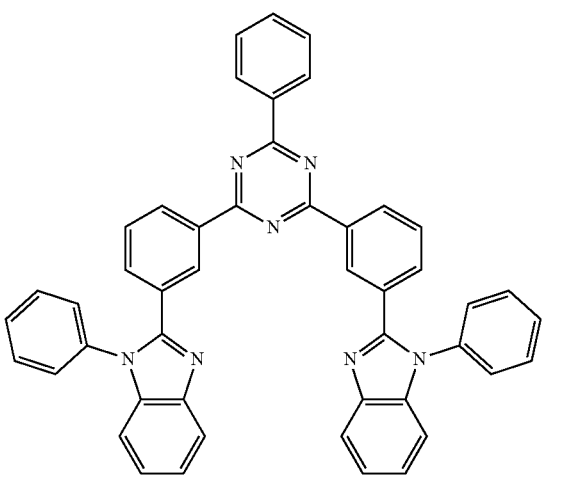
(77)
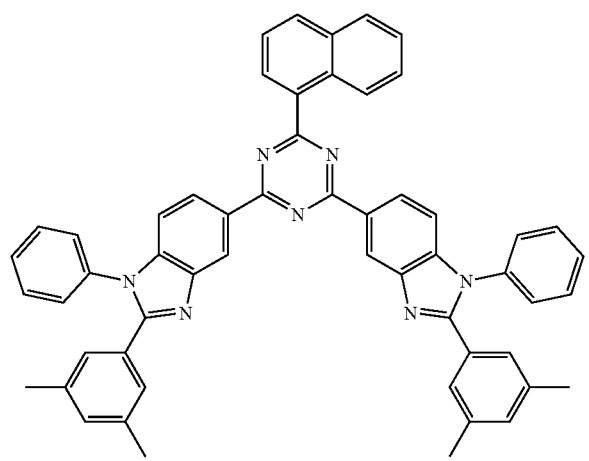
(78)
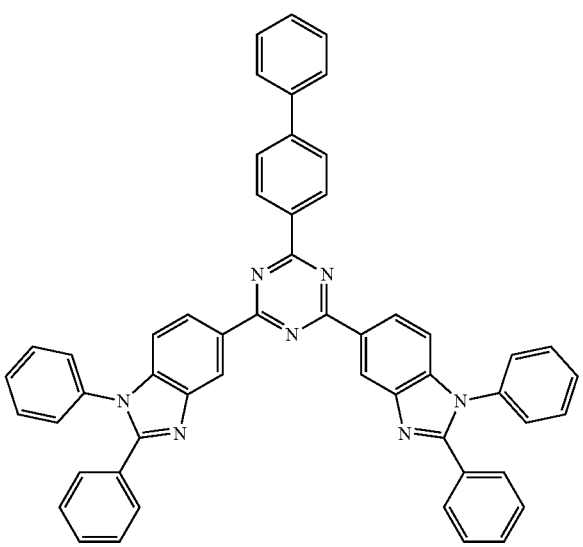

-continued
(79)
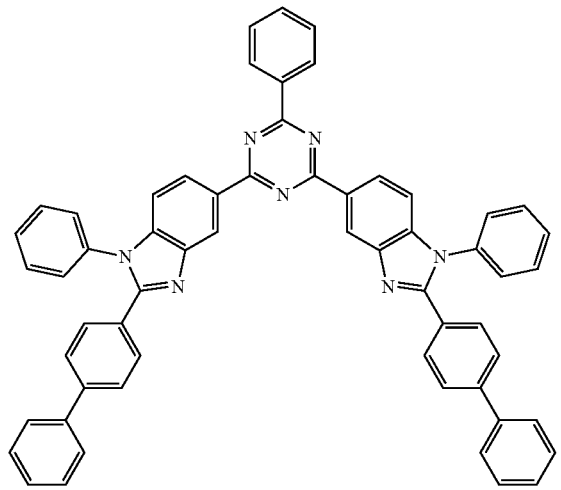
(80)
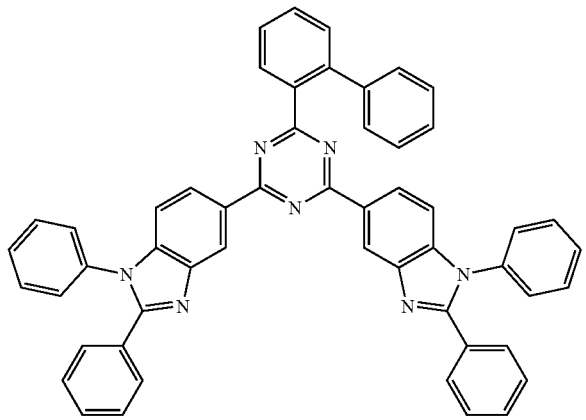
(81)
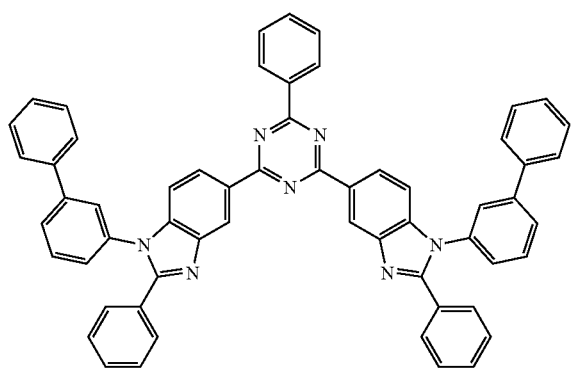
(82)
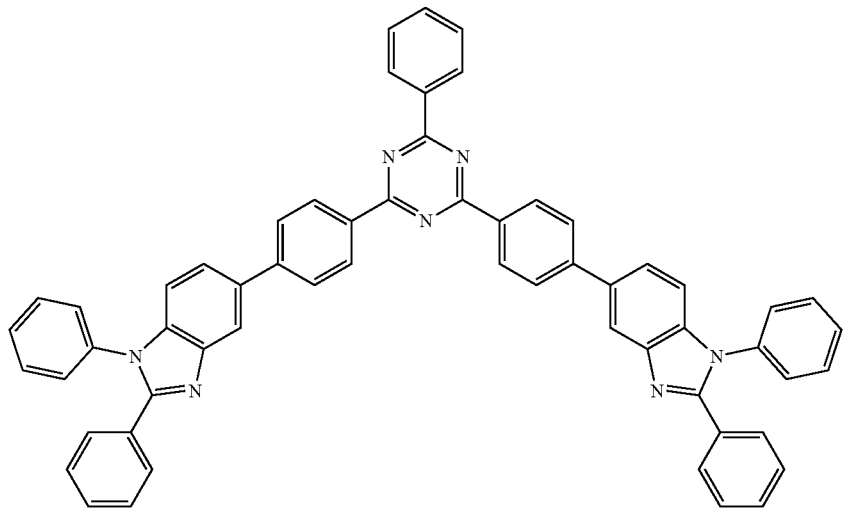

-continued
(83)
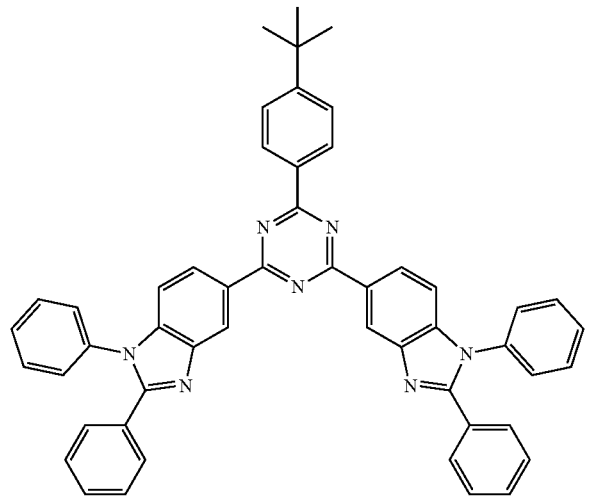
(84)
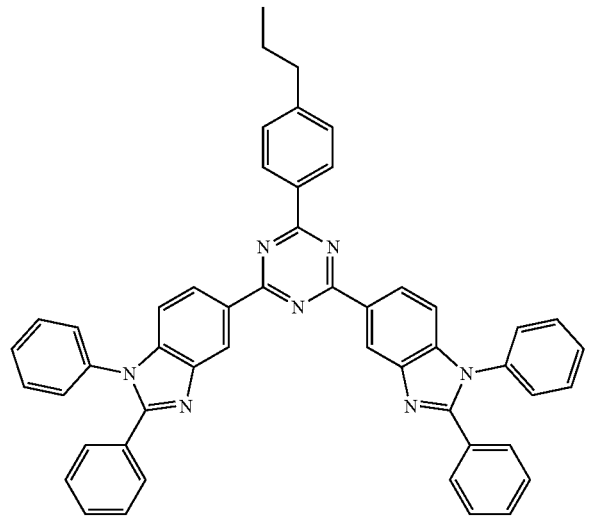
(85)
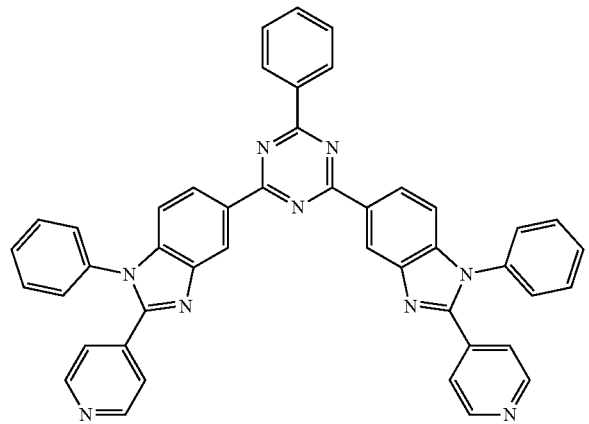
(86)
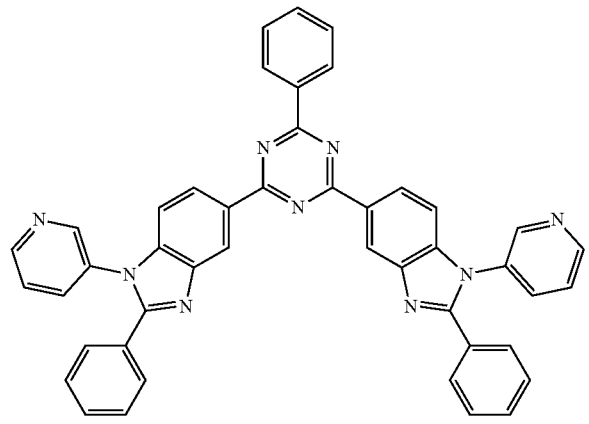
(87)
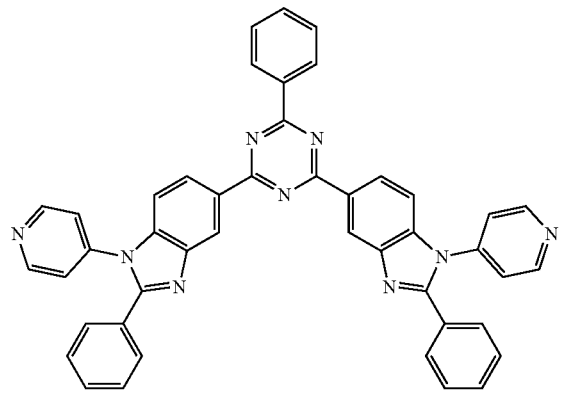
(88)
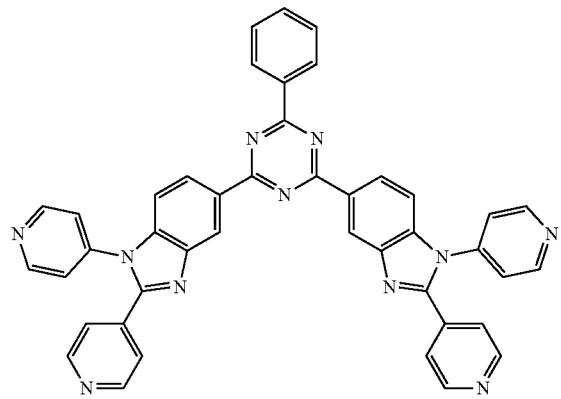

-continued
(89)
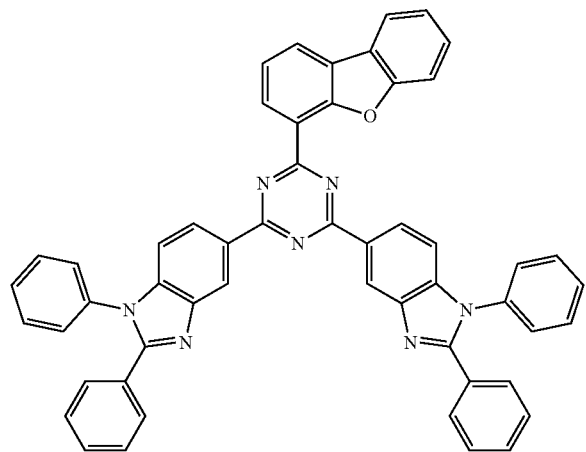
(90)
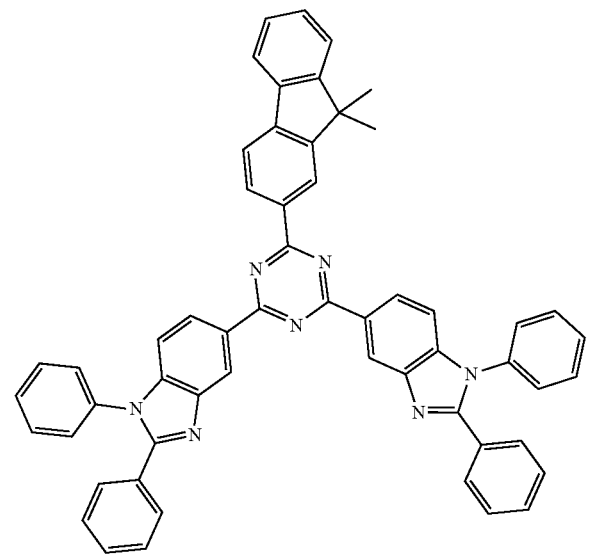
(91)
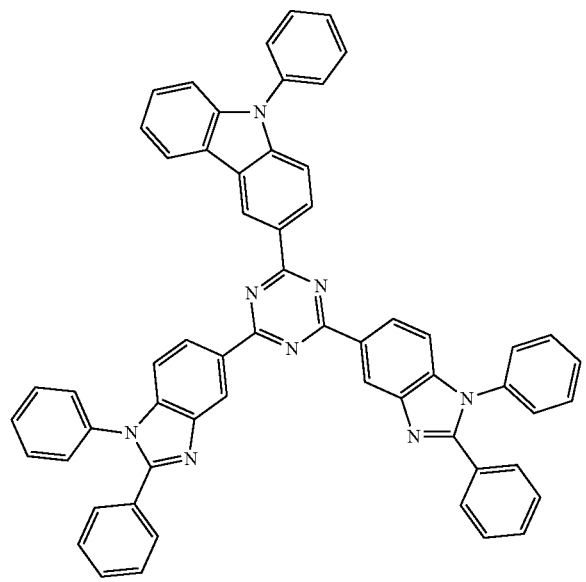
(92)
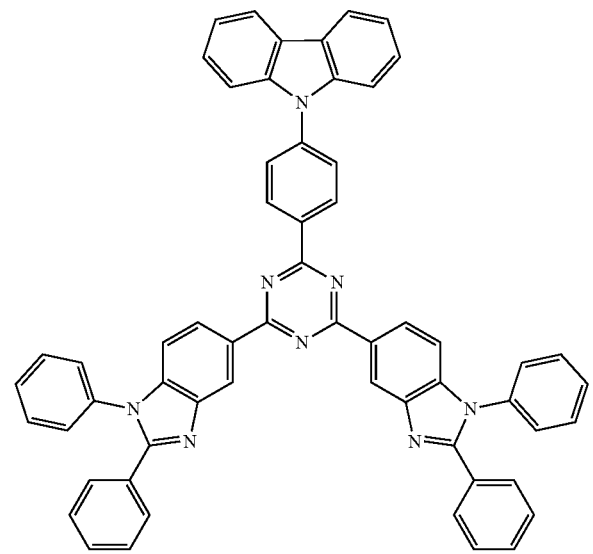
(93)
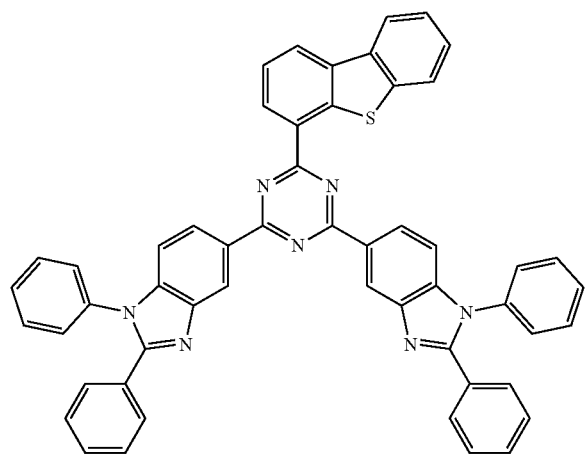
(94)
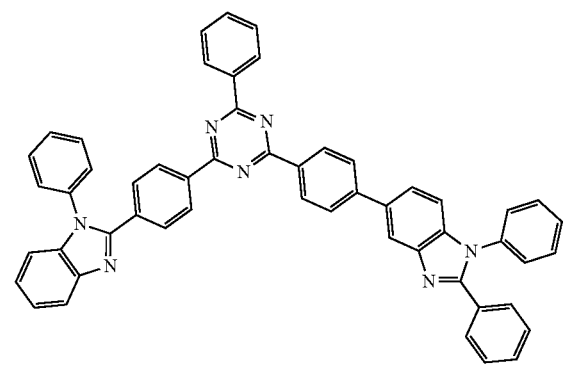

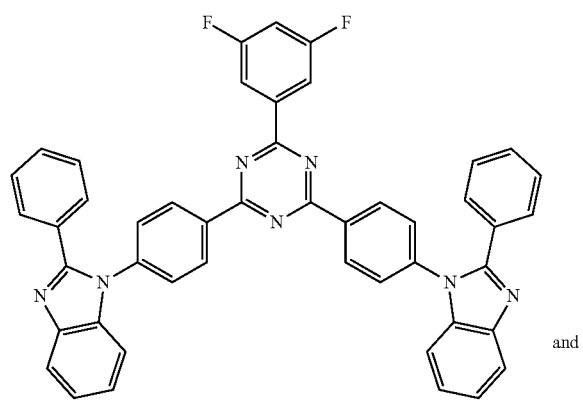 and 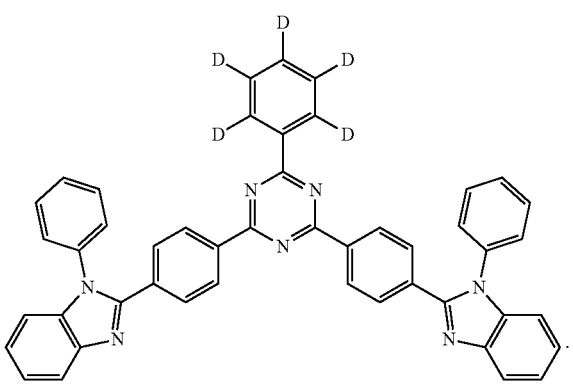.

3. A preparation method of the organic compound according to claim 1, wherein, reaction equations occurring in a preparation process are as follows:

a specific reaction process is:

step one: in a nitrogen atmosphere, weighing and dissolving a raw material, 2,4,6-trichloro-1,3,5-triazine in a tetrahydrofuran to obtain a first mixture, then adding a boronic acid compound of $Ar_1$ and tetrakis (triphenylphosphine) palladium to obtain a second mixture, stirring the second mixture and then adding a saturated aqueous potassium carbonate solution to obtain a first mixed solution, heating and refluxing the first mixed solution containing the above reactants for 10-20 hours at a reaction temperature of 70 to 90° C. to obtain a second mixed solution; after completion of the reaction, cooling, and extracting the second mixed solution with a dichloromethane to obtain a extract, drying the extract over a anhydrous sodium sulfate and concentrating under a reduced pressure to obtain a concentrated solid, and purifying the concentrated solid using a silica gel column to obtain a compound intermediate I;

wherein, a molar ratio of 2,4,6-trichloro-1,3,5-triazine to $Ar_1$-$B(OH)_2$ is 1:1.0-1.5, a molar ratio of $Pd(PPh_3)_4$ to 2,4,6-trichloro-1,3,5-triazine is 0.005-0.05:1, a molar ratio of $K_2CO_3$ to 2,4,6-trichloro-1,3,5-triazine is 1.0-2.0:1, a dosage of THF is: 2,4,6-trichloro-1,3,5-triazine: 1 g: 10-20 mL; wherein a reaction equation of the step one is

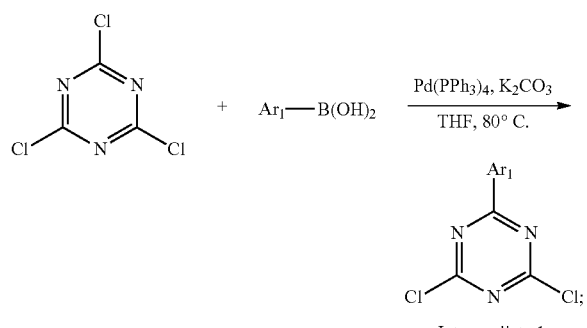

step two: in a nitrogen atmosphere, weighing and dissolving the intermediate I in N,N-dimethylformamide, then adding

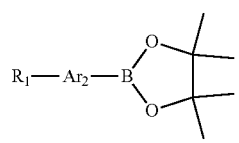

and palladium acetate to obtain a first mixture, stirring the mixture and then adding an aqueous potassium phosphate solution to obtain a mixed solution, heating and refluxing the mixed solution containing the above reactants for 10-24 hours at a reaction temperature of 120 to 150° C. to obtain a second mixture; after completion of the reaction, cooling, adding water, filtering and drying the second mixture in a vacuum drying oven to obtain a residue, and purifying the residue using a silica gel column to obtain a compound intermediate II;

wherein, a molar ratio of the intermediate I to

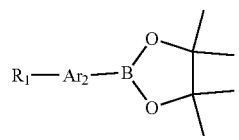

is 1:1.0-1.5, a molar ratio of $Pd(OAc)_2$ to the intermediate I is 0.001-0.02:1, a molar ratio of $K_3PO_4$ to the intermediate I is 1.0-2.0:1, a dosage of DMF is: the intermediate I: DMF=1 g: 10-20 mL;

wherein a reaction equation of the step two is

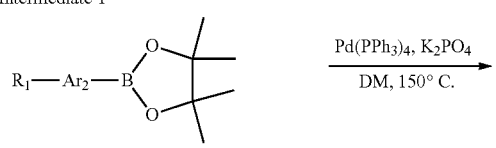

-continued

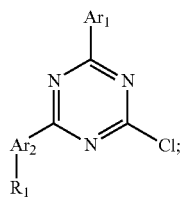

Intermediate II step three: in a nitrogen atmosphere, weighing and dissolving the intermediate II in N,N-dimethylformamide, then adding

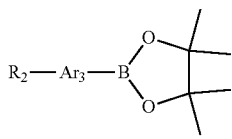

and palladium acetate to obtain a first mixture, stirring the mixture and then adding an aqueous potassium phosphate solution to obtain a mixed solution, heating and refluxing the mixed solution containing the above reactants for 10-24 hours at a reaction temperature of 120 to 150° C. to obtain a second mixture; after completion of the reaction, cooling, adding water, filtering and drying the second mixture in a vacuum drying oven to obtain a residue, and purifying the residue using a silica gel column to obtain a target compound;

wherein, a molar ratio of the intermediate II to

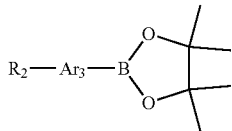

is 1:1.0-1.5, a molar ratio of $Pd(OAc)_2$ to the intermediate II is 0.001-0.02:1, he a molar ratio of $K_3PO_4$ to the intermediate II is 1.0-2.0:1, a dosage of DMF is: the intermediate II: DMF=1 g: 15-30 mL;

wherein a reaction equation of the step three is

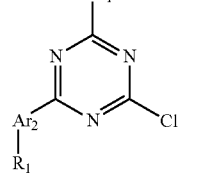

Intermediate II

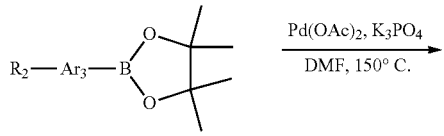

-continued

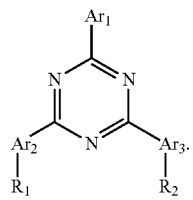

4. An organic electroluminescent device prepared by an organic compound with triazine and benzimidazole as a core, wherein a structure of the organic compound is represented by the following formula (1):

formula (1)

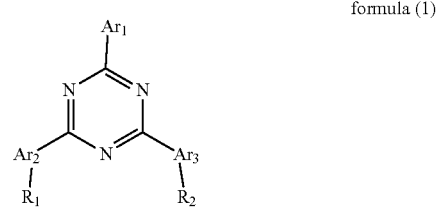

and wherein, $Ar_1$ is one selected from the group consisting of phenyl, naphthyl, biphenyl, terphenyl, anthryl, dibenzofuranyl, dibenzothiophenyl, 9,9-dimethylfluorenyl or 9-phenylcarbazolyl, substituted or unsubstituted by halogen atoms, protium atoms, deuterium atoms, tritium atoms, and linear or branched alkyl with 1 to 10 carbons;

$Ar_2$ is a single bond or one selected from the group consisting of phenyl, naphthyl, biphenyl, terphenyl, anthryl or pyridyl, substituted or unsubstituted by halogen atoms, protium atoms, deuterium atoms, tritium atoms, and linear or branched alkyl with 1 to 10 carbons;

$Ar_3$ is a single bond or one selected from the group consisting of phenyl, naphthyl, biphenyl, terphenyl, anthryl or pyridyl, substituted or unsubstituted by halogen atoms, protium atoms, deuterium atoms, tritium atoms, and linear or branched alkyl with 1 to 10 carbons;

$R_1$ is one selected from the group consisting of formula (2), formula (3) and formula (4); $R_2$ is one selected from the group consisting of formula (2), formula (3) and formula (4); wherein formula (2), formula (3) and formula (4) are:

formula (2)

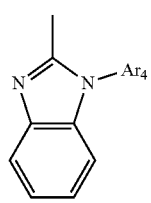

formula (3)

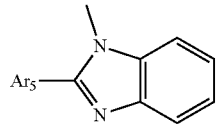

formula (4)

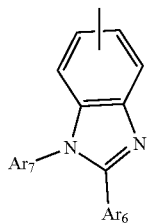

and wherein, Ar₄ is one selected from the group consisting of phenyl, naphthyl, biphenyl, terphenyl or pyridyl, substituted or unsubstituted by halogen atoms, and linear or branched alkyl with 1 to 10 carbons;

Ar₅ is one selected from the group consisting of phenyl, naphthyl, biphenyl, terphenyl or pyridyl, substituted or unsubstituted by halogen atoms, and linear or branched alkyl with 1 to 10 carbons;

Ar₆ is one selected from the group consisting of phenyl, naphthyl, biphenyl, terphenyl or pyridyl, substituted or unsubstituted by halogen atoms, and linear or branched alkyl with 1 to 10 carbons;

Ar₇ is one selected from the group consisting of phenyl, naphthyl, biphenyl, terphenyl or pyridyl, substituted or unsubstituted by halogen atoms, and linear or branched alkyl with 1 to 10 carbons.

5. The organic electroluminescent device according to claim 4, wherein the organic electroluminescent device comprises at least one functional layer containing the organic compound.

6. The organic electroluminescent device according to claim 4, wherein the organic electroluminescent device comprises a hole block layer or an electron transport layer; and wherein the hole block layer or the electron transport layer contains the organic compound.

7. The organic electroluminescent device according to claim 4, wherein the organic electroluminescent device comprises a CPL layer; and wherein the CPL layer contains the organic compound with triazine and benzimidazole as a core.

8. The organic electroluminescent device according to claim 4, wherein a particular structural formula of the organic compound is any one selected from the group consisting of:

(1)

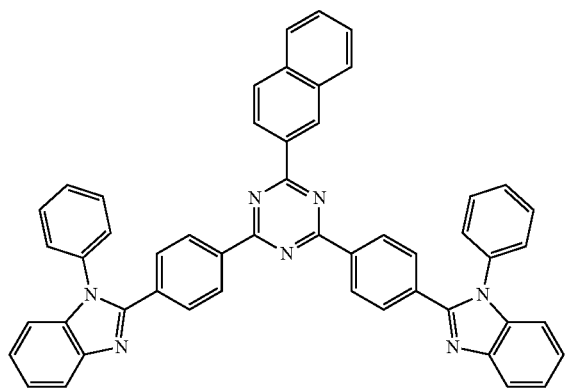

(2)

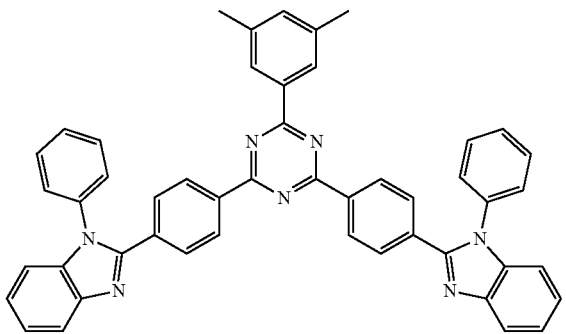

(3)

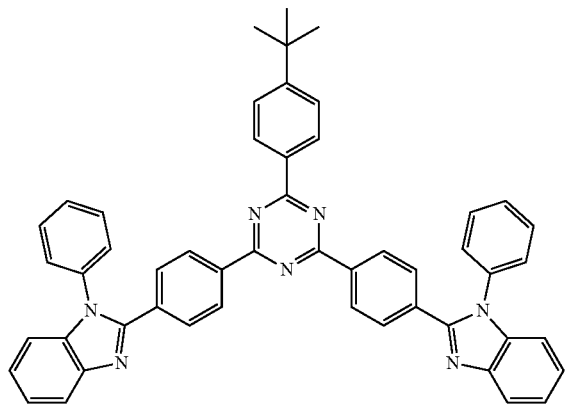

(4)

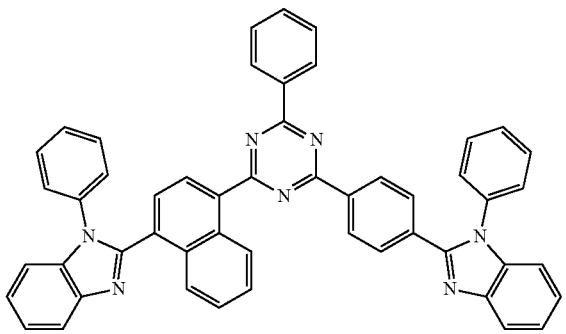

(5)
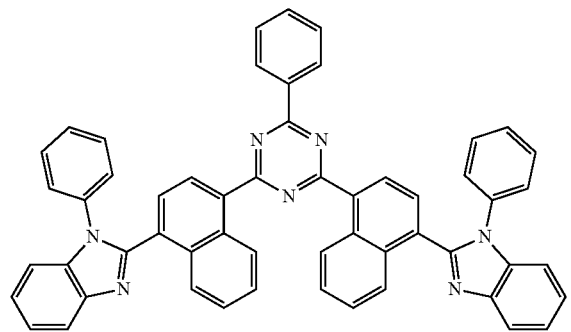
(6)
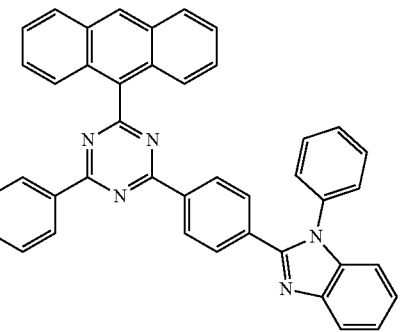
(7)
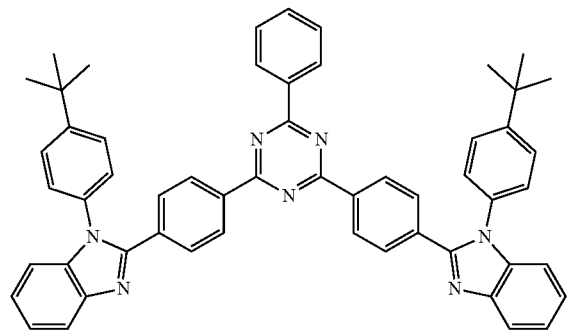
(8)
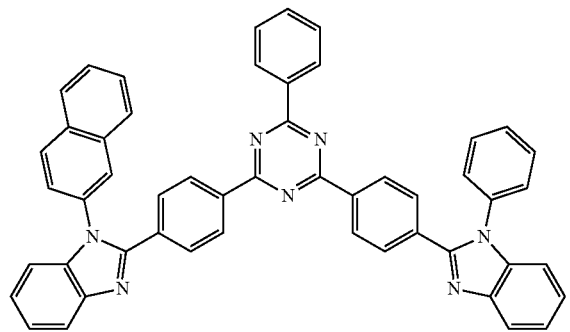
(9)
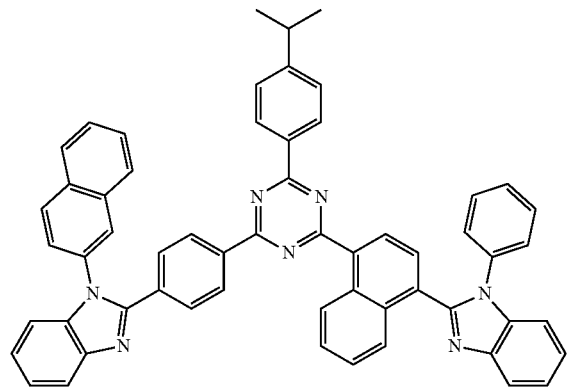
(10)
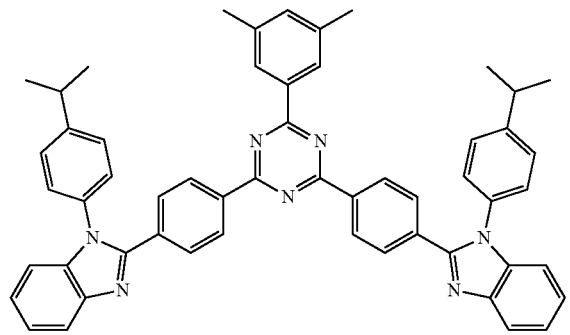
(11)
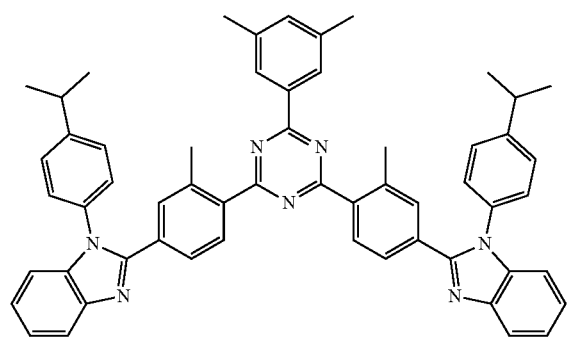
(12)
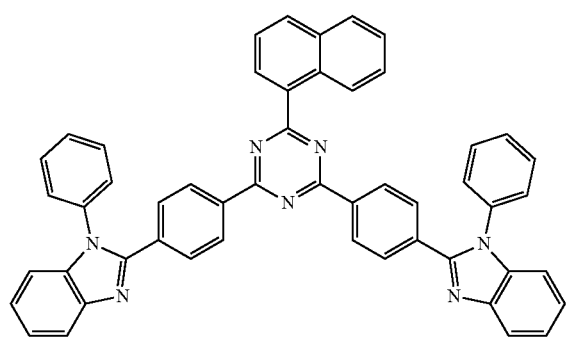

(13)
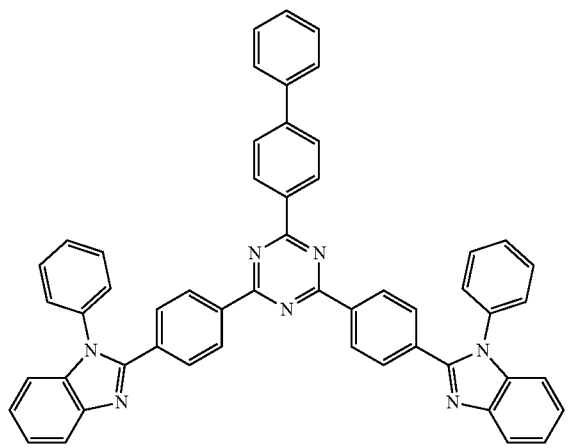
(14)
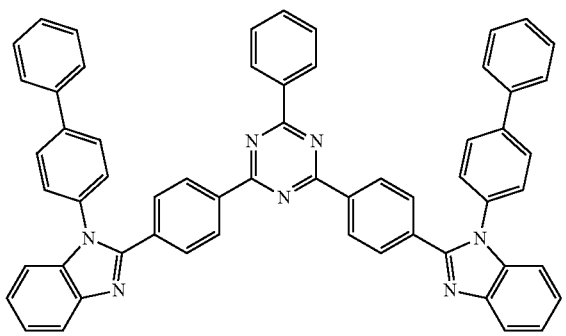
(15)
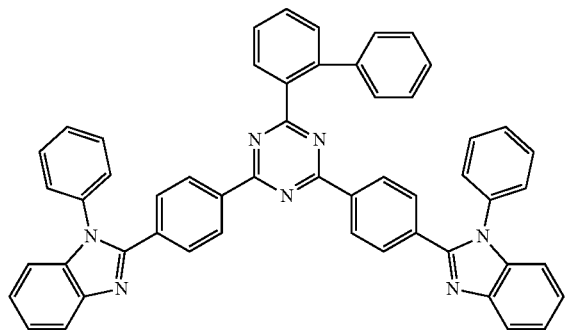
(16)
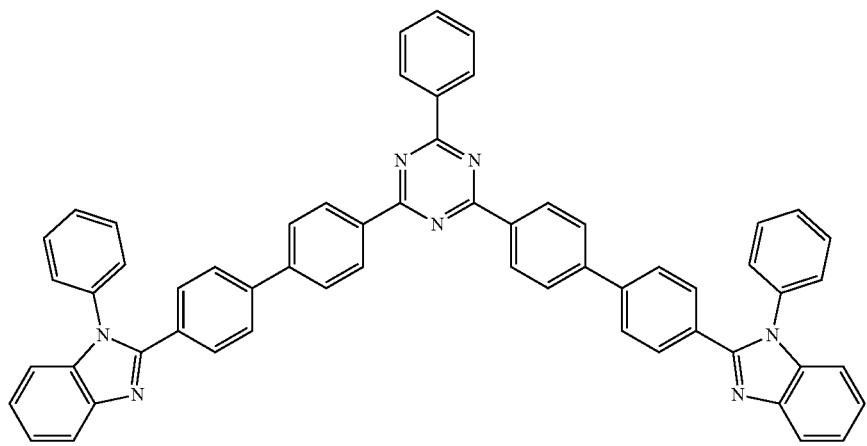

-continued
(17)
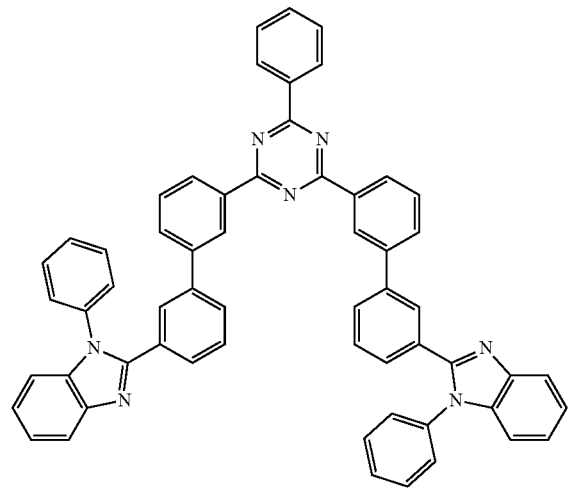
(18)
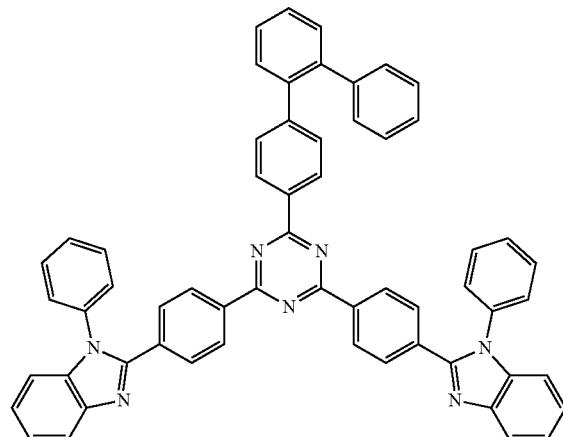
(19)
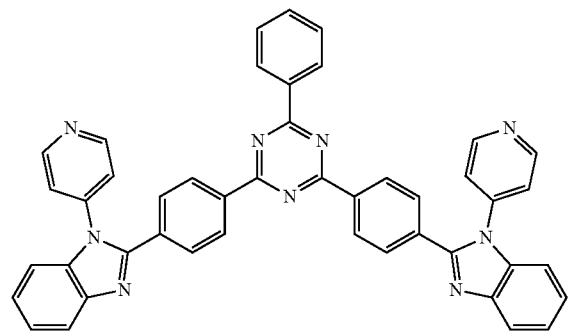
(20)
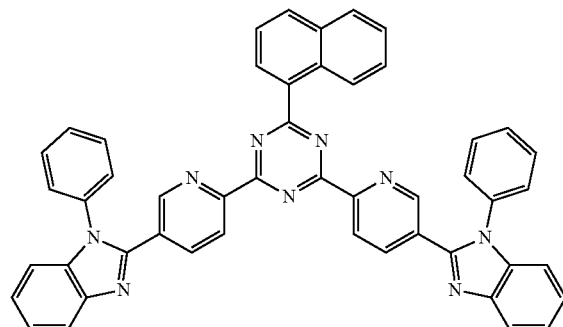
(21)
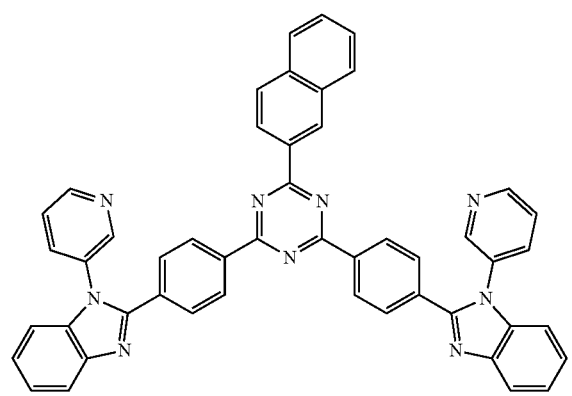
(22)
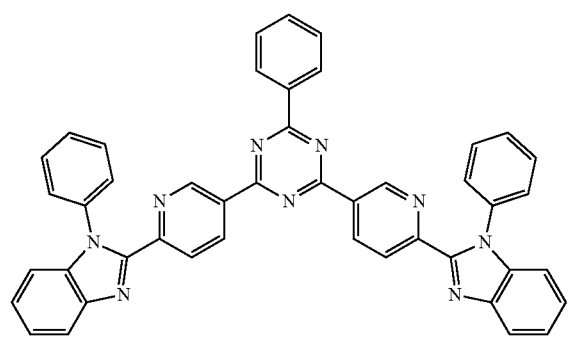

-continued
(23)
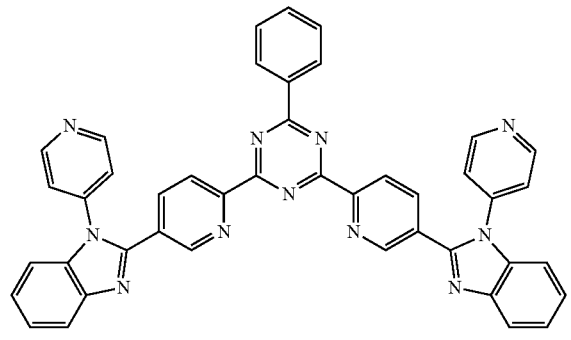
(24)
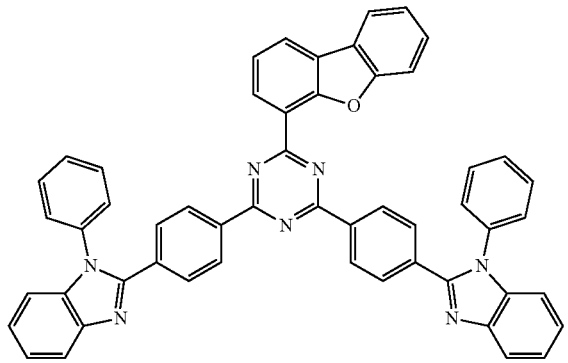
(25)
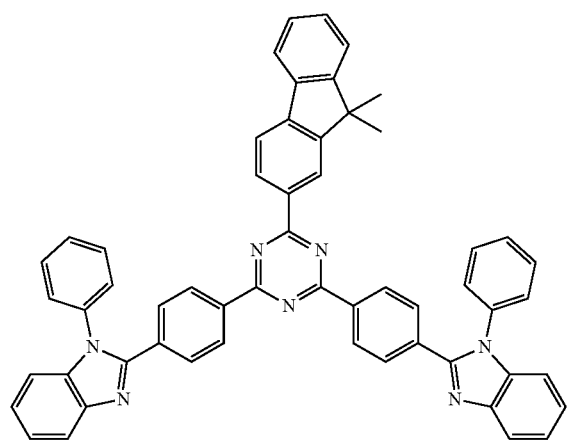
(26)
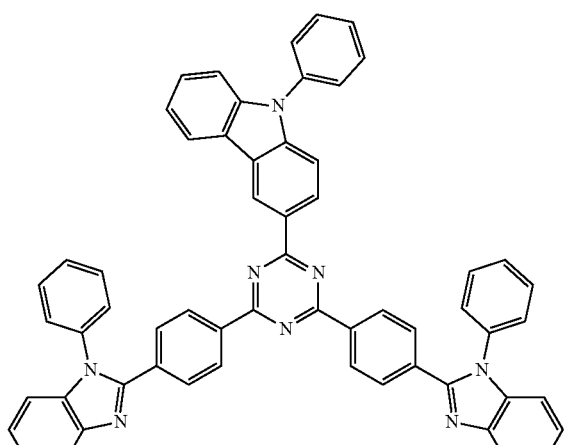
(27)
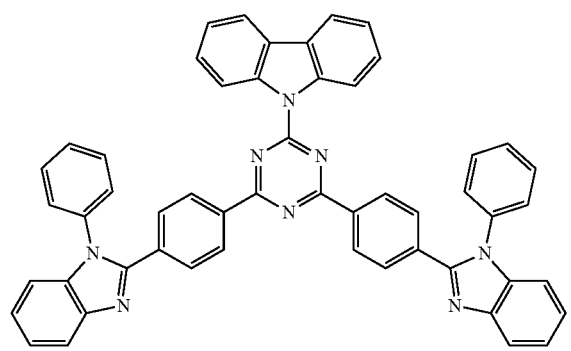
(28)
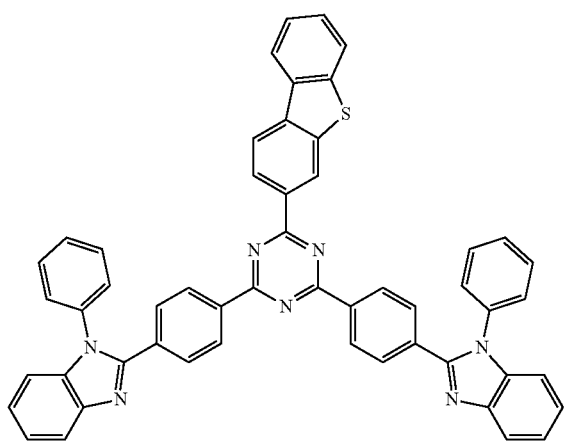

(29)
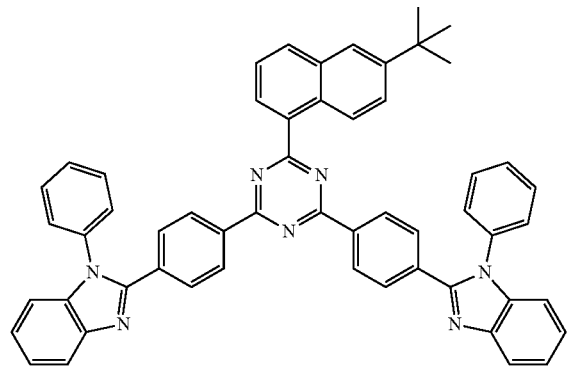
(30)
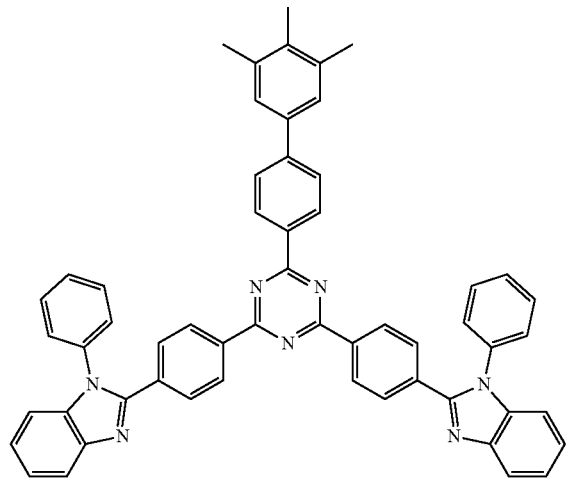
(31)
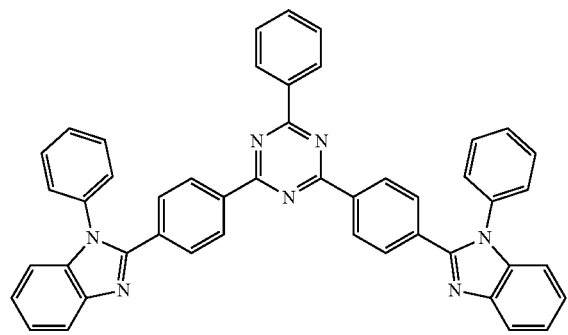
(32)
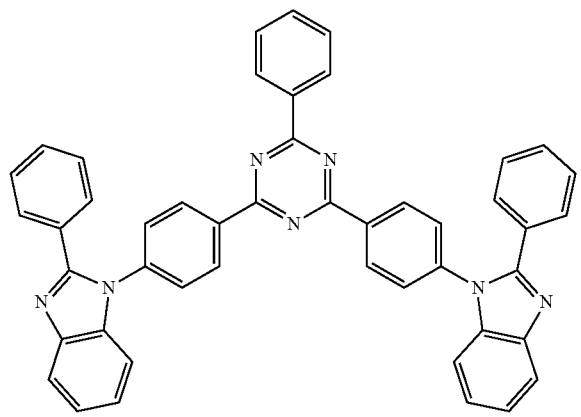
(33)
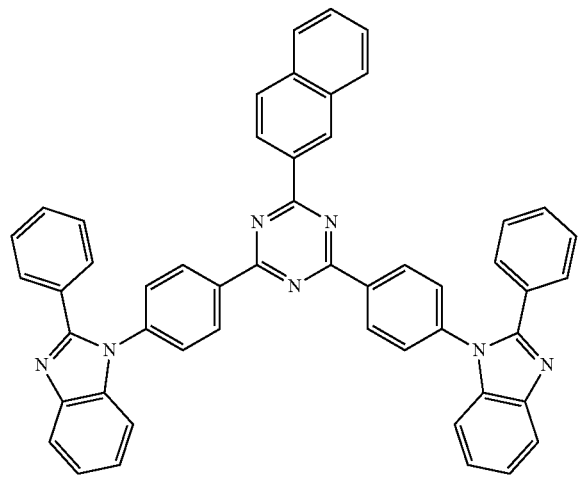
(34)
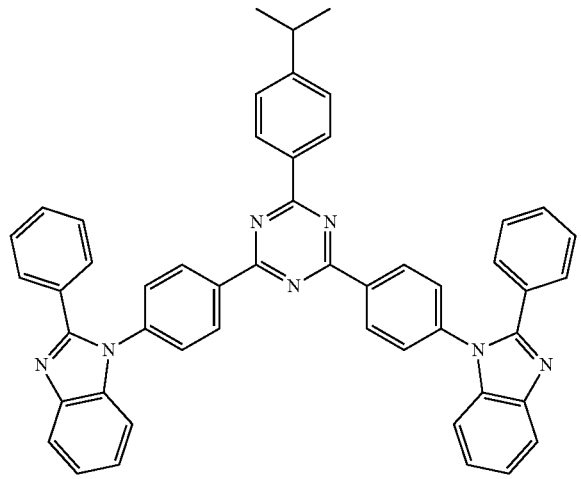

-continued
(35)
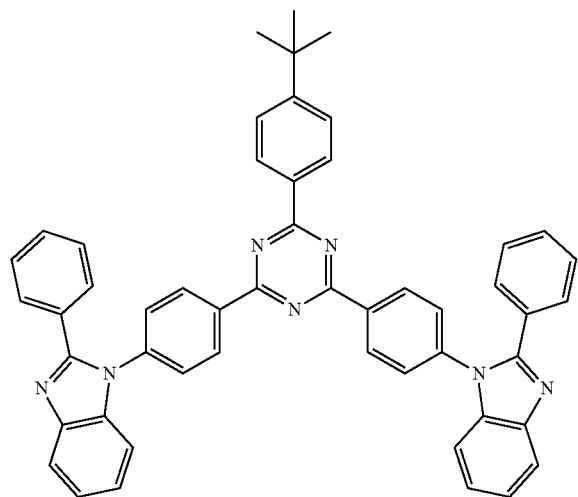
(36)
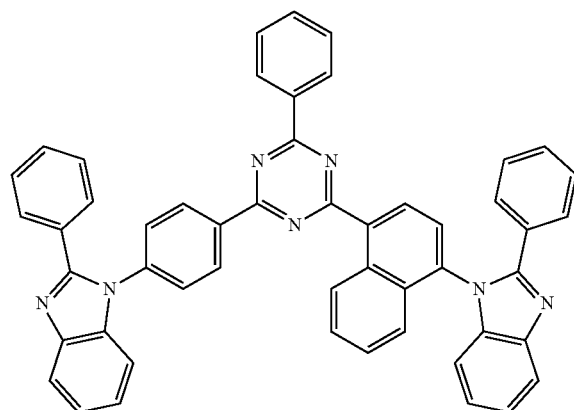
(37)
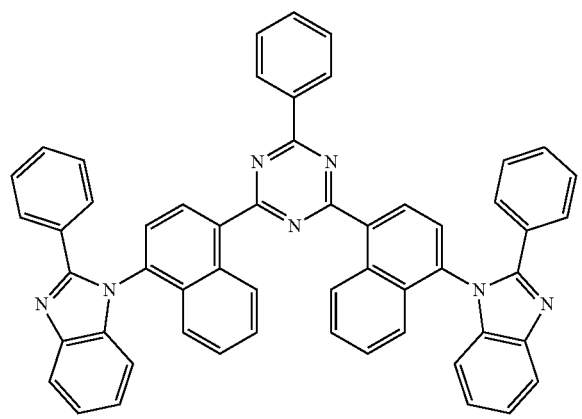
(38)
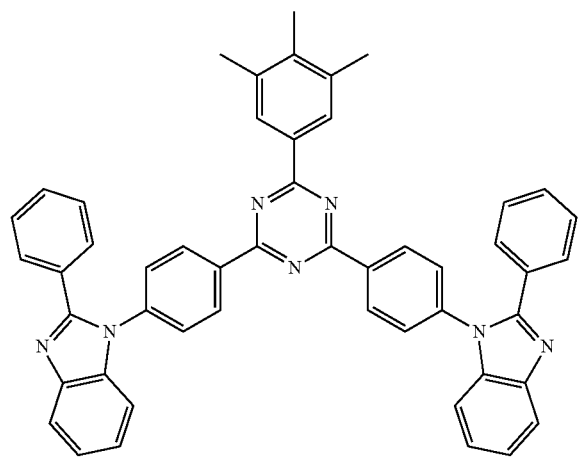
(39)
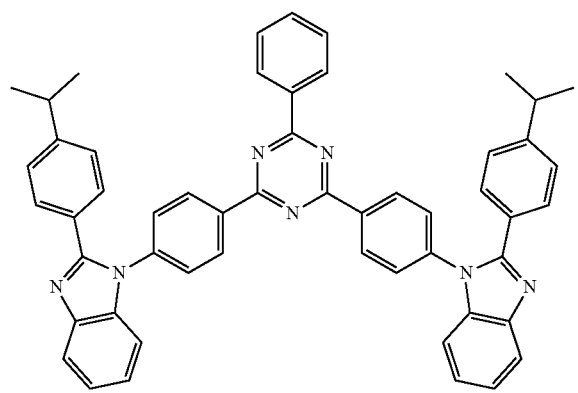
(40)
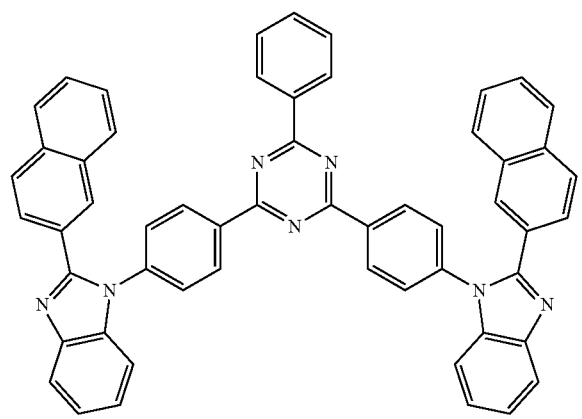

(41)
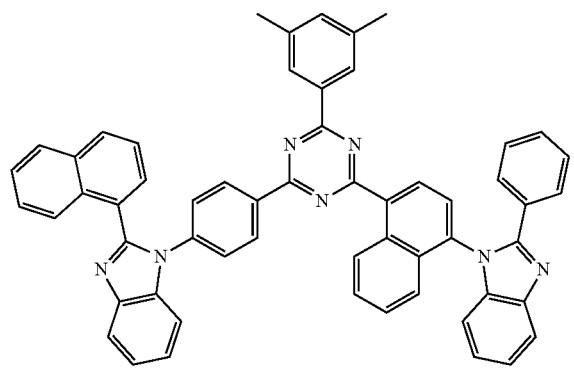
(42)
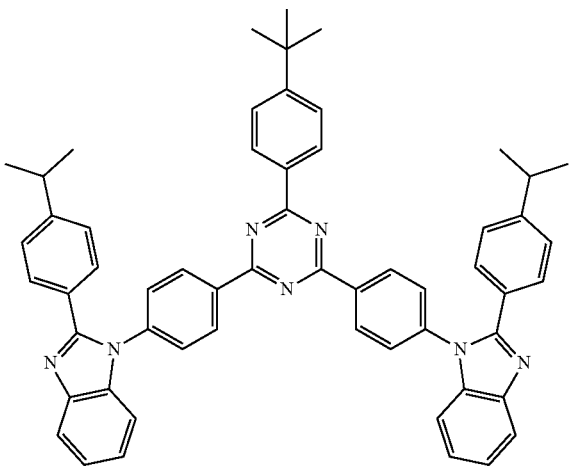
(43)
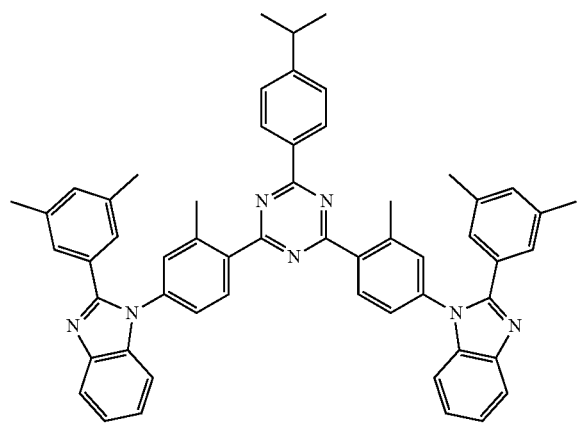
(44)
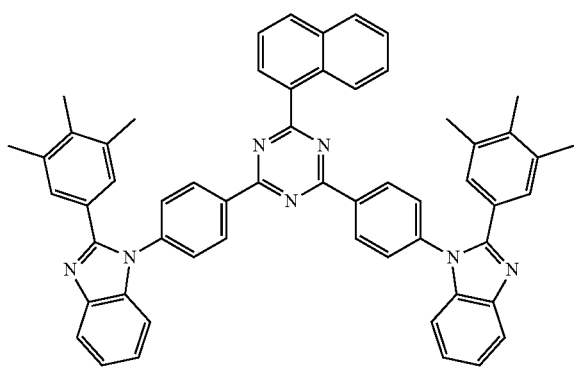
(45)
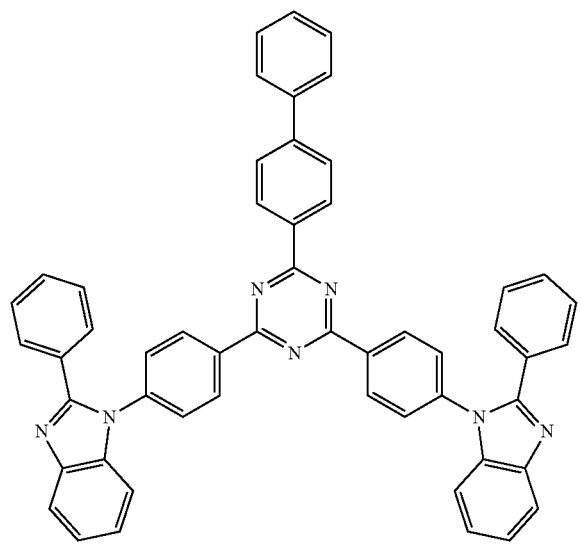
(46)
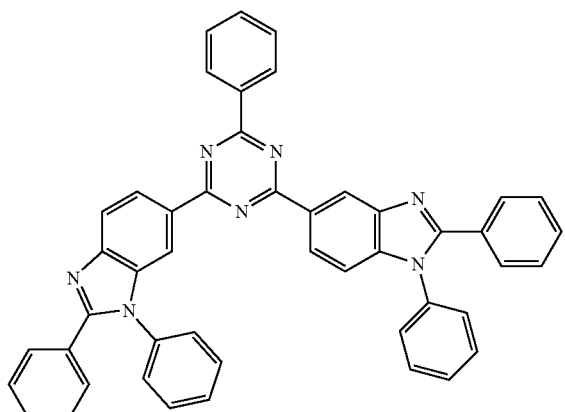

(47)
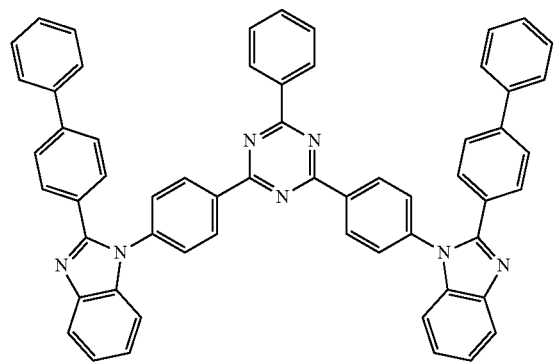
(48)
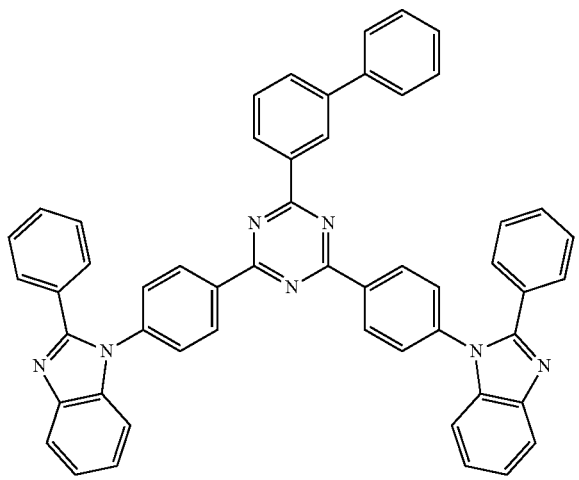
(49)
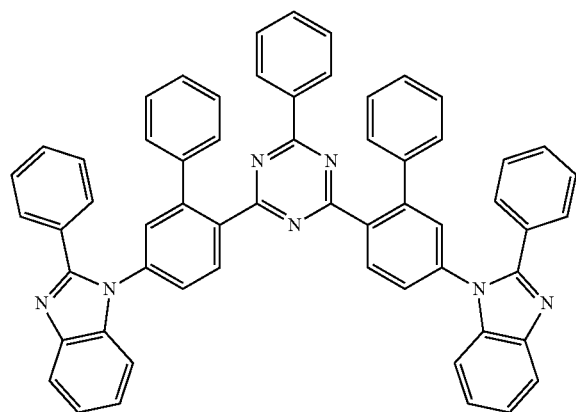
(50)
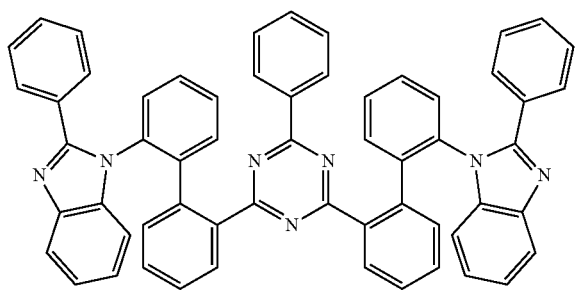
(51)
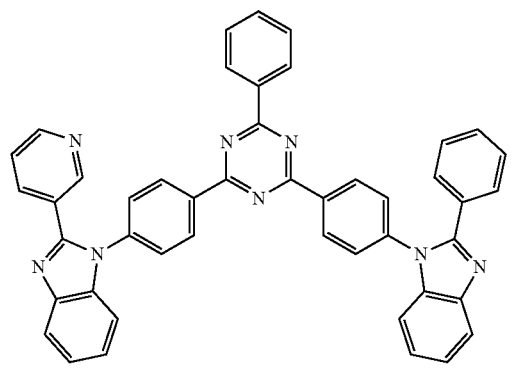
(52)
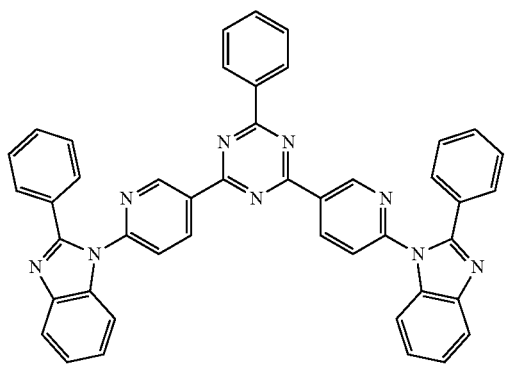

-continued
(53)
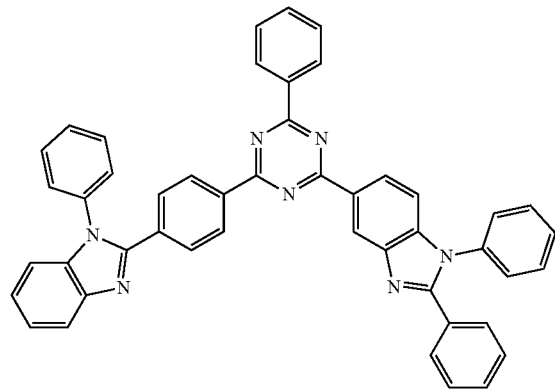
(54)
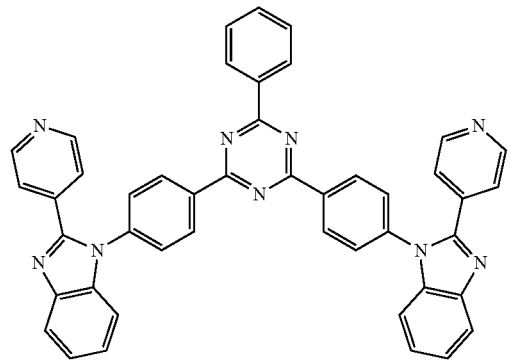
(55)
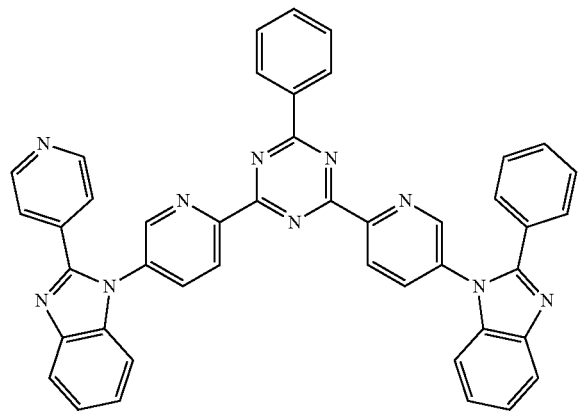
(56)
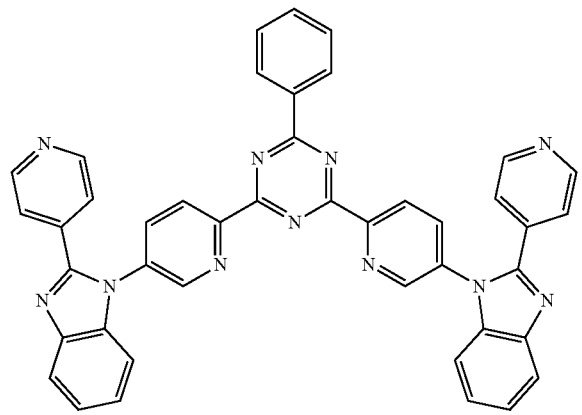
(57)
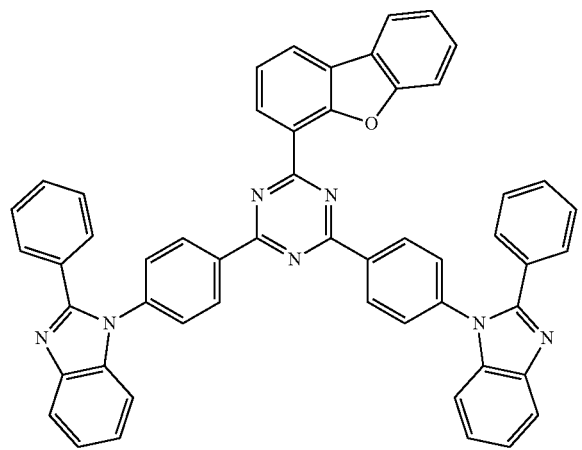
(58)
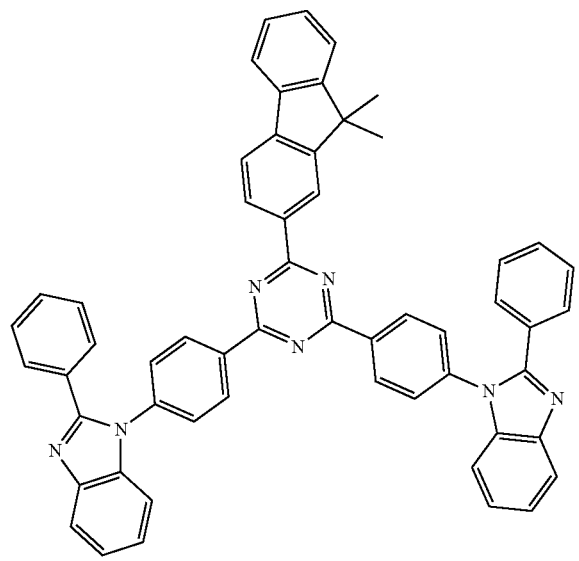

(59)
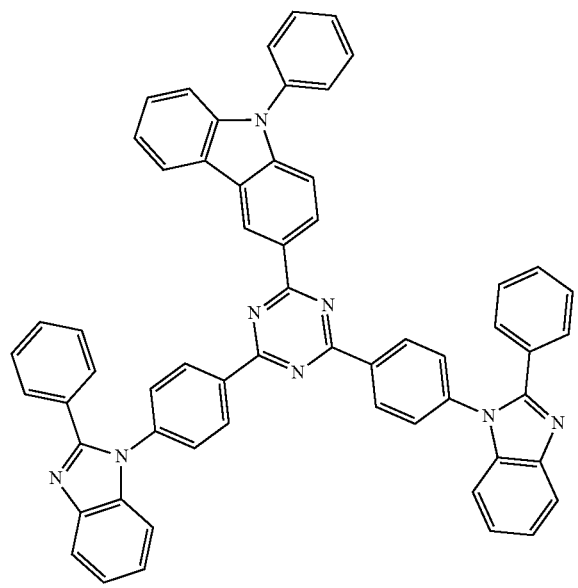
(60)
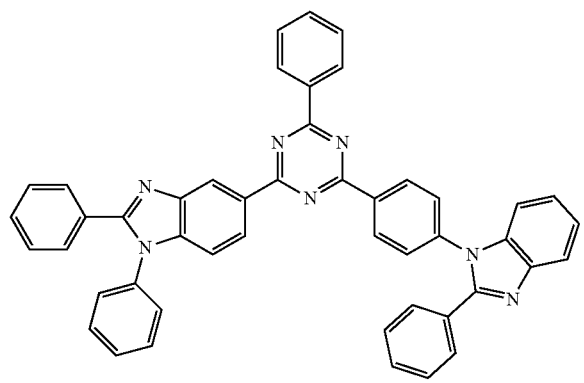
(61)
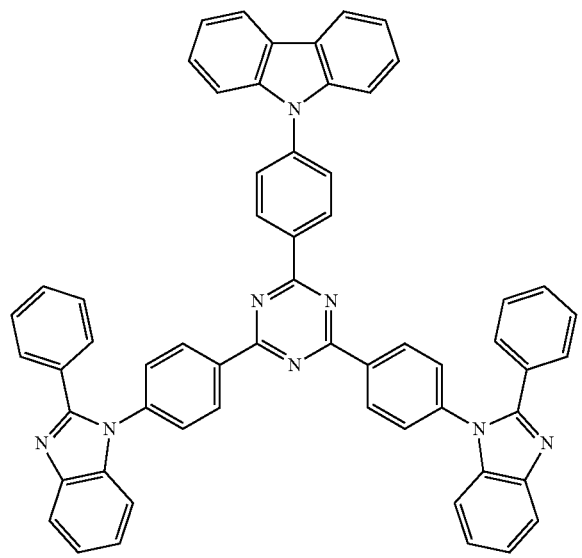
(62)
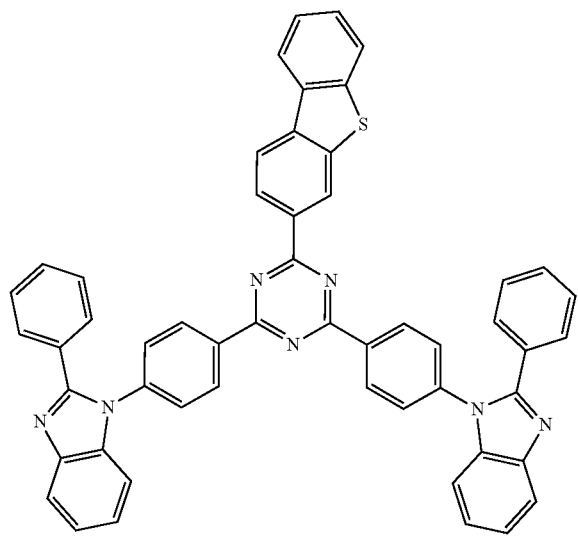

-continued
(63)
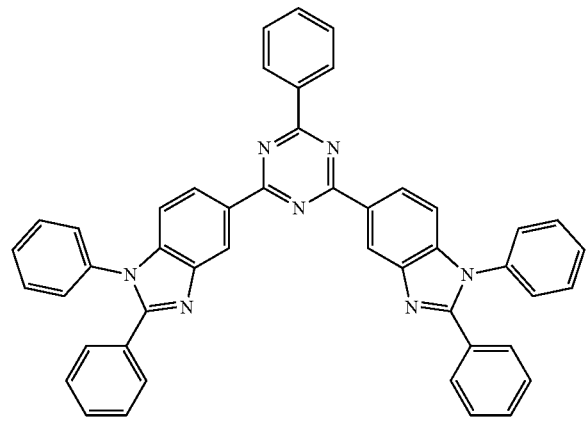
(64)
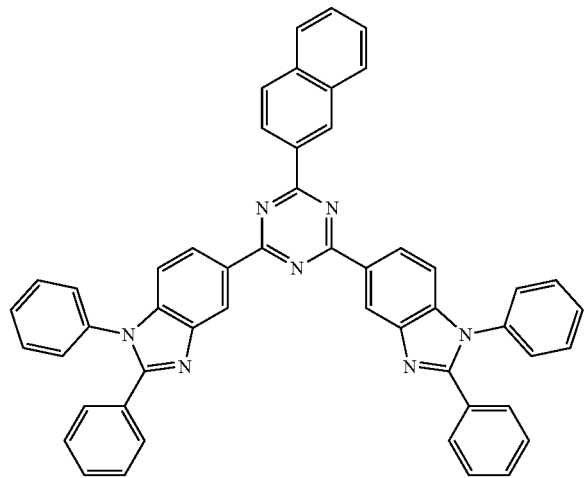
(65)
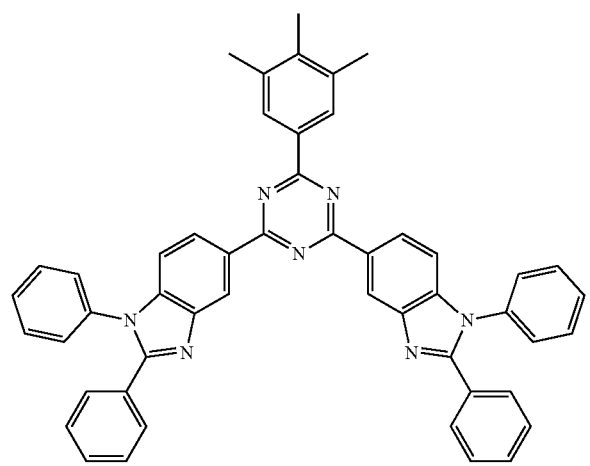
(66)
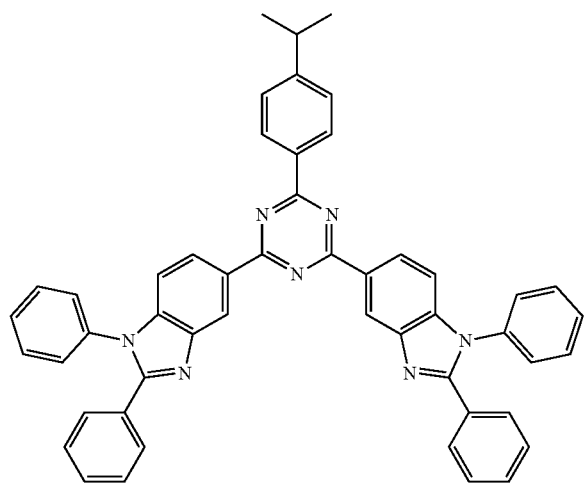
(67)
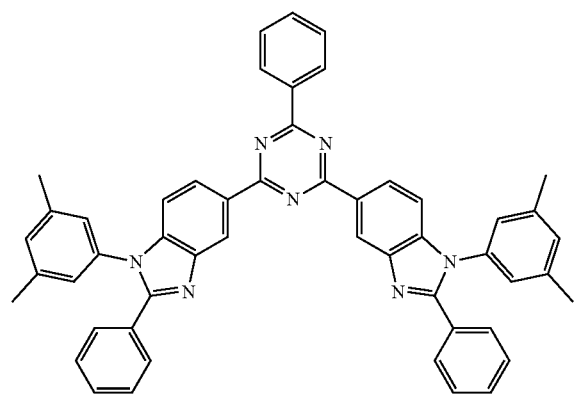
(68)
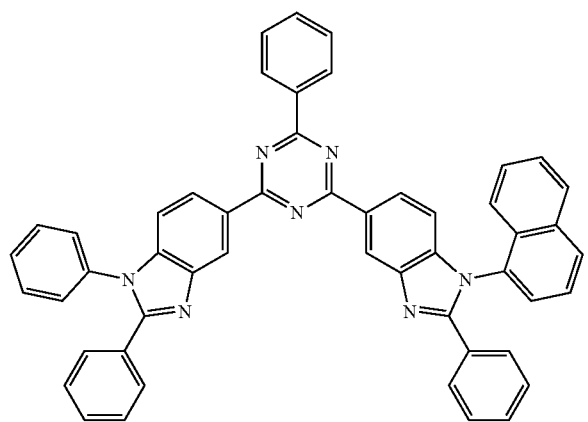

-continued
(69)
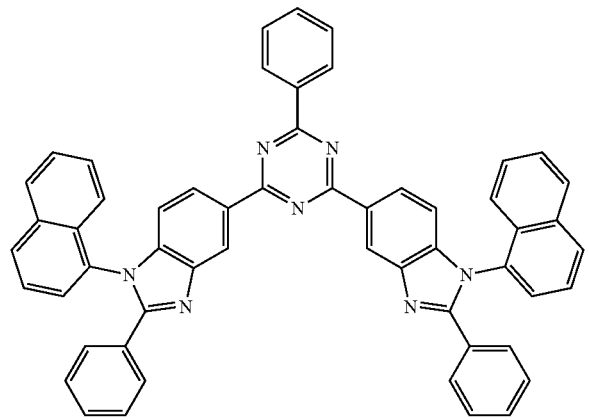
(70)
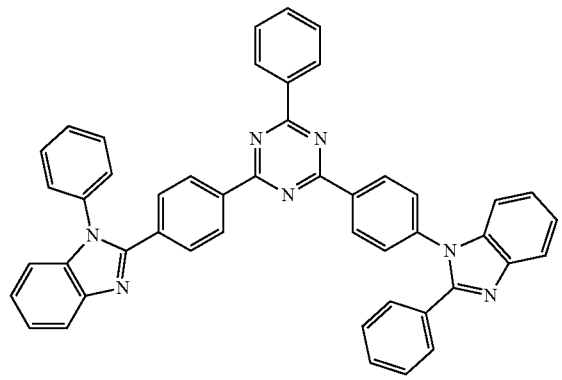
(71)
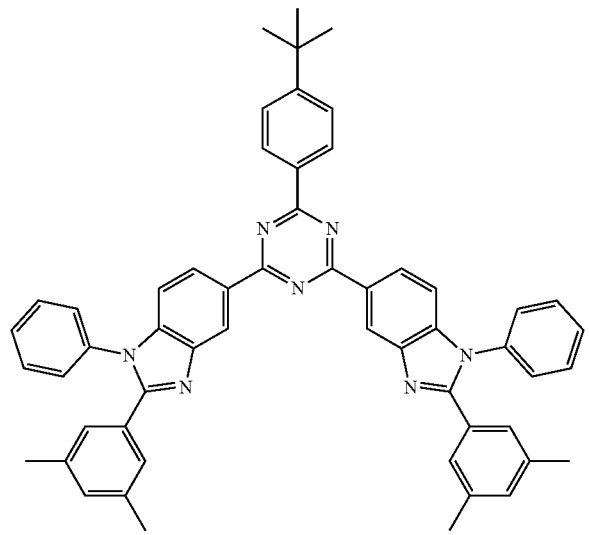
(72)
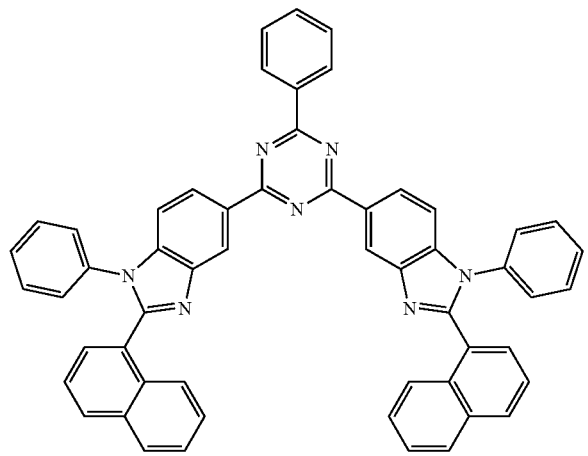
(73)
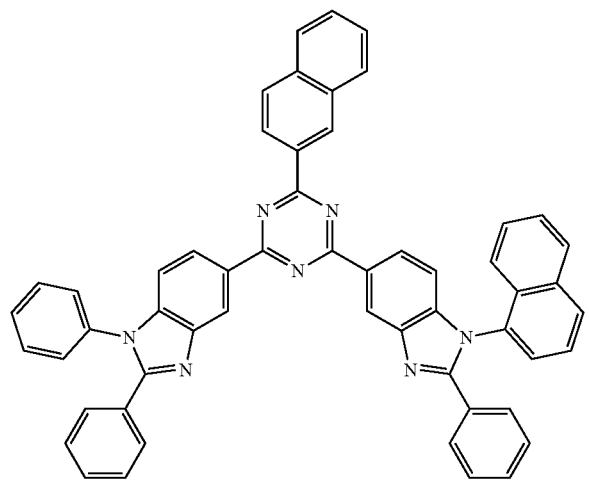
(74)
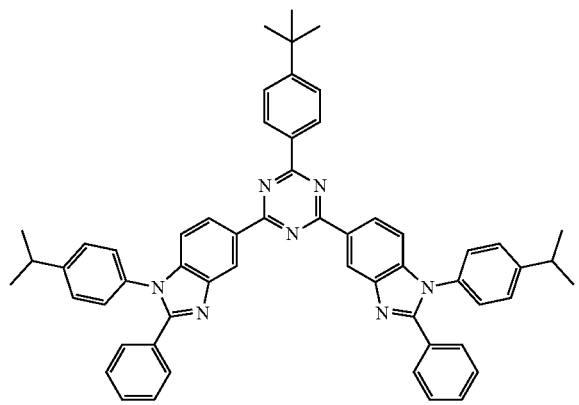

(75)
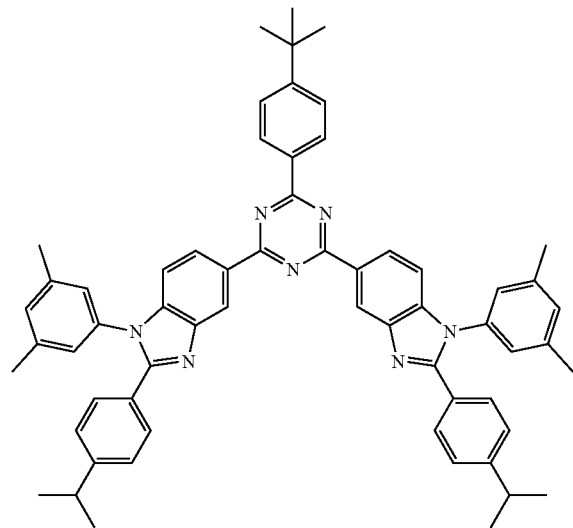
(76)
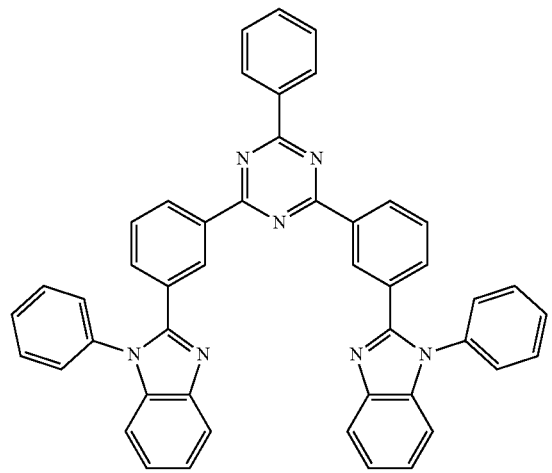
(77)
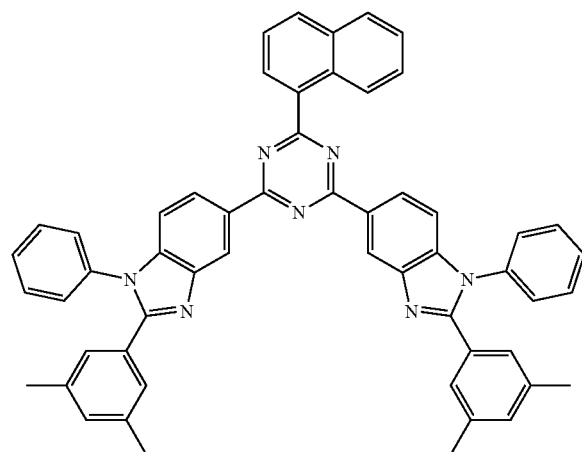
(78)
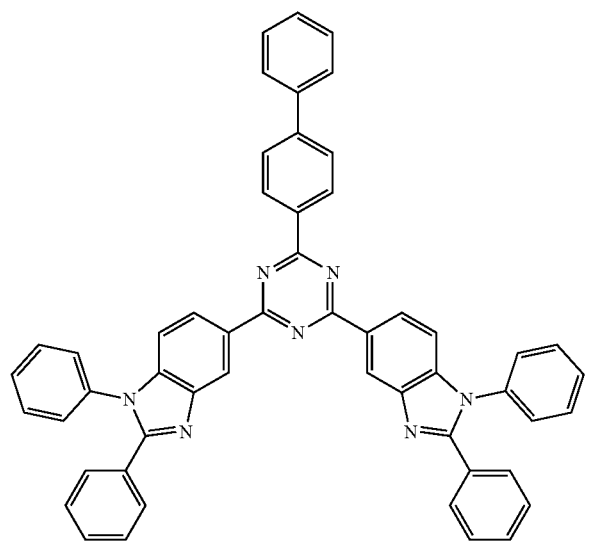
(79)
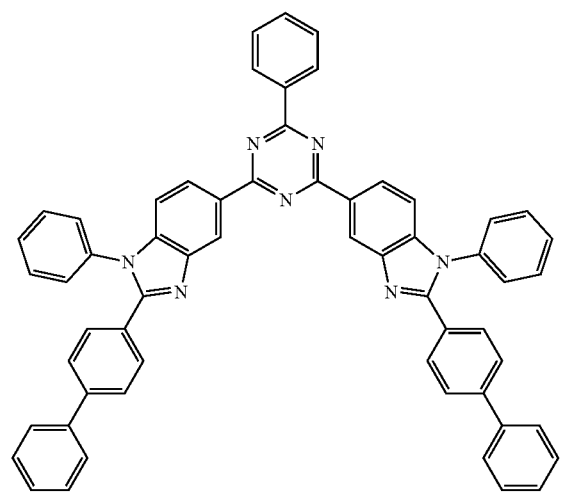
(80)
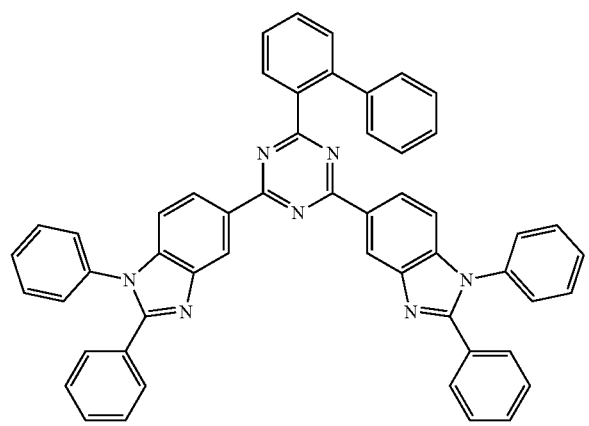

(81)
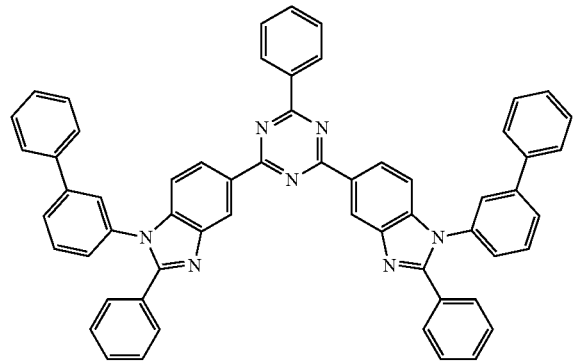
(82)
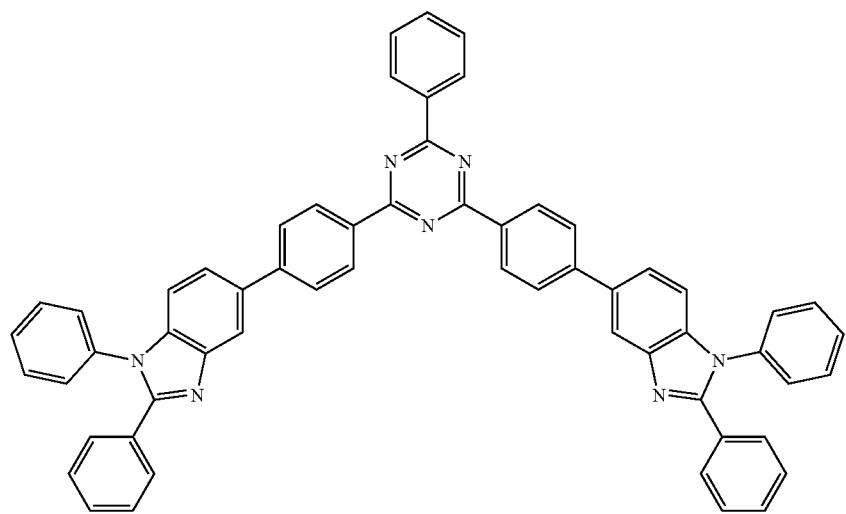
(83)
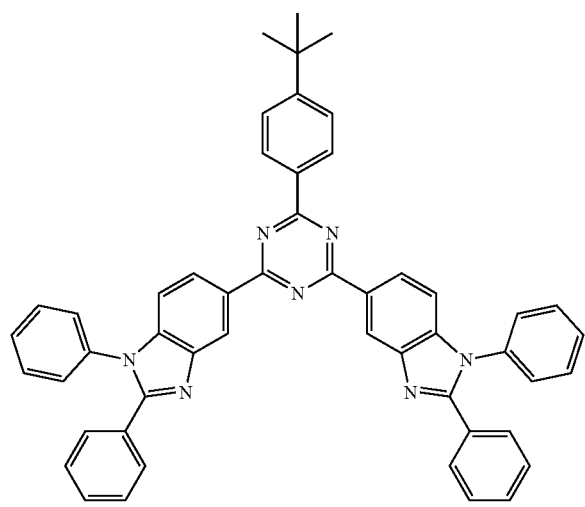
(84)
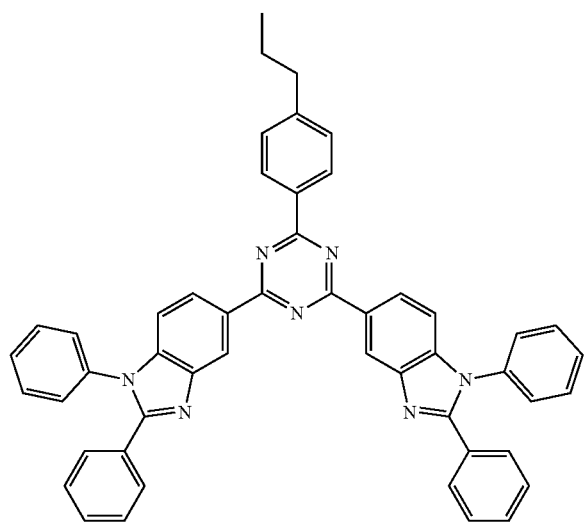

-continued
(85)
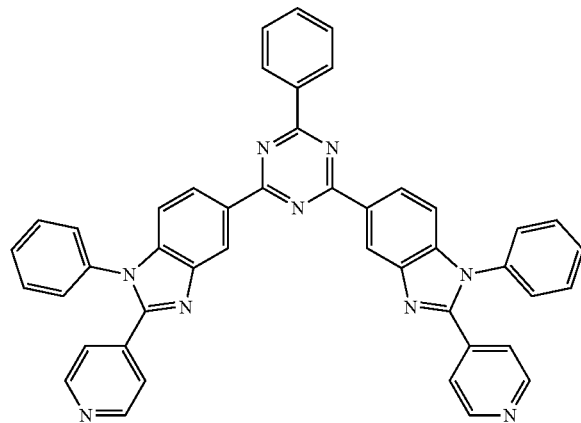
(86)
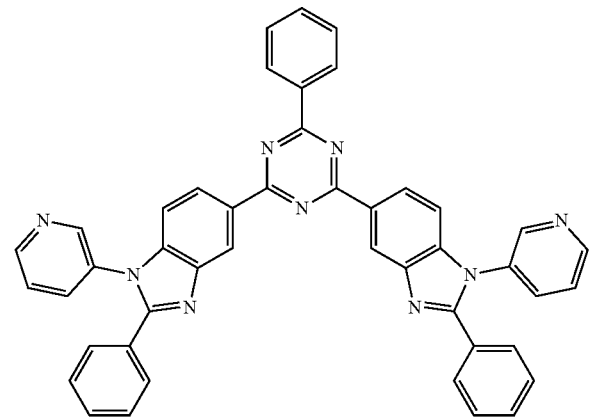
(87)
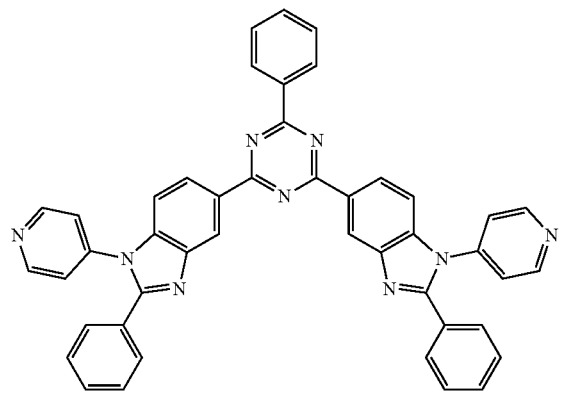
(88)
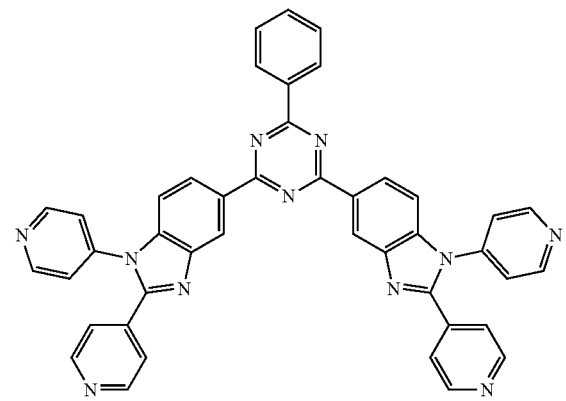
(89)
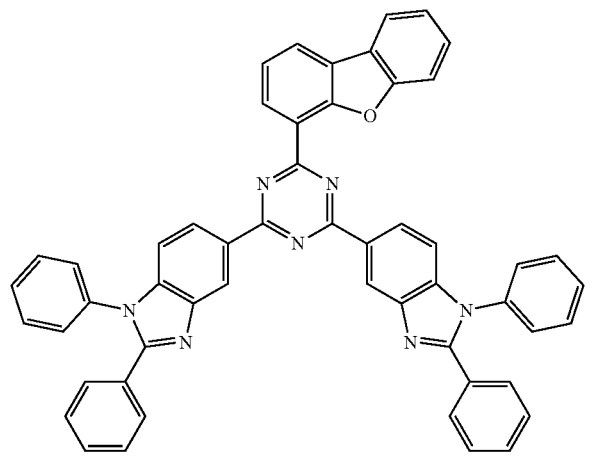
(90)
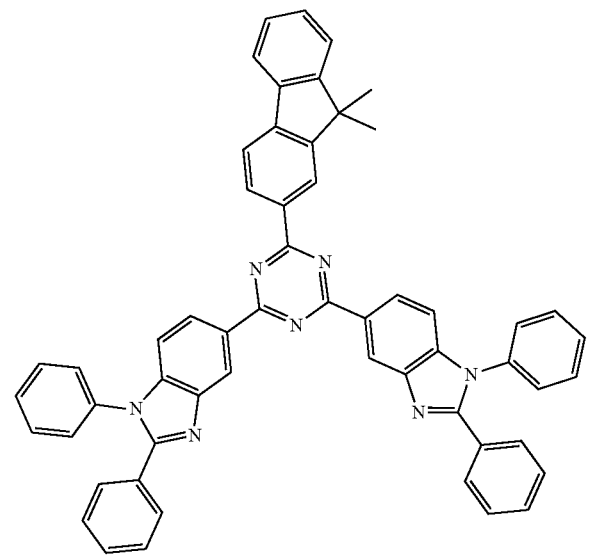

-continued
(91)
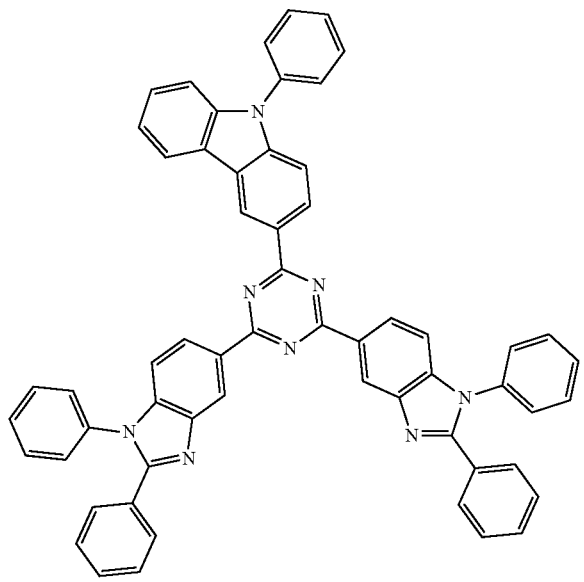
(92)
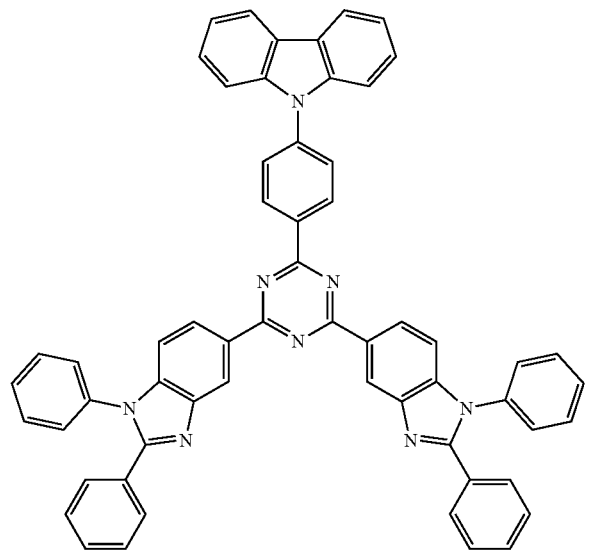
(93)
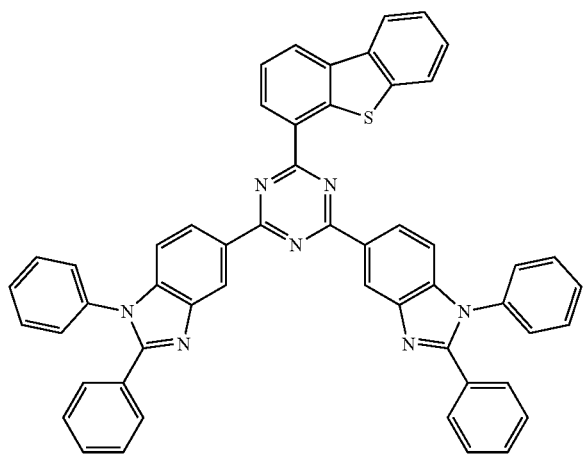
(94)
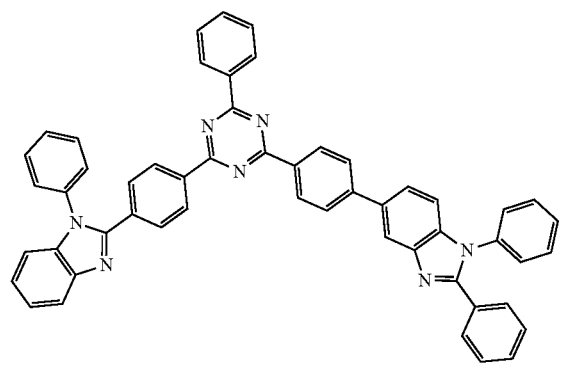
(95)
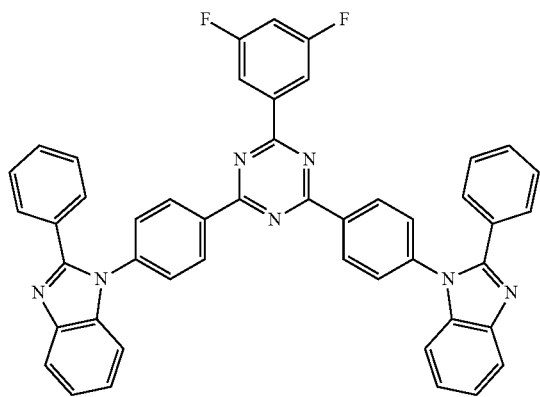
and
(96)
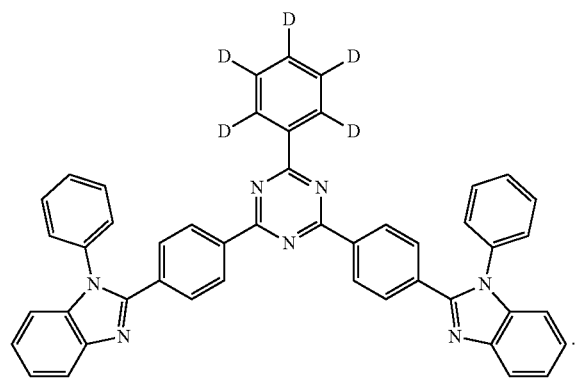

9. The organic electroluminescent device according to claim 8, wherein the organic electroluminescent device comprises at least one functional layer containing the organic compound.

10. The organic electroluminescent device according to claim 8, wherein the organic electroluminescent device comprises a hole block layer or an electron transport layer; and wherein the hole block layer or the electron transport layer contains the organic compound.

11. The organic electroluminescent device according to claim 8, wherein the organic electroluminescent device comprises a CPL layer; and wherein the CPL layer contains the organic compound.

\* \* \* \* \*